(12) United States Patent
Su et al.

(10) Patent No.: US 12,347,104 B2
(45) Date of Patent: Jul. 1, 2025

(54) METHODS AND SYSTEMS FOR PERFORMING REAL-TIME RADIOLOGY

(71) Applicant: Whiterabbit.ai Inc., Santa Clara, CA (US)

(72) Inventors: Jason Su, Santa Clara, CA (US); Rakesh Mathur, Santa Clara, CA (US); Brent Mombourquette, Toronto (CA); Thomas Matthews, Santa Clara, CA (US)

(73) Assignee: Whiterabbit.ai Inc., Santa Clara, CA (US)

( * ) Notice: Subject to any disclaimer, the term of this patent is extended or adjusted under 35 U.S.C. 154(b) by 362 days.

(21) Appl. No.: 17/860,310

(22) Filed: Jul. 8, 2022

(65) Prior Publication Data
US 2023/0005151 A1    Jan. 5, 2023

Related U.S. Application Data

(63) Continuation of application No. PCT/US2021/012625, filed on Jan. 8, 2021.
(Continued)

(51) Int. Cl.
*G06T 7/00* (2017.01)
*G06V 10/25* (2022.01)
(Continued)

(52) U.S. Cl.
CPC .......... *G06T 7/0012* (2013.01); *G06T 7/0016* (2013.01); *G06V 10/25* (2022.01);
(Continued)

(58) Field of Classification Search
USPC ....................................................... 382/132
See application file for complete search history.

(56) References Cited

U.S. PATENT DOCUMENTS 7,664,604 B1    2/2010 Heine et al.
2002/0054700 A1    5/2002 Karssemeijer et al.
(Continued)

FOREIGN PATENT DOCUMENTS

WO    WO-2021067843 A1    4/2021
WO    WO-2021142209 A1    7/2021
(Continued)

OTHER PUBLICATIONS

Lehman et al., Mammographic breast density assessment using deep learning: Clinical implementation. Radiology. 290(1):52-58 (2019).
(Continued)

*Primary Examiner* — Jacky X Zheng
(74) *Attorney, Agent, or Firm* — WILSON SONSINI GOODRICH & ROSATI

(57) ABSTRACT

The present disclosure provides methods and systems directed to performing real-time and/or AI-assisted radiology. A method for processing an image of a location of a body of a subject may comprise (a) obtaining the image of the location of a body of the subject; (b) using a trained algorithm to classify the image or a derivative thereof to a category among a plurality of categories, wherein the classifying comprises applying an image processing algorithm; (c) directing the image to a first radiologist for radiological assessment if the image is classified to a first category among the plurality of categories, or (ii) directing the image to a second radiologist for radiological assessment, if the image is classified to a second category among the plurality of categories; and (d) receiving a recommendation from the first or second radiologist to examine the subject based at least in part on the radiological assessment.

29 Claims, 35 Drawing Sheets

Related U.S. Application Data

(60) Provisional application No. 62/958,859, filed on Jan. 9, 2020.

(51) Int. Cl.
*G06V 10/764* (2022.01)
*G16H 30/40* (2018.01)
*G16H 50/20* (2018.01)

(52) U.S. Cl.
CPC ........... *G06V 10/764* (2022.01); *G16H 30/40* (2018.01); *G16H 50/20* (2018.01); *G06T 2200/04* (2013.01); *G06T 2207/10012* (2013.01); *G06T 2207/20081* (2013.01); *G06T 2207/30068* (2013.01); *G06T 2207/30096* (2013.01); *G06V 2201/03* (2022.01)

(56) References Cited

U.S. PATENT DOCUMENTS

| | | | | |
|---|---|---|---|---|
| 2004/0093166 | A1* | 5/2004 | Kil | G01N 1/06 382/128 |
| 2011/0010192 | A1 | 1/2011 | Backhaus et al. | |
| 2011/0237946 | A1* | 9/2011 | Stribling | A61B 8/483 600/443 |
| 2014/0257854 | A1 | 9/2014 | Becker et al. | |
| 2014/0379718 | A1 | 12/2014 | Halter et al. | |
| 2016/0364857 | A1 | 12/2016 | Reicher et al. | |
| 2017/0200266 | A1 | 7/2017 | Podilchuk et al. | |
| 2018/0016642 | A1 | 1/2018 | Kennedy et al. | |
| 2018/0253531 | A1* | 9/2018 | Sharma | G06V 10/764 |
| 2019/0133519 | A1* | 5/2019 | Gannot | G06T 7/0016 |
| 2019/0189268 | A1* | 6/2019 | Stoval, III | G16H 50/70 |
| 2023/0005151 | A1* | 1/2023 | Su | G06V 10/25 |

FOREIGN PATENT DOCUMENTS

| | | |
|---|---|---|
| WO | WO-2022221175 A1 | 10/2022 |
| WO | WO-2023283443 A1 | 1/2023 |

OTHER PUBLICATIONS

Mathews et al., A multisite study of a breast density deep learning model for full-field digital mammography and synthetic mammography. Radiol Artif Intell. 3(1):e200015, pp. 1-10 (2020).

PCT/US2021/012625 International Search Report and Written Opinion dated Mar. 26, 2021.

EP Serial No. 21738922.0 Extended European Search Report dated Feb. 12, 2024.

PCT/US2021/012625 International Preliminary Report on Patentability dated Jul. 12, 2022.

* cited by examiner

MG Tech/Tech Aid

STATE

Post MG

> Realtime radiology candidate
> [A.] [Lastname] may be qualified for a realtime reading
> Please answer the following
> Have prior images been requested?      ○ Yes   ○ No
> Is an ABUS scheduled?                          ○ Yes   ○ No
> Has the patient consented to the AI study?   ○ Yes   ○ No
>
> SUBMIT

Qualified

> Realtime radiology candidate
> Please inform [A.] [Lastname] to wait for their results

Post US

> Realtime radiology candidate
> [A.] [Lastname] ABUS images are received.

Leave clinic

> Reading patient
> [A.] [Lastname] is not a RTR candidate and may leave.

FIG. 3A

Radiologists

STATE

Post MG

Qualified

Post US

Billing

STATE

Post MG

Qualified

[A.] [Lastname] has qualified for a realtime reading.
Please estimate diagnostic costs.

US Tech/Tech Aid

STATE

Post MG

Qualified

[A.] [Lastname] has qualified for a realtime reading.
Please inform them to wait for their results.

FIG. 3D

METHODS AND SYSTEMS FOR PERFORMING REAL-TIME RADIOLOGY

CROSS-REFERENCE

This application is a continuation of International Application No. PCT/US2021/012625, filed Jan. 8, 2021, which claims the benefit of U.S. Provisional Application No. 62/958,859, filed Jan. 9, 2020, each of which is incorporated by reference herein in its entirety.

BACKGROUND

Breast cancer is the most widespread cancer in women in the U.S., with over 250 thousand new diagnoses in 2017 alone. About 1 in 8 women will be diagnosed with breast cancer at some point during their lives. Despite improvements in treatment, over 40 thousand women die every year in the U.S. from breast cancer. Substantial progress has been made in reducing breast cancer mortality in part due to the widespread adoption of screening mammography. Breast cancer screening can help identify early-stage cancers, which have much better prognoses and lower treatment costs as compared to late-stage cancers. This difference can be substantial: women with localized breast cancer have a 5-year survival rate of nearly 99%, while women with metastatic breast cancer have a 5-year survival rate of 27%.

Despite these demonstrated benefits, adoption rates for screening mammography are hindered, in part, by poor patient experience, such as long delays in obtaining an appointment, unclear pricing, long wait times to receive exam results, and confusing reports. Further, problems arising from a lack of transparency in pricing are exacerbated by large variations in costs among providers. Similarly, delivery times for receiving exam results are inconsistent among providers. In addition, significant variation in radiologist performance results in patients experiencing very different standards of care depending on location and income.

SUMMARY

The present disclosure provides methods and systems for performing radiological assessment of subjects by stratifying medical image data using artificial intelligence into distinct radiological workflows for further screening and/or diagnostic assessment. Such subjects may include subjects with a disease (e.g., cancer) and subjects without a disease (e.g., cancer). The screening may be for a cancer such as, for example, breast cancer. The stratification may be performed based on disease-related assessments or other assessments (e.g., estimated case difficulty).

In an aspect, the present disclosure provides a method for processing at least one image of a location of a body of the subject, comprising: (a) obtaining the at least one image of the location of a body of the subject; (b) using a trained algorithm to classify the at least one image or a derivative thereof to a category among a plurality of categories, wherein the classifying comprises applying an image processing algorithm to the at least one image or derivative thereof; (c) upon classifying the at least one image or derivative thereof in (b), (i) directing the at least one image or derivative thereof to a first radiologist for radiological assessment if the at least one image is classified to a first category among the plurality of categories, or (ii) directing the at least one image or derivative thereof to a second radiologist for radiological assessment, if the at least one image is classified to a second category among the plurality of categories; and (d) receiving a radiological assessment of the subject from the first or second radiologist based at least in part on a radiological analysis of the at least one image or derivative thereof.

In some embodiments, (b) comprises classifying the at least one image or derivative thereof as normal, ambiguous, or suspicious. In some embodiments, the method further comprises directing the at least one image or derivative thereof to a classifier based on the classification of the at least one image or derivative thereof in (b). In some embodiments, (c) comprises directing the at least one image or derivative thereof to a first radiologist from among a first plurality of radiologists or to a second radiologist from among a second plurality of radiologists for radiological assessment. In some embodiments, the at least one image or derivative thereof is a medical image.

In some embodiments, the trained algorithm is configured to classify the at least one image or derivative thereof as normal, ambiguous, or suspicious at a sensitivity of at least about 80%. In some embodiments, the trained algorithm is configured to classify the at least one image or derivative thereof as normal, ambiguous, or suspicious at a specificity of at least about 80%. In some embodiments, the trained algorithm is configured to classify the at least one image or derivative thereof as normal, ambiguous, or suspicious at a positive predictive value of at least about 80%. In some embodiments, the trained algorithm is configured to classify the at least one image or derivative thereof as normal, ambiguous, or suspicious at a negative predictive value of at least about 80%.

In some embodiments, the trained machine learning algorithm is configured to identify the at least one region of the at least one image or derivative thereof that contains or is suspected of containing the anomalous tissue.

In some embodiments, a trained algorithm classifies the at least one image or a derivative thereof as normal, ambiguous, or suspicious for being indicative of a cancer. In some embodiments, the cancer is breast cancer. In some embodiments, the at least one image or derivative thereof is a three-dimensional image of the breast of the subject. In some embodiments, the trained machine learning algorithm is trained using at least about 100 independent training samples comprising images that are indicative of or suspected of being indicative of a cancer.

In some embodiments, the trained algorithm is trained using a first plurality of independent training samples comprising positive images that are indicative of or suspected of being indicative of a cancer and a second plurality of independent training samples comprising negative images that are not indicative of or not suspected of being indicative of a cancer. In some embodiments, the trained algorithm comprises a supervised machine learning algorithm. In some embodiments, the supervised machine learning algorithm comprises a deep learning algorithm, a support vector machine (SVM), a neural network, or a Random Forest.

In some embodiments, the method further comprises monitoring the subject, wherein the monitoring comprises assessing images of the location of the body of the subject at a plurality of time points, wherein the assessing is based at least in part on the classification of the at least one image or a derivative thereof as normal, ambiguous, or suspicious at each of the plurality of time points. In some embodiments, a difference in the assessment of the images of the body of the subject at the plurality of time points is indicative of one or more clinical indications selected from the group consisting of: (i) a diagnosis of the subject, (ii) a prognosis of the subject, and (iii) an efficacy or non-efficacy of a course of treatment of the subject.

In some embodiments, (c) further comprises (i) directing the at least one image or derivative thereof to a first radiologist among a first set of radiologists for radiological assessment to produce a screening result, based at least in part on whether the at least one image is classified as suspicious; (ii) directing the at least one image or derivative thereof to a second radiologist among a second set of radiologists for radiological assessment to produce a screening result, based at least in part on whether the at least one image is classified as ambiguous; or (iii) directing the at least one image or derivative thereof to a third radiologist among a third set of radiologists for radiological assessment to produce a screening result, based at least in part on whether the at least one image is classified as normal. In some embodiments, (c) further comprises directing the at least one image or derivative thereof to a first radiologist among a first set of radiologists for radiological assessment to produce a screening result, if the at least one image is classified as suspicious. In some embodiments, (c) further comprises directing the at least one image or derivative thereof to a second radiologist among a second set of radiologists for radiological assessment to produce a screening result, if the at least one image is classified as ambiguous. In some embodiments, (c) further comprises directing the at least one image or derivative thereof to a third radiologist among a third set of radiologists for radiological assessment to produce a screening result, if the at least one image is classified as normal. In some embodiments, the screening result of the subject is produced at a same clinic visit as the obtaining of the at least one image or derivative thereof. In some embodiments, the first set of radiologists is located at an on-site clinic, wherein the at least one image or derivative thereof is obtained at the on-site clinic.

In some embodiments, the second set of radiologists comprises expert radiologists, which expert radiologists are trained to classify the at least one image or derivative thereof as normal or suspicious at a greater accuracy than the trained algorithm. In some embodiments, the third set of radiologists is located remotely to an onsite clinic, wherein the at least one image is obtained at the on-site clinic. In some embodiments, the third radiologist of the third set of radiologists performs the radiologist assessment of the at least one image or derivative thereof among a batch comprising a plurality of images, wherein the batch is selected for enhanced efficiency of the radiological assessment.

In some embodiments, the method further comprises performing a diagnostic procedure of the subject, based at least in part on the screening result, to produce a diagnostic result of the subject. In some embodiments, the diagnostic result of the subject is produced at a same clinic visit as the obtaining of the at least one image. In some embodiments, the diagnostic result of the subject is produced within about one hour of the obtaining of the at least one image.

In some embodiments, the at least one image or derivative thereof is directed to the first radiologist, the second radiologist, or the third radiologist based at least in part on additional characteristics of the location of the body of the subject. In some embodiments, the additional characteristics comprise an anatomy, tissue characteristics (e.g., tissue density or physical properties), a presence of a foreign object (e.g., implants), a type of finding, an appearance of disease (e.g., predicted by an algorithm such as a machine learning algorithm), or a combination thereof.

In some embodiments, the at least one image or derivative thereof is directed to the first radiologist, the second radiologist, or the third radiologist based at least in part on additional characteristics of the first radiologist, the second radiologist, or the third radiologist (e.g., a personal ability of the first radiologist, the second radiologist, or the third radiologist to perform a radiological assessment of the at least one image or derivative thereof).

In some embodiments, (c) further comprises generating an alert based at least in part on the directing of the at least one image or derivative thereof to the first radiologist or the directing of the at least one image or derivative thereof to the second radiologist. In some embodiments, the method further comprises transmitting the alert to the subject or to a clinical health care provider of the subject. In some embodiments, the method further comprises transmitting the alert to the subject through a patient mobile application. In some embodiments, the alert is generated in real time or substantially real time as (b).

In some embodiments, applying the image processing algorithm comprises identifying regions of interest within the at least one image or derivative thereof, and labeling the regions of interest to produce at least one labeled image. In some embodiments, the method further comprises storing the at least one labeled image in a database. In some embodiments, the method further comprises storing one or more of the at least one image or derivative thereof and the classification in a database. In some embodiments, the method further comprises generating a presentation of the at least one image based at least in part on one or more of the at least one image or derivative thereof and the classification. In some embodiments, the method further comprises storing the presentation in the database.

In some embodiments, (c) is performed in real time or substantially real time as (b). In some embodiments, the at least one image comprises a plurality of images obtained from the subject, wherein the plurality of images are obtained using different modalities or at different time points. In some embodiments, the classifying comprises processing clinical health data of the subject.

In another aspect, the present disclosure provides a computer system for processing at least one image of a location of a body of the subject: a database that is configured to store the at least one image of the location of a body of the subject; and one or more computer processors operatively coupled to the database, wherein the one or more computer processors are individually or collectively programmed to: (a) use a trained algorithm to classify the at least one image or a derivative thereof to a category among a plurality of categories, wherein the classifying comprises applying an image processing algorithm to the at least one image or derivative thereof; (b) upon classifying the at least one image or derivative thereof in (a), (i) directing the at least one image or derivative thereof to a first radiologist for radiological assessment if the at least one image is classified to a first category among the plurality of categories, or (ii) directing the at least one image or derivative thereof to a second radiologist for radiological assessment, if the at least one image is classified to a second category among the plurality of categories; and (c) receive a radiological assessment of the subject from the first or second radiologist based at least in part on a radiological analysis of the at least one image or derivative thereof.

In some embodiments, (a) comprises classifying the at least one image or derivative thereof as normal, ambiguous, or suspicious. In some embodiments, the one or more computer processors are individually or collectively programmed to further direct the at least one image or derivative thereof to a classifier based on the classification of the at least one image or derivative thereof in (a). In some embodiments, (b) comprises directing the at least one image or derivative thereof to a first radiologist from among a first plurality of radiologists or to a second radiologist from among a second plurality of radiologists for radiological assessment. In some embodiments, the at least one image or derivative thereof is a medical image.

In some embodiments, the trained algorithm is configured to classify the at least one image or derivative thereof as normal, ambiguous, or suspicious at a sensitivity of at least about 80%. In some embodiments, the trained algorithm is configured to classify the at least one image or derivative thereof as normal, ambiguous, or suspicious at a specificity of at least about 80%. In some embodiments, the trained algorithm is configured to classify the at least one image or derivative thereof as normal, ambiguous, or suspicious at a positive predictive value of at least about 80%. In some embodiments, the trained algorithm is configured to classify the at least one image or derivative thereof as normal, ambiguous, or suspicious at a negative predictive value of at least about 80%. In some embodiments, the trained machine learning algorithm is configured to identify the at least one region of the at least one image or derivative thereof that contains or is suspected of containing the anomalous tissue.

In some embodiments, a trained algorithm classifies the at least one image or a derivative thereof as normal, ambiguous, or suspicious for being indicative of a cancer. In some embodiments, the cancer is breast cancer. In some embodiments, the at least one image or derivative thereof is a three-dimensional image of the breast of the subject. In some embodiments, the trained machine learning algorithm is trained using at least about 100 independent training samples comprising images that are indicative of or suspected of being indicative of a cancer.

In some embodiments, the trained algorithm is trained using a first plurality of independent training samples comprising positive images that are indicative of or suspected of being indicative of a cancer and a second plurality of independent training samples comprising negative images that are not indicative of or not suspected of being indicative of a cancer. In some embodiments, the trained algorithm comprises a supervised machine learning algorithm. In some embodiments, the supervised machine learning algorithm comprises a deep learning algorithm, a support vector machine (SVM), a neural network, or a Random Forest.

In some embodiments, the one or more computer processors are individually or collectively programmed to further monitor the subject, wherein the monitoring comprises assessing images of the location of the body of the subject at a plurality of time points, wherein the assessing is based at least in part on the classification of the at least one image or a derivative thereof as normal, ambiguous, or suspicious at each of the plurality of time points. In some embodiments, a difference in the assessment of the images of the body of the subject at the plurality of time points is indicative of one or more clinical indications selected from the group consisting of: (i) a diagnosis of the subject, (ii) a prognosis of the subject, and (iii) an efficacy or non-efficacy of a course of treatment of the subject.

In some embodiments, (b) further comprises (i) directing the at least one image or derivative thereof to a first radiologist among a first set of radiologists for radiological assessment to produce a screening result, based at least in part on whether the at least one image or derivative thereof is classified as suspicious; (ii) directing the at least one image or derivative thereof to a second radiologist among a second set of radiologists for radiological assessment to produce a screening result, based at least in part on whether the at least one image or derivative thereof is classified as ambiguous; or (iii) directing the at least one image or derivative thereof to a third radiologist among a third set of radiologists for radiological assessment to produce a screening result, based at least in part on whether the at least one image or derivative thereof is classified as normal. In some embodiments, (b) further comprises directing the at least one image or derivative thereof to a first radiologist among a first set of radiologists for radiological assessment to produce a screening result, if the at least one image is classified as suspicious. In some embodiments, (b) further comprises directing the at least one image or derivative thereof to a second radiologist among a second set of radiologists for radiological assessment to produce a screening result, if the at least one image is classified as ambiguous. In some embodiments, (b) further comprises directing the at least one image or derivative thereof to a third radiologist among a third set of radiologists for radiological assessment to produce a screening result, if the at least one image is classified as normal. In some embodiments, the screening result of the subject is produced at a same clinic visit as the obtaining of the at least one image. In some embodiments, the first set of radiologists is located at an on-site clinic, wherein the at least one image is obtained at the on-site clinic.

In some embodiments, the second set of radiologists comprises expert radiologists, which expert radiologists are trained to classify the at least one image or derivative thereof as normal or suspicious at a greater accuracy than the trained algorithm. In some embodiments, the third set of radiologists is located remotely to an onsite clinic, wherein the at least one image is obtained at the on-site clinic. In some embodiments, the third radiologist of the third set of radiologists performs the radiologist assessment of the at least one image or derivative thereof among a batch comprising a plurality of images, wherein the batch is selected for enhanced efficiency of the radiological assessment.

In some embodiments, the one or more computer processors are individually or collectively programmed to further obtain a diagnostic result of the subject from a diagnostic procedure performed on the subject, based at least in part on the screening result. In some embodiments, the diagnostic result of the subject is produced at a same clinic visit as the obtaining of the at least one image. In some embodiments, the diagnostic result of the subject is produced within about one hour of the obtaining of the at least one image.

In some embodiments, the at least one image or derivative thereof is directed to the first radiologist, the second radiologist, or the third radiologist based at least in part on additional characteristics of the location of the body of the subject. In some embodiments, the additional characteristics comprise an anatomy, tissue characteristics (e.g., tissue density or physical properties), a presence of a foreign object (e.g., implants), a type of finding, an appearance of disease (e.g., predicted by an algorithm such as a machine learning algorithm), or a combination thereof.

In some embodiments, the at least one image or derivative thereof is directed to the first radiologist, the second radiologist, or the third radiologist based at least in part on additional characteristics of the first radiologist, the second radiologist, or the third radiologist (e.g., a personal ability of the first radiologist, the second radiologist, or the third radiologist to perform a radiological assessment of the at least one image or derivative thereof).

In some embodiments, (b) further comprises generating an alert based at least in part on the directing of the at least one image or derivative thereof to the first radiologist or the directing of the at least one image or derivative thereof to the second radiologist. In some embodiments, the one or more computer processors are individually or collectively programmed to further transmit the alert to the subject or to a clinical health care provider of the subject. In some embodiments, the one or more computer processors are individually or collectively programmed to further transmit the alert to the subject through a patient mobile application. In some embodiments, the alert is generated in real time or substantially real time as (a).

In some embodiments, applying the image processing algorithm comprises identifying regions of interest within the at least one image or derivative thereof, and labeling the regions of interest to produce at least one labeled image. In some embodiments, the one or more computer processors are individually or collectively programmed to further store the at least one labeled image in a database. In some embodiments, the one or more computer processors are individually or collectively programmed to further store one or more of the at least one image or derivative thereof and the classification in a database. In some embodiments, the one or more computer processors are individually or collectively programmed to further generate a presentation of the at least one image or derivative thereof based at least in part on one or more of the at least one image and the classification. In some embodiments, the one or more computer processors are individually or collectively programmed to further store the presentation in the database.

In some embodiments, (b) is performed in real time or substantially real time as (a). In some embodiments, the at least one image comprises a plurality of images obtained from the subject, wherein the plurality of images are obtained using different modalities or at different time points. In some embodiments, the classifying comprises processing clinical health data of the subject.

Another aspect of the present disclosure provides a non-transitory computer readable medium comprising machine executable code that, upon execution by one or more computer processors, implements any of the methods above or elsewhere herein.

Another aspect of the present disclosure provides a system comprising one or more computer processors and computer memory coupled thereto. The computer memory comprises machine executable code that, upon execution by the one or more computer processors, implements any of the methods above or elsewhere herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

FIGS. 3A-3D show an example of a user interface for a real-time radiology system, in accordance with disclosed embodiments, including views from the perspective of a mammography technologist or technologist's assistant (FIG. 3A), a radiologist (FIG. 3B), a billing representative (FIG. 3C), and an ultrasound technologist or technologist's assistant (FIG. 3D).

DETAILED DESCRIPTION

Figure 1:
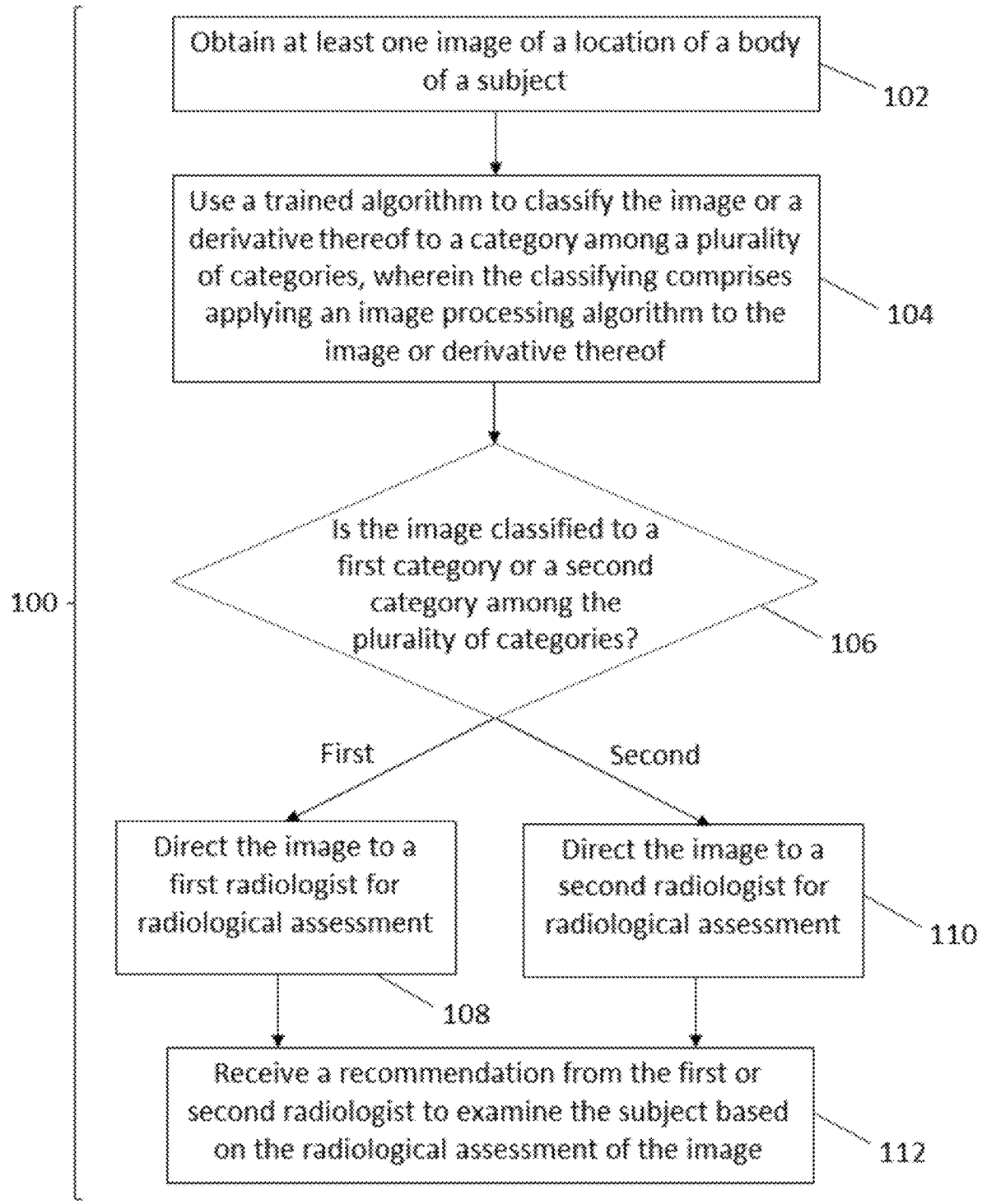
FIG. 1 illustrates an example workflow of a method for directing cases for radiological review (e.g., by a radiologist or radiologic technologist), in accordance with disclosed embodiments.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

As used in the specification and claims, the singular form "a", "an", and "the" include plural references unless the context clearly dictates otherwise. For example, the term "a nucleic acid" includes a plurality of nucleic acids, including mixtures thereof.

As used herein, the term "subject," generally refers to an entity or a medium that has testable or detectable genetic information. A subject can be a person, individual, or patient. A subject can be a vertebrate, such as, for example, a mammal. Non-limiting examples of mammals include humans, simians, farm animals, sport animals, rodents, and pets. The subject can be a person that has a cancer or is suspected of having a cancer. The subject may be displaying a symptom(s) indicative of a health or physiological state or condition of the subject, such as a cancer (e.g., breast cancer) of the subject. As an alternative, the subject can be asymptomatic with respect to such health or physiological state or condition.

Breast cancer is the most widespread cancer in women in the U.S., with over 250 thousand new diagnoses in 2017 alone. About 1 in 8 women will be diagnosed with breast cancer at some point during their lives. Despite improvements in treatment, over 40 thousand women die every year in the U.S. from breast cancer. Substantial progress has made in reducing breast cancer mortality in part due to the widespread adoption of screening mammography. Breast cancer screening can help identify early-stage cancers, which have much better prognoses and lower treatment costs as compared to late-stage cancers. This difference can be substantial: women with localized breast cancer have a 5-year survival rate of nearly 99%, while women with metastatic breast cancer have a 5-year survival rate of 27%.

Despite these demonstrated benefits, adoption rates for screening mammography are hindered, in part, by poor patient experience, such as long delays in obtaining an appointment, unclear pricing, long wait times to receive exam results, and confusing reports. Further, problems arising from a lack of transparency in pricing are exacerbated by large variations in costs among providers. Similarly, delivery times for receiving exam results are inconsistent among providers. In addition, significant variation in radiologist performance results in patients experiencing very different standards of care depending on location and income.

The present disclosure provides methods and systems for performing real-time radiology of subjects by stratifying medical image data using artificial intelligence into distinct radiological workflows for further screening and/or diagnostic assessment. Such subjects may include subjects with a cancer and subjects without cancer. The screening may be for a cancer such as, for example, breast cancer.

FIG. 1 illustrates an example workflow of a method for directing cases for radiological review (e.g., by a radiologist, radiologic technician, or radiologic technologist), in accordance with disclosed embodiments. In an aspect, the present disclosure provides a method 100 for processing at least one image of a location of a body of a subject. The method 100 may comprise obtaining the image of the location of a body of the subject (as in operation 102). Next, the method 100 may comprise using a trained algorithm to classify the image or a derivative thereof to a category among a plurality of categories (as in operation 104). For example, the classifying may comprise applying an image processing algorithm to the image or derivative thereof. Next, the method 100 may comprise determining whether the image was classified to a first category or a second category among the plurality of categories (as in operation 106). If the image was classified to the first category, then the method 100 may comprise directing the image to a first radiologist for radiological assessment (as in operation 108). If the image was classified to the second category, then the method 100 may comprise directing the image to a second radiologist for radiological assessment (as in operation 110). Next, the method 100 may comprise receiving a recommendation (e.g., from the first or second radiologist, or from another radiologist or physician) to examine the subject based on the radiological assessment of the image (as in operation 112).

Figure 2:
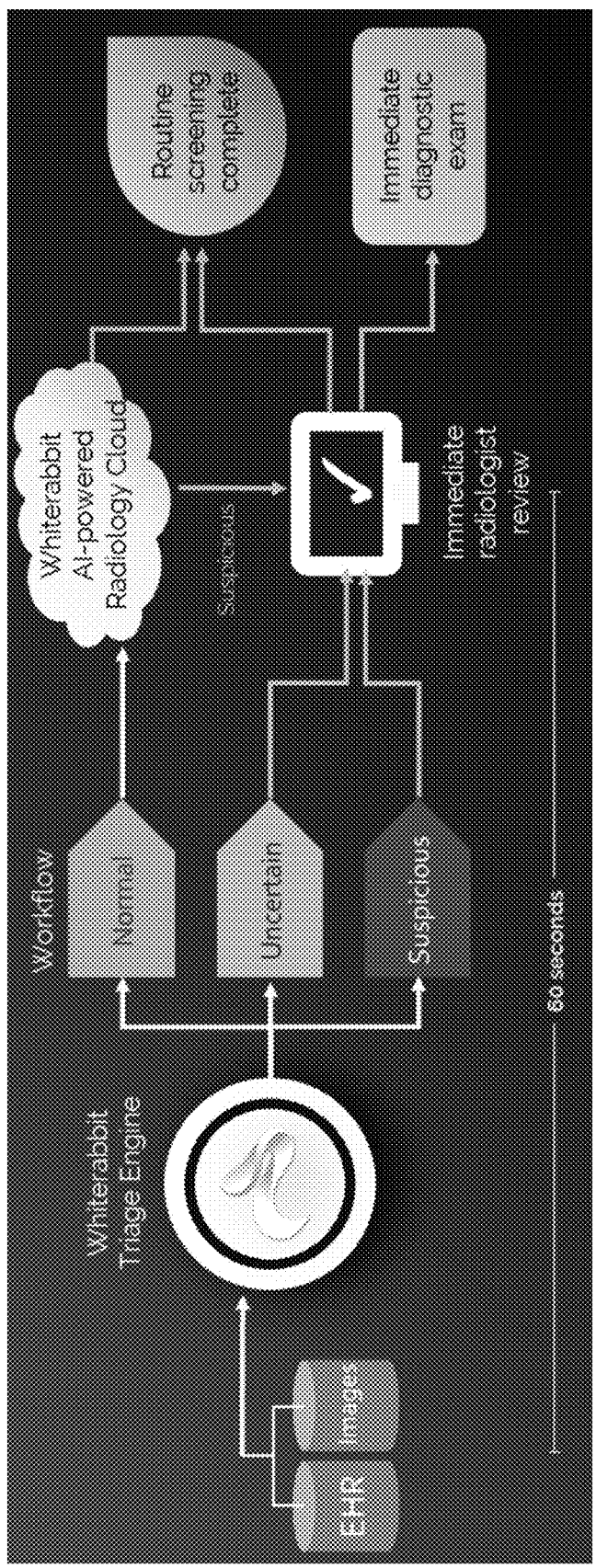
FIG. 2 illustrates an example of a method of using a triage engine configured to stratify a subject who is undergoing mammographic screening by classifying the mammographic data of the subject into one of three different workflows: normal, uncertain, and suspicious, in accordance with disclosed embodiments.

FIG. 2 illustrates an example of a method of using a triage engine configured to stratify a subject who is undergoing mammographic screening by classifying the mammographic data of the subject into one of three different workflows: normal, uncertain, and suspicious, in accordance with disclosed embodiments. First, a dataset comprising an electronic health record (EHR) and medical images of a patient are provided. Next, an AI-based triage engine processes the EHR and medical images to analyze and classify the dataset as likely normal, possibly suspicious, or likely suspicious. Next, the patient's dataset is processed by one of three workflows based on the classification of the dataset as normal, uncertain, or suspicious: a normal workflow, an uncertain workflow, and a suspicious workflow, respectively. Each of the three workflows may comprise radiologist review or further AI-based analysis (e.g., by a trained algorithm). The normal workflow may comprise an AI-based (optionally a cloud-based) confirmation that the patient's dataset is normal, upon which the routine screening is complete. For example, a group of radiologists may review the normal workflow cases at high volume and efficiency. Alternatively, the normal workflow may comprise an AI-based (optionally a cloud-based) determination that the patient's dataset is suspicious, upon which an immediate radiologist review of the patient's dataset is ordered. For example, a second group of radiologists may review the suspicious workflow cases at lower volume and lower efficiency (e.g., expert radiologists conducting more detailed radiological assessments). Similarly, the uncertain and suspicious workflow may also comprise an immediate radiologist review of the patient's dataset. In some embodiments, different sets of radiologists are used to review the different workflows, as described elsewhere herein. In some embodiments, the same sets of radiologists are used to review the different workflows (e.g., at different time points depending on a prioritization of the cases for radiological assessment).

Figure 3B:
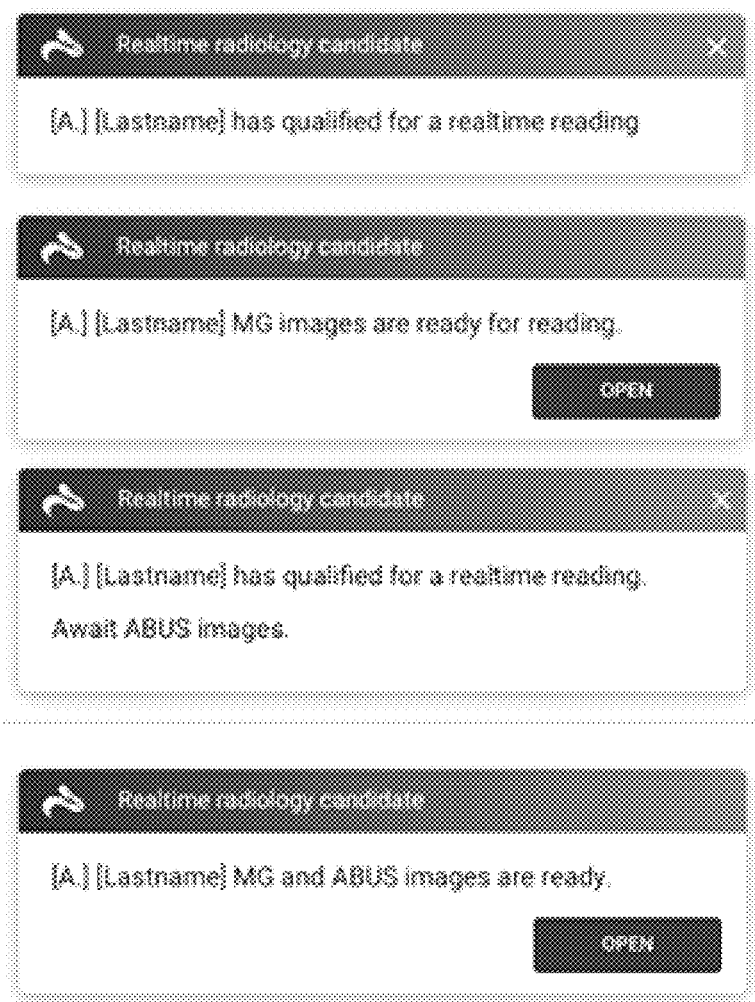
Figure 3C:

FIGS. 3A-3D show an example of a user interface for a real-time radiology system, in accordance with disclosed embodiments, including views from the perspective of a mammography technologist or technologist's assistant (FIG. 3A), a radiologist (FIG. 3B), a billing representative (FIG. 3C), and an ultrasound technician or technician's assistant (FIG. 3D). The view may include a heatmap showing which regions were identified as suspicious by the AI algorithm. The mammography technologist or technologist's assistant may ask the patient some questions and evaluate the responses to the questions to assess whether the patient is qualified for a real-time radiology assessment. The radiologist may read or interpret the medical images (e.g., mammography images) of the patient in accordance with the real-time radiology methods and systems of the present disclosure. The billing representative may estimate the diagnostic costs based on the patient's qualification for a real-time radiology assessment. The mammography/ultrasound technologist or technologist's assistant may inform the patient to wait for their results of the real-time radiology assessment. The user interface may provide a notification (e.g., generated by an AI-based algorithm) to the technologist or technologist's assistant that an acquired image is of poor quality, so that the technologist or technologist's assistant can make a correction to the acquired image or repeat the image acquisition.

Obtaining Medical Images

The medical images may be obtained or derived from a human subject (e.g., a patient). The medical images may be stored in a database, such as a computer server (e.g., cloud-based server), a local server, a local computer, or a mobile device (such as smartphone or tablet)). The medical images may be obtained from a subject with cancer, from a subject that is suspected of having cancer, or from a subject that does not have or is not suspected of having cancer.

The medical images may be taken before and/or after treatment of a subject with cancer. Medical images may be obtained from a subject during a treatment or a treatment regime. Multiple sets of medical images may be obtained from a subject to monitor the effects of the treatment over time. The medical images may be taken from a subject known or suspected of having a cancer (e.g., breast cancer) for which a definitive positive or negative diagnosis is not available via clinical tests. The medical images may be taken from a subject suspected of having cancer. The medical images may be taken from a subject experiencing unexplained symptoms, such as fatigue, nausea, weight loss, aches and pains, weakness, or bleeding. The medical images may be taken from a subject having explained symptoms. The medical images may be taken from a subject at risk of developing cancer due to factors such as familial history, age, hypertension or pre-hypertension, diabetes or pre-diabetes, overweight or obesity, environmental exposure, lifestyle risk factors (e.g., smoking, alcohol consumption, or drug use), or presence of other risk factors.

The medical images may be acquired using one or more imaging modalities, such as a mammography scan, a computed tomography (CT) scan, a magnetic resonance imaging (MRI) scan, an ultrasound scan, a digital X-ray scan, a positron emission tomography (PET) scan, a PET-CT scan, a nuclear medicine scan, a thermography scan, an ophthalmy scan, an optical coherence tomography scan, an electrocardiography scan, an endoscopy scan, a diaphanography scan, a bone densitometry scan, an optical scan, or any combination thereof. The medical images may be pre-processed using image processing techniques or deep learning to enhance image characteristics (e.g., contrast, brightness, sharpness), remove noise or artifacts, filter frequency ranges, compress the images to a small file size, or sample or crop the images. The medical images may be raw or reconstructed (e.g., to create a 3-D volume from a plurality of 2-D images). The images may be processed to compute maps that are correlated to tissue properties or functional behavior as in functional MRI (fMRI) or resting state fMRI. The images may be overlaid with heatmaps or additional information showing information like fluid flow. The images may be created from a composite of images from several scans of the same subject or from several subjects.

Trained Algorithms

After obtaining datasets comprising a plurality of medical images of a location of a body of one or more subjects, a trained algorithm may be used to process the datasets to classify the image as normal, ambiguous, or suspicious. For example, the trained algorithm may be used to determine regions of interest (ROIs) in the plurality of medical images of a subject, and to process the ROIs to classify the image as normal, ambiguous, or suspicious. The trained algorithm may be configured to classify the image as normal, ambiguous, or suspicious with an accuracy of at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, at least about 99%, or more than 99% for at least about 25, at least about 50, at least about 100, at least about 150, at least about 200, at least about 250, at least about 300, at least about 350, at least about 400, at least about 450, at least about 500, or more than about 500 independent samples.

The trained algorithm may comprise a supervised machine learning algorithm. The trained algorithm may comprise a classification and regression tree (CART) algorithm. The supervised machine learning algorithm may comprise, for example, a Random Forest, a support vector machine (SVM), a neural network (e.g., a deep neural network (DNN)), or a deep learning algorithm. The trained algorithm may comprise an unsupervised machine learning algorithm.

The trained algorithm may be configured to accept a plurality of input variables and to produce one or more output values based on the plurality of input variables. The plurality of input variables may comprise features extracted from one or more datasets comprising medical images of a location of a body of a subject. For example, an input variable may comprise a number of potentially cancerous or suspicious regions of interest (ROIs) in the dataset of medical images. The potentially cancerous or suspicious regions of interest (ROIs) may be identified or extracted from the dataset of medical images using a variety of image processing approaches, such as image segmentation. An input variable may also comprise several images from slices in a 3D volume or multiple exams over a course of time. The plurality of input variables may also include clinical health data of a subject.

In some embodiments, the clinical health data comprises one or more quantitative measures of the subject, such as age, weight, height, body mass index (BMI), blood pressure, heart rate, glucose levels. As another example, the clinical health data can comprise one or more categorical measures, such as race, ethnicity, history of medication or other clinical treatment, history of tobacco use, history of alcohol consumption, daily activity or fitness level, genetic test results, blood test results, imaging results, and screening results.

The trained algorithm may comprise one or more modules configured to perform image processing on one or more images (e.g., radiological images), thereby producing a detection or segmentation of the one or more images. The trained algorithm may comprise a classifier, such that each of the one or more output values comprises one of a fixed number of possible values (e.g., a linear classifier, a logistic regression classifier, etc.) indicating a classification of the datasets comprising medical images by the classifier. The trained algorithm may comprise a binary classifier, such that each of the one or more output values comprises one of two values (e.g., {0, 1}, {positive, negative}, {high-risk, low-risk}, or {suspicious, normal}) indicating a classification of the datasets comprising medical images by the classifier. The trained algorithm may be another type of classifier, such that each of the one or more output values comprises one of more than two values (e.g., {0, 1, 2}, {positive, negative, or indeterminate}, {high-risk, intermediate-risk, or low-risk}, or {suspicious, normal, or indeterminate}) indicating a classification of the datasets comprising medical images by the classifier. The output values may comprise descriptive labels, numerical values, or a combination thereof. Some of the output values may comprise descriptive labels. Such descriptive labels may provide an identification, indication, likelihood, or risk of a disease or disorder state of the subject, and may comprise, for example, positive, negative, high-risk, intermediate-risk, low-risk, suspicious, normal, or indeterminate. Such descriptive labels may provide an identification of a follow-up diagnostic procedure or treatment for the subject, and may comprise, for example, a therapeutic intervention, a duration of the therapeutic intervention, and/or a dosage of the therapeutic intervention suitable to treat a cancer or other condition. Such descriptive labels may provide an identification of secondary clinical tests that may be appropriate to perform on the subject, and may comprise, for example, an imaging test, a blood test, a computed tomography (CT) scan, a magnetic resonance imaging (MRI) scan, an ultrasound scan, a digital X-ray, a positron emission tomography (PET) scan, a PET-CT scan, or any combination thereof. As another example, such descriptive labels may provide a prognosis of the cancer of the subject. As another example, such descriptive labels may provide a relative assessment of the cancer (e.g., an estimated stage or tumor burden) of the subject. Some descriptive labels may be mapped to numerical values, for example, by mapping "positive" to 1 and "negative" to 0.

Some of the output values may comprise numerical values, such as binary, integer, or continuous values. Such binary output values may comprise, for example, {0, 1}, {positive, negative}, or {high-risk, low-risk}. Such integer output values may comprise, for example, {0, 1, 2}. Such continuous output values may comprise, for example, a probability value of at least 0 and no more than 1. Such continuous output values may comprise, for example, the center coordinates of an ROI. Such continuous output values may indicate a prognosis of the cancer of the subject.

Some numerical values may be mapped to descriptive labels, for example, by mapping 1 to "positive" and 0 to "negative." An array or map of numerical values may be produced, such as a probability of cancer map.

Some of the output values may be assigned based on one or more cutoff values. For example, a binary classification of datasets comprising medical images may assign an output value of "positive" or 1 if the dataset comprising medical images indicates that the subject has at least a 50% probability of having a cancer (e.g., breast cancer). For example, a binary classification of datasets comprising medical images may assign an output value of "negative" or 0 if the dataset comprising medical images indicates that the subject has less than a 50% probability of having a cancer. In this case, a single cutoff value of 50% is used to classify datasets comprising medical images into one of the two possible binary output values. Examples of single cutoff values may include about 1%, about 2%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, and about 99%.

As another example, a classification of datasets comprising medical images may assign an output value of "positive" or 1 if the dataset comprising medical images indicates that the subject has a probability of having a cancer of at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or more. The classification of samples may assign an output value of "positive" or 1 if the dataset comprising medical images indicates that the subject has a probability of having a cancer of more than about 50%, more than about 55%, more than about 60%, more than about 65%, more than about 70%, more than about 75%, more than about 80%, more than about 85%, more than about 90%, more than about 91%, more than about 92%, more than about 93%, more than about 94%, more than about 95%, more than about 96%, more than about 97%, more than about 98%, or more than about 99%.

The classification of datasets comprising medical images may assign an output value of "negative" or 0 if the dataset comprising medical images indicates that the subject has a probability of having a cancer of less than about 50%, less than about 45%, less than about 40%, less than about 35%, less than about 30%, less than about 25%, less than about 20%, less than about 15%, less than about 10%, less than about 9%, less than about 8%, less than about 7%, less than about 6%, less than about 5%, less than about 4%, less than about 3%, less than about 2%, or less than about 1%. The classification of dataset comprising medical images may assign an output value of "negative" or 0 if the dataset comprising medical images indicates that the subject has a probability of having a cancer of no more than about 50%, no more than about 45%, no more than about 40%, no more than about 35%, no more than about 30%, no more than about 25%, no more than about 20%, no more than about 15%, no more than about 10%, no more than about 9%, no more than about 8%, no more than about 7%, no more than about 6%, no more than about 5%, no more than about 4%, no more than about 3%, no more than about 2%, or no more than about 1%.

The classification of datasets comprising medical images may assign an output value of "indeterminate" or 2 if the dataset comprising medical images is not classified as "positive", "negative", 1, or 0. In this case, a set of two cutoff values is used to classify datasets comprising medical images into one of the three possible output values. Examples of sets of cutoff values may include {1%, 99%}, {2%, 98%}, {5%, 95%}, {10%, 90%}, {15%, 85%}, {20%, 80%}, {25%, 75%}, {30%, 70%}, {35%, 65%}, {40%, 60%}, and {45%, 55%}. Similarly, sets of n cutoff values may be used to classify datasets comprising medical images into one of n+1 possible output values, where n is any positive integer.

The trained algorithm may be trained with a plurality of independent training samples. Each of the independent training samples may comprise a dataset comprising medical images from a subject, associated datasets obtained by analyzing the medical images (e.g., labels or annotations), and one or more known output values corresponding to the dataset comprising medical images (e.g., the difficulty of reading the images, the time it took read the images, a clinical diagnosis, prognosis, absence, or treatment efficacy of a cancer of the subject). Independent training samples may comprise dataset comprising medical images, and associated datasets and outputs obtained or derived from a plurality of different subjects. Independent training samples may comprise dataset comprising medical images and associated datasets and outputs obtained at a plurality of different time points from the same subject (e.g., on a regular basis such as weekly, monthly, or annually). Independent training samples may be associated with presence of the cancer or disease (e.g., training samples comprising dataset comprising medical images, and associated datasets and outputs obtained or derived from a plurality of subjects known to have the cancer or disease). Independent training samples may be associated with absence of the cancer or disease (e.g., training samples comprising dataset comprising medical images, and associated datasets and outputs obtained or derived from a plurality of subjects who are known to not have a previous diagnosis of the cancer or who have received a negative test result for the cancer or disease).

The trained algorithm may be trained with at least about 50, at least about 100, at least about 250, at least about 500, at least about 1 thousand, at least about 5 thousand, at least about 10 thousand, at least about 15 thousand, at least about 20 thousand, at least about 25 thousand, at least about 30 thousand, at least about 35 thousand, at least about 40 thousand, at least about 45 thousand, at least about 50 thousand, at least about 100 thousand, at least about 150 thousand, at least about 200 thousand, at least about 250 thousand, at least about 300 thousand, at least about 350 thousand, at least about 400 thousand, at least about 450 thousand, or at least about 500 thousand independent training samples. The independent training samples may comprise dataset comprising medical images associated with presence of the disease (e.g., cancer) and/or dataset comprising medical images associated with absence of the disease (e.g., cancer). The trained algorithm may be trained with no more than about 500 thousand, no more than about 450 thousand, no more than about 400 thousand, no more than about 350 thousand, no more than about 300 thousand, no more than about 250 thousand, no more than about 200 thousand, no more than about 150 thousand, no more than about 100 thousand, no more than about 50 thousand, no more than about 25 thousand, no more than about 10 thousand, no more than about 5 thousand, no more than about 1 thousand, no more than about 500, no more than about 250, no more than about 100, or no more than about 50 independent training samples associated with presence of the disease (e.g., cancer). In some embodiments, the dataset comprising medical images is independent of samples used to train the trained algorithm.

The trained algorithm may be trained with a first number of independent training samples associated with presence of the disease (e.g., cancer) and a second number of independent training samples associated with absence of the disease (e.g., cancer). The first number of independent training samples associated with presence of the disease (e.g., cancer) may be no more than the second number of independent training samples associated with absence of the disease (e.g., cancer). The first number of independent training samples associated with presence of the disease (e.g., cancer) may be equal to the second number of independent training samples associated with absence of the disease (e.g., cancer). The first number of independent training samples associated with presence of the disease (e.g., cancer) may be greater than the second number of independent training samples associated with absence of the disease (e.g., cancer).

The trained algorithm may be configured to classify the medical images at an accuracy of at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or more; for at least about 50, at least about 100, at least about 250, at least about 500, at least about 1 thousand, at least about 5 thousand, at least about 10 thousand, at least about 15 thousand, at least about 20 thousand, at least about 25 thousand, at least about 30 thousand, at least about 35 thousand, at least about 40 thousand, at least about 45 thousand, at least about 50 thousand, at least about 100 thousand, at least about 150 thousand, at least about 200 thousand, at least about 250 thousand, at least about 300 thousand, at least about 350 thousand, at least about 400 thousand, at least about 450 thousand, or at least about 500 thousand independent test samples. The accuracy of classifying the medical images by the trained algorithm may be calculated as the percentage of independent test samples (e.g., images from subjects known to have the cancer or subjects with negative clinical test results for the cancer) that are correctly identified or classified as being normal or suspicious.

The trained algorithm may be configured to classify the medical images with a positive predictive value (PPV) of at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or more. The PPV of classifying the medical images using the trained algorithm may be calculated as the percentage of medical images identified or classified as being suspicious that correspond to subjects that truly have an abnormal condition (e.g., cancer).

The trained algorithm may be configured to classify the medical images with a negative predictive value (NPV) of at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or more. The NPV of classifying the medical images using the trained algorithm may be calculated as the percentage of medical images identified or classified as being normal that correspond to subjects that truly do not have an abnormal condition (e.g., cancer).

The trained algorithm may be configured to classify the medical images with a clinical sensitivity at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, at least about 99.1%, at least about 99.2%, at least about 99.3%, at least about 99.4%, at least about 99.5%, at least about 99.6%, at least about 99.7%, at least about 99.8%, at least about 99.9%, at least about 99.99%, at least about 99.999%, or more. The clinical sensitivity of classifying the medical images using the trained algorithm may be calculated as the percentage of medical images obtained from subjects known to have a condition (e.g., cancer) that are correctly identified or classified as being suspicious for the condition.

The trained algorithm may be configured to classify the medical images with a clinical specificity of at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, at least about 99.1%, at least about 99.2%, at least about 99.3%, at least about 99.4%, at least about 99.5%, at least about 99.6%, at least about 99.7%, at least about 99.8%, at least about 99.9%, at least about 99.99%, at least about 99.999%, or more. The clinical specificity of classifying the medical images using the trained algorithm may be calculated as the percentage of medical images obtained from subjects without a condition (e.g., subjects with negative clinical test results for cancer) that are correctly identified or classified as being normal for the condition.

The trained algorithm may be configured to classify the medical images with an Area-Under-Curve (AUC) of at least about 0.50, at least about 0.55, at least about 0.60, at least about 0.65, at least about 0.70, at least about 0.75, at least about 0.80, at least about 0.81, at least about 0.82, at least about 0.83, at least about 0.84, at least about 0.85, at least about 0.86, at least about 0.87, at least about 0.88, at least about 0.89, at least about 0.90, at least about 0.91, at least about 0.92, at least about 0.93, at least about 0.94, at least about 0.95, at least about 0.96, at least about 0.97, at least about 0.98, at least about 0.99, or more. The AUC may be calculated as an integral of the Receiver Operating Characteristic (ROC) curve (e.g., the area under the ROC curve) associated with the trained algorithm in classifying datasets comprising medical images as being normal or suspicious.

The trained algorithm may be adjusted or tuned to improve one or more of the performance, accuracy, PPV, NPV, clinical sensitivity, clinical specificity, or AUC of identifying the cancer. The trained algorithm may be adjusted or tuned by adjusting parameters of the trained algorithm (e.g., a set of cutoff values used to classify a dataset comprising medical images as described elsewhere herein, or parameters or weights of a neural network). The trained algorithm may be adjusted or tuned continuously during the training process or after the training process has completed.

After the trained algorithm is initially trained, a subset of the inputs may be identified as most influential or most important to be included for making high-quality classifications. For example, a subset of the plurality of features of the dataset comprising medical images may be identified as most influential or most important to be included for making high-quality classifications or identifications of cancer. The plurality of features of the dataset comprising medical images or a subset thereof may be ranked based on classification metrics indicative of each individual feature's influence or importance toward making high-quality classifications or identifications of cancer. Such metrics may be used to reduce, in some cases significantly, the number of input variables (e.g., predictor variables) that may be used to train the trained algorithm to a desired performance level (e.g., based on a desired minimum accuracy, PPV, NPV, clinical sensitivity, clinical specificity, AUC, or a combination thereof). For example, if training the trained algorithm with a plurality comprising several dozen or hundreds of input variables in the trained algorithm results in an accuracy of classification of more than 99%, then training the trained algorithm instead with only a selected subset of no more than about 5, no more than about 10, no more than about 15, no more than about 20, no more than about 25, no more than about 30, no more than about 35, no more than about 40, no more than about 45, no more than about 50, or no more than about 100 such most influential or most important input variables among the plurality can yield decreased but still acceptable accuracy of classification (e.g., at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99%). The subset may be selected by rank-ordering the entire plurality of input variables and selecting a predetermined number (e.g., no more than about 5, no more than about 10, no more than about 15, no more than about 20, no more than about 25, no more than about 30, no more than about 35, no more than about 40, no more than about 45, no more than about 50, or no more than about 100) of input variables with the best classification metrics.

Identifying or Monitoring a Cancer

After using a trained algorithm to process the dataset comprising a plurality of medical images of a location of a body of a subject to classify the image as normal, ambiguous, or suspicious, a cancer may be identified or monitored in the subject. The identification may be made based at least in part on the classification of the image as normal, ambiguous, or suspicious; a plurality of features extracted from the dataset comprising medical images; and/or clinical health data of the subject. The identification may be made by a radiologist, a plurality of radiologists, or a trained algorithm.

The cancer may be identified in the subject at an accuracy of at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or more. The accuracy of identifying the cancer may be calculated as the percentage of independent test subjects (e.g., subjects known to have the cancer or subjects with negative clinical test results for the cancer) that are correctly identified or classified as having or not having the cancer.

The cancer may be identified in the subject with a positive predictive value (PPV) of at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or more. The PPV of identifying the cancer may be calculated as the percentage of independent test subjects identified or classified as having cancer that correspond to subjects that truly have cancer.

The cancer may be identified in the subject with a negative predictive value (NPV) of at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or more. The NPV of identifying the cancer using the trained algorithm may be calculated as the percentage of independent test subjects identified or classified as not having cancer that correspond to subjects that truly do not have cancer.

The cancer may be identified in the subject with a clinical sensitivity of at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, at least about 99.1%, at least about 99.2%, at least about 99.3%, at least about 99.4%, at least about 99.5%, at least about 99.6%, at least about 99.7%, at least about 99.8%, at least about 99.9%, at least about 99.99%, at least about 99.999%, or more. The clinical sensitivity of identifying the cancer may be calculated as the percentage of independent test subjects associated with presence of the cancer (e.g., subjects known to have the cancer) that are correctly identified or classified as having cancer.

The cancer may be identified in the subject with a clinical specificity of at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, at least about 99.1%, at least about 99.2%, at least about 99.3%, at least about 99.4%, at least about 99.5%, at least about 99.6%, at least about 99.7%, at least about 99.8%, at least about 99.9%, at least about 99.99%, at least about 99.999%, or more. The clinical specificity of identifying the cancer may be calculated as the percentage of independent test subjects associated with absence of the cancer (e.g., subjects with negative clinical test results for the cancer) that are correctly identified or classified as not having cancer.

In some embodiments, the subject may be identified as being at risk of a cancer. After identifying the subject as being at risk of a cancer, a clinical intervention for the subject may be selected based at least in part on the cancer for which the subject is identified as being at risk. In some embodiments, the clinical intervention is selected from a plurality of clinical interventions (e.g., clinically indicated for different types of cancer).

In some embodiments, the trained algorithm may determine that the subject is at risk of a cancer of at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or more.

The trained algorithm may determine that the subject is at risk of a cancer at an accuracy of at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, at least about 99.1%, at least about 99.2%, at least about 99.3%, at least about 99.4%, at least about 99.5%, at least about 99.6%, at least about 99.7%, at least about 99.8%, at least about 99.9%, at least about 99.99%, at least about 99.999%, or more.

Upon identifying the subject as having the cancer, the subject may be optionally provided with a therapeutic intervention (e.g., prescribing an appropriate course of treatment to treat the cancer of the subject). The therapeutic intervention may comprise a prescription of an effective dose of a drug, a further testing or evaluation of the cancer, a further monitoring of the cancer, or a combination thereof. If the subject is currently being treated for the cancer with a course of treatment, the therapeutic intervention may comprise a subsequent different course of treatment (e.g., to increase treatment efficacy due to non-efficacy of the current course of treatment).

The therapeutic intervention may comprise recommending the subject for a secondary clinical test to confirm a diagnosis of the cancer. This secondary clinical test may comprise an imaging test, a blood test, a computed tomography (CT) scan, a magnetic resonance imaging (MRI) scan, an ultrasound scan, a chest X-ray, a positron emission tomography (PET) scan, a PET-CT scan, or any combination thereof.

The classification of the image as normal, ambiguous, or suspicious; a plurality of features extracted from the dataset comprising medical images; and/or clinical health data of the subject may be assessed over a duration of time to monitor a patient (e.g., subject who has cancer or who is being treated for cancer). In some cases, the classification of the medical images of the patient may change during the course of treatment. For example, the features of the dataset of a patient with decreasing risk of the cancer due to an effective treatment may shift toward the profile or distribution of a healthy subject (e.g., a subject without cancer). Conversely, for example, the features of the dataset of a patient with increasing risk of the cancer due to an ineffective treatment may shift toward the profile or distribution of a subject with higher risk of the cancer or a more advanced cancer.

The cancer of the subject may be monitored by monitoring a course of treatment for treating the cancer of the subject. The monitoring may comprise assessing the cancer of the subject at two or more time points. The assessing may be based at least on the classification of the image as normal, ambiguous, or suspicious; a plurality of features extracted from the dataset comprising medical images; and/or clinical health data of the subject determined at each of the two or more time points.

In some embodiments, a difference in the classification of the image as normal, ambiguous, or suspicious; a plurality of features extracted from the dataset comprising medical images; and/or clinical health data of the subject determined between the two or more time points may be indicative of one or more clinical indications, such as (i) a diagnosis of the cancer of the subject, (ii) a prognosis of the cancer of the subject, (iii) an increased risk of the cancer of the subject, (iv) a decreased risk of the cancer of the subject, (v) an efficacy of the course of treatment for treating the cancer of the subject, and (vi) a non-efficacy of the course of treatment for treating the cancer of the subject.

In some embodiments, a difference in the classification of the image as normal, ambiguous, or suspicious; a plurality of features extracted from the dataset comprising medical images; and/or clinical health data of the subject determined between the two or more time points may be indicative of a diagnosis of the cancer of the subject. For example, if the cancer was not detected in the subject at an earlier time point but was detected in the subject at a later time point, then the difference is indicative of a diagnosis of the cancer of the subject. A clinical action or decision may be made based on this indication of diagnosis of the cancer of the subject, such as, for example, prescribing a new therapeutic intervention for the subject. The clinical action or decision may comprise recommending the subject for a secondary clinical test to confirm the diagnosis of the cancer. This secondary clinical test may comprise an imaging test, a blood test, a computed tomography (CT) scan, a magnetic resonance imaging (MRI) scan, an ultrasound scan, a chest X-ray, a positron emission tomography (PET) scan, a PET-CT scan, or any combination thereof.

In some embodiments, a difference in the classification of the image as normal, ambiguous, or suspicious; a plurality of features extracted from the dataset comprising medical images; and/or clinical health data of the subject determined between the two or more time points may be indicative of a prognosis of the cancer of the subject.

In some embodiments, a difference in the classification of the image as normal, ambiguous, or suspicious; a plurality of features extracted from the dataset comprising medical images; and/or clinical health data of the subject determined between the two or more time points may be indicative of the subject having an increased risk of the cancer. For example, if the cancer was detected in the subject both at an earlier time point and at a later time point, and if the difference is a positive difference (e.g., an increase from the earlier time point to the later time point), then the difference may be indicative of the subject having an increased risk of the cancer. A clinical action or decision may be made based on this indication of the increased risk of the cancer, e.g., prescribing a new therapeutic intervention or switching therapeutic interventions (e.g., ending a current treatment and prescribing a new treatment) for the subject. The clinical action or decision may comprise recommending the subject for a secondary clinical test to confirm the increased risk of the cancer. This secondary clinical test may comprise an imaging test, a blood test, a computed tomography (CT) scan, a magnetic resonance imaging (MRI) scan, an ultrasound scan, a chest X-ray, a positron emission tomography (PET) scan, a PET-CT scan, or any combination thereof.

In some embodiments, a difference in the classification of the image as normal, ambiguous, or suspicious; a plurality of features extracted from the dataset comprising medical images; and/or clinical health data of the subject determined between the two or more time points may be indicative of the subject having a decreased risk of the cancer. For example, if the cancer was detected in the subject both at an earlier time point and at a later time point, and if the difference is a negative difference (e.g., a decrease from the earlier time point to the later time point), then the difference may be indicative of the subject having a decreased risk of the cancer. A clinical action or decision may be made based on this indication of the decreased risk of the cancer (e.g., continuing or ending a current therapeutic intervention) for the subject. The clinical action or decision may comprise recommending the subject for a secondary clinical test to confirm the decreased risk of the cancer. This secondary clinical test may comprise an imaging test, a blood test, a computed tomography (CT) scan, a magnetic resonance imaging (MRI) scan, an ultrasound scan, a chest X-ray, a positron emission tomography (PET) scan, a PET-CT scan, or any combination thereof.

In some embodiments, a difference in the classification of the image as normal, ambiguous, or suspicious; a plurality of features extracted from the dataset comprising medical images; and/or clinical health data of the subject determined between the two or more time points may be indicative of an efficacy of the course of treatment for treating the cancer of the subject. For example, if the cancer was detected in the subject at an earlier time point but was not detected in the subject at a later time point, then the difference may be indicative of an efficacy of the course of treatment for treating the cancer of the subject. A clinical action or decision may be made based on this indication of the efficacy of the course of treatment for treating the cancer of the subject, e.g., continuing or ending a current therapeutic intervention for the subject. The clinical action or decision may comprise recommending the subject for a secondary clinical test to confirm the efficacy of the course of treatment for treating the cancer. This secondary clinical test may comprise an imaging test, a blood test, a computed tomography (CT) scan, a magnetic resonance imaging (MRI) scan, an ultrasound scan, a chest X-ray, a positron emission tomography (PET) scan, a PET-CT scan, or any combination thereof.

In some embodiments, a difference in the classification of the image as normal, ambiguous, or suspicious; a plurality of features extracted from the dataset comprising medical images; and/or clinical health data of the subject determined between the two or more time points may be indicative of a non-efficacy of the course of treatment for treating the cancer of the subject. For example, if the cancer was detected in the subject both at an earlier time point and at a later time point, and if the difference is a positive or zero difference (e.g., increased or remained at a constant level from the earlier time point to the later time point), and if an efficacious treatment was indicated at an earlier time point, then the difference may be indicative of a non-efficacy of the course of treatment for treating the cancer of the subject. A clinical action or decision may be made based on this indication of the non-efficacy of the course of treatment for treating the cancer of the subject, e.g., ending a current therapeutic intervention and/or switching to (e.g., prescribing) a different new therapeutic intervention for the subject. The clinical action or decision may comprise recommending the subject for a secondary clinical test to confirm the non-efficacy of the course of treatment for treating the cancer. This secondary clinical test may comprise an imaging test, a blood test, a computed tomography (CT) scan, a magnetic resonance imaging (MRI) scan, an ultrasound scan, a chest X-ray, a positron emission tomography (PET) scan, a PET-CT scan, or any combination thereof.

Outputting a Report of the Disease

After the cancer is identified or an increased risk of the disease or cancer is monitored in the subject, a report may be electronically outputted that is indicative of (e.g., identifies or provides an indication of) the disease or cancer of the subject. The subject may not display a disease or cancer (e.g., is asymptomatic of the disease or cancer such as a complication). The report may be presented on a graphical user interface (GUI) of an electronic device of a user. The user may be the subject, a caretaker, a physician, a nurse, or another health care worker.

The report may include one or more clinical indications such as (i) a diagnosis of the cancer of the subject, (ii) a prognosis of the disease or cancer of the subject, (iii) an increased risk of the disease or cancer of the subject, (iv) a decreased risk of the disease or cancer of the subject, (v) an efficacy of the course of treatment for treating the disease or cancer of the subject, (vi) a non-efficacy of the course of treatment for treating the disease or cancer of the subject, (vii) a location and/or a level of suspicion of the disease or cancer, and (viii) an efficacy measure of a proposed course of diagnosis of the disease or cancer. The report may include one or more clinical actions or decisions made based on these one or more clinical indications. Such clinical actions or decisions may be directed to therapeutic interventions, or further clinical assessment or testing of the disease or cancer of the subject.

For example, a clinical indication of a diagnosis of the disease or cancer of the subject may be accompanied with a clinical action of prescribing a new therapeutic intervention for the subject. As another example, a clinical indication of an increased risk of the disease or cancer of the subject may be accompanied with a clinical action of prescribing a new therapeutic intervention or switching therapeutic interventions (e.g., ending a current treatment and prescribing a new treatment) for the subject. As another example, a clinical indication of a decreased risk of the disease or cancer of the subject may be accompanied with a clinical action of continuing or ending a current therapeutic intervention for the subject. As another example, a clinical indication of an efficacy of the course of treatment for treating the disease or cancer of the subject may be accompanied with a clinical action of continuing or ending a current therapeutic intervention for the subject. As another example, a clinical indication of a non-efficacy of the course of treatment for treating the disease or cancer of the subject may be accompanied with a clinical action of ending a current therapeutic intervention and/or switching to (e.g., prescribing) a different new therapeutic intervention for the subject. As another example, a clinical indication of a location of disease or cancer may be accompanied with a clinical action of prescribing a new diagnostic test, especially any particular parameters of that test that may be targeted for the indication.

Computer Systems

Figure 4:
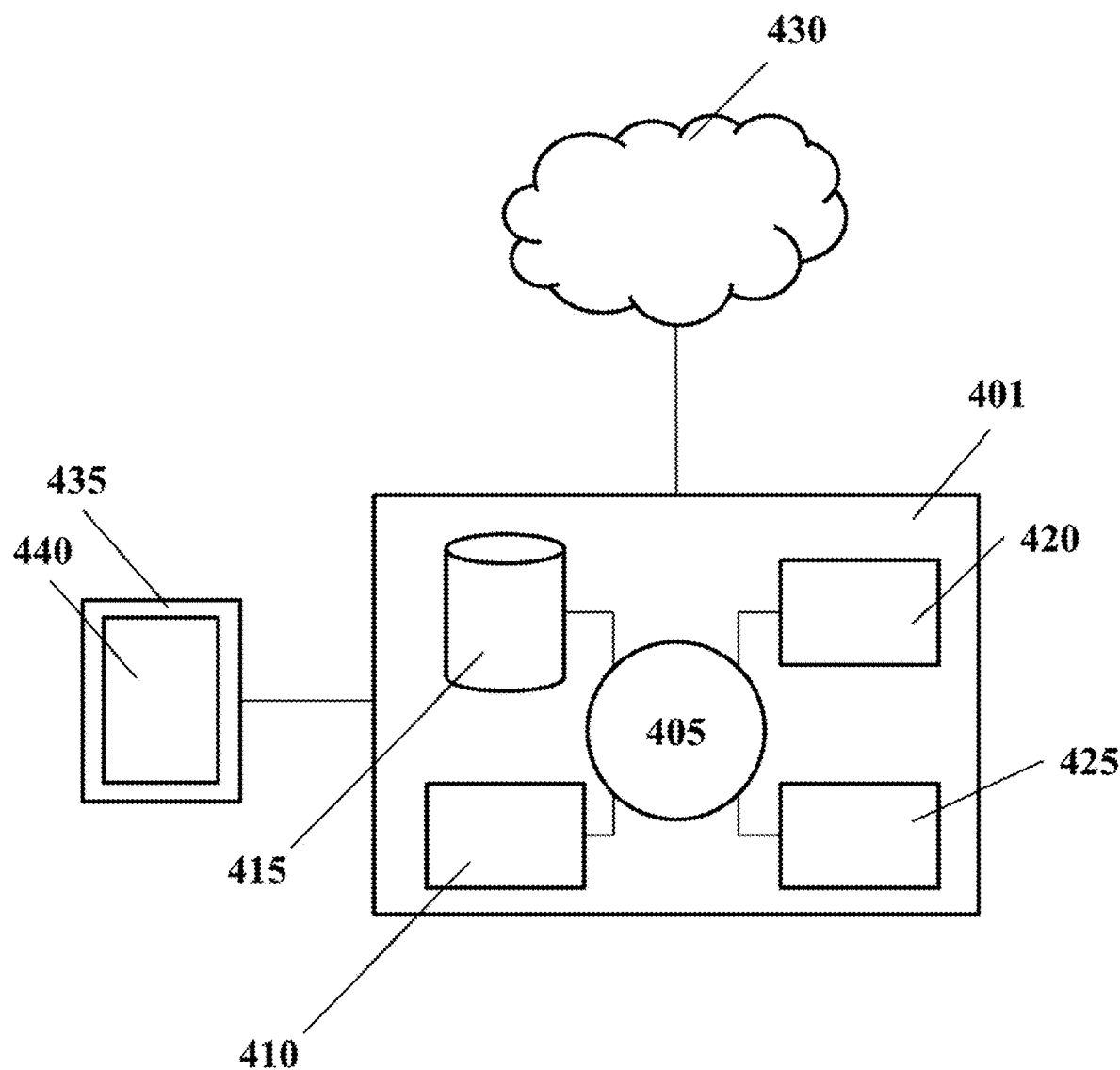
FIG. 4 illustrates a computer system that is programmed or otherwise configured to implement methods provided herein.

The present disclosure provides computer systems that are programmed to implement methods of the disclosure. FIG. 4 shows a computer system 401 that is programmed or otherwise configured to, for example, train and test a trained algorithm; use the trained algorithm to process medical images to classify the image as normal, ambiguous, or suspicious; identify or monitor a cancer of the subject; and electronically output a report that indicative of the cancer of the subject.

The computer system 401 can regulate various aspects of analysis, calculation, and generation of the present disclosure, such as, for example, training and testing a trained algorithm; using the trained algorithm to process medical images to classify the image as normal, ambiguous, or suspicious; identifying or monitoring a cancer of the subject; and electronically outputting a report that indicative of the cancer of the subject. The computer system 401 can be an electronic device of a user or a computer system that is remotely located with respect to the electronic device. The electronic device can be a mobile electronic device.

The computer system 401 includes a central processing unit (CPU, also "processor" and "computer processor" herein) 405, which can be a single core or multi core processor, or a plurality of processors for parallel processing. The computer system 401 also includes memory or memory location 410 (e.g., random-access memory, read-only memory, flash memory), electronic storage unit 415 (e.g., hard disk), communication interface 420 (e.g., network adapter) for communicating with one or more other systems, and peripheral devices 425, such as cache, other memory, data storage and/or electronic display adapters. The memory 410, storage unit 415, interface 420 and peripheral devices 425 are in communication with the CPU 405 through a communication bus (solid lines), such as a motherboard. The storage unit 415 can be a data storage unit (or data repository) for storing data. The computer system 401 can be operatively coupled to a computer network ("network") 430 with the aid of the communication interface 420. The network 430 can be the Internet, an internet and/or extranet, or an intranet and/or extranet that is in communication with the Internet.

The network 430 in some cases is a telecommunication and/or data network. The network 430 can include one or more computer servers, which can enable distributed computing, such as cloud computing. For example, one or more computer servers may enable cloud computing over the network 430 ("the cloud") to perform various aspects of analysis, calculation, and generation of the present disclosure, such as, for example, training and testing a trained algorithm; using the trained algorithm to process medical images to classify the image as normal, ambiguous, or suspicious; identifying or monitoring a cancer of the subject; and electronically outputting a report that indicative of the cancer of the subject. Such cloud computing may be provided by cloud computing platforms such as, for example, Amazon Web Services (AWS), Microsoft Azure, Google Cloud Platform, and IBM cloud. The network 430, in some cases with the aid of the computer system 401, can implement a peer-to-peer network, which may enable devices coupled to the computer system 401 to behave as a client or a server.

The CPU 405 may comprise one or more computer processors and/or one or more graphics processing units (GPUs). The CPU 405 can execute a sequence of machine-readable instructions, which can be embodied in a program or software. The instructions may be stored in a memory location, such as the memory 410. The instructions can be directed to the CPU 405, which can subsequently program or otherwise configure the CPU 405 to implement methods of the present disclosure. Examples of operations performed by the CPU 405 can include fetch, decode, execute, and writeback.

The CPU 405 can be part of a circuit, such as an integrated circuit. One or more other components of the system 401 can be included in the circuit. In some cases, the circuit is an application specific integrated circuit (ASIC).

The storage unit 415 can store files, such as drivers, libraries and saved programs. The storage unit 415 can store user data, e.g., user preferences and user programs. The computer system 401 in some cases can include one or more additional data storage units that are external to the computer system 401, such as located on a remote server that is in communication with the computer system 401 through an intranet or the Internet.

The computer system 401 can communicate with one or more remote computer systems through the network 430. For instance, the computer system 401 can communicate with a remote computer system of a user. Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 401 via the network 430.

Methods as described herein can be implemented by way of machine (e.g., computer processor) executable code stored on an electronic storage location of the computer system 401, such as, for example, on the memory 410 or electronic storage unit 415. The machine executable or machine readable code can be provided in the form of software. During use, the code can be executed by the processor 405. In some cases, the code can be retrieved from the storage unit 415 and stored on the memory 410 for ready access by the processor 405. In some situations, the electronic storage unit 415 can be precluded, and machine-executable instructions are stored on memory 410.

The code can be pre-compiled and configured for use with a machine having a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 401, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 401 can include or be in communication with an electronic display 435 that comprises a user interface (UI) 440 for providing, for example, a visual display indicative of training and testing of a trained algorithm; a visual display of image data indicative of a classification as normal, ambiguous, or suspicious; an identification of a subject as having a cancer; or an electronic report (e.g., diagnostic or radiological report) indicative of the cancer of the subject. Examples of UIs include, without limitation, a graphical user interface (GUI) and web-based user interface.

Methods and systems of the present disclosure can be implemented by way of one or more algorithms. An algorithm can be implemented by way of software upon execution by the central processing unit 405. The algorithm can, for example, train and test a trained algorithm; use the trained algorithm to process medical images to classify the image as normal, ambiguous, or suspicious; identify or monitor a cancer of the subject; and electronically output a report that indicative of the cancer of the subject.

EXAMPLES

Example 1—Improving Patient Care with Real-Time Radiology

Using systems and methods of the present disclosure, a real-time radiology screening and diagnostic workflow was performed on a plurality of patients. As an example, on the first day of the real-time radiology clinic, a patient received immediate results for a normal case, which resulted in the patient feeling relieved and reassured.

As another example, on the next day of the real-time radiology clinic, another patient received a suspicious finding during a screening, and had a diagnostic follow-up performed for the suspicious finding within three hours. The patient was told by the radiologist that her findings were benign and that she is not suspected of having cancer. The patient was very relieved and happy to avoid the anxiety of waiting for a final diagnostic result. On average, such a process may take anywhere from 2 to 8 weeks in the U.S. Even in particular clinics with expedited workflows, the process may take 1 to 2 weeks without the assistance of real-time radiology.

Figure 5:
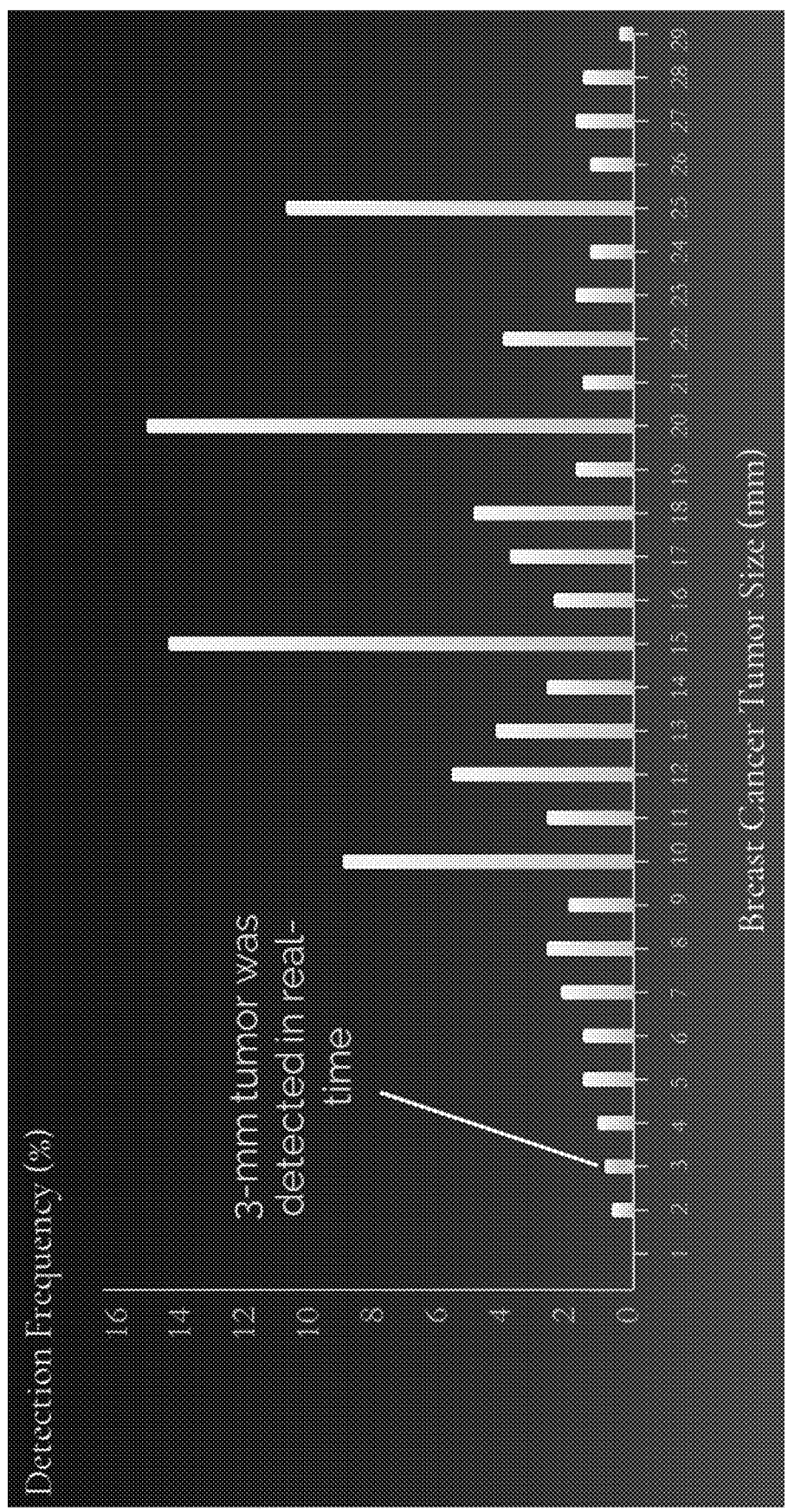
FIG. 5 shows an example plot of detection frequency of breast cancer tumors of various sizes (ranging from 2 mm to 29 mm) that are detected using a real-time radiology system, in accordance with disclosed embodiments.

As another example, on another day of the real-time radiology clinic, the AI-based real-time radiology system detected a 3-mm breast cancer tumor, which was confirmed 5 days later by biopsy to be a cancer. FIG. 5 shows an example plot of detection frequency of breast cancer tumors of various sizes (ranging from 2 mm to 29 mm) that are detected by radiologists, in accordance with disclosed embodiments. The real-time radiology system may provide life-saving clinical impact, by reducing the time to treatment. The cancer may continue to grow until this patient receives her next screening or diagnostic procedure, at which time removal and treatment may have been more life threatening, painful, expensive, and have a lower success rate.

As another example, of the real-time radiology clinic, a patient received a diagnostic follow-up procedure for a suspicious finding within 1 hour. A biopsy was needed, but was completed the next business day because the patient was on aspirin. The biopsy confirmed the cancer that was detected by the real-time radiology. The radiology work-up period was reduced from 8 business days to 1 day, and the time to diagnosis was reduced from 1 month to 1 week.

The clinical impact of the real-time radiology system can be measured by screening mammography metrics, such as PPV1 and callback rate. The PPV1 generally refers to the percentage of examinations with an abnormal initial interpretation by a radiologist that result in a tissue diagnosis of cancer within 1 year. The callback rate generally refers to the percentage of examinations with an abnormal initial interpretation (e.g., "recall rate"). During a 6-week span, a real-time radiology clinic processed 796 patient cases using AI-based analysis, of which 94 cases were flagged to be read by radiologists in real time. A total of 4 cases were diagnosed as cancer, of which 3 cases were confirmed as cancer (e.g., by biopsy).

Figure 6:
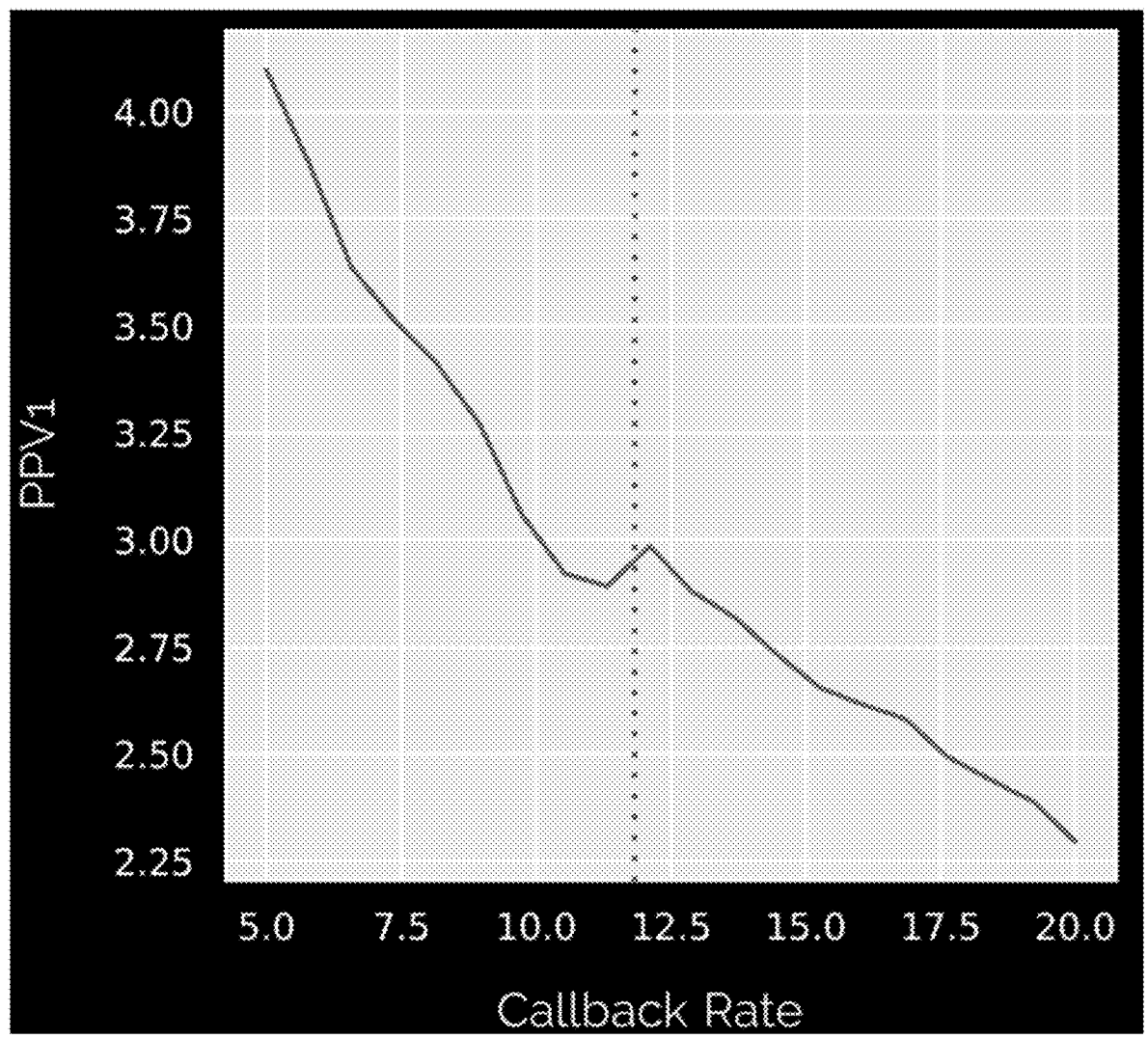
FIG. 6 shows an example plot of positive predictive values from screening mammography (PPV1) versus callback rate, in accordance with disclosed embodiments.

FIG. 6 shows an example plot of positive predictive values from screening mammography (PPV1) versus callback rate, in accordance with disclosed embodiments. The prospective study resulted in a callback rate of 11.8% with a PPV1 of 3.2%. In comparison, a median radiologist has a callback rate of 11.6% with a PPV1 of 4.4%.

Figure 7:
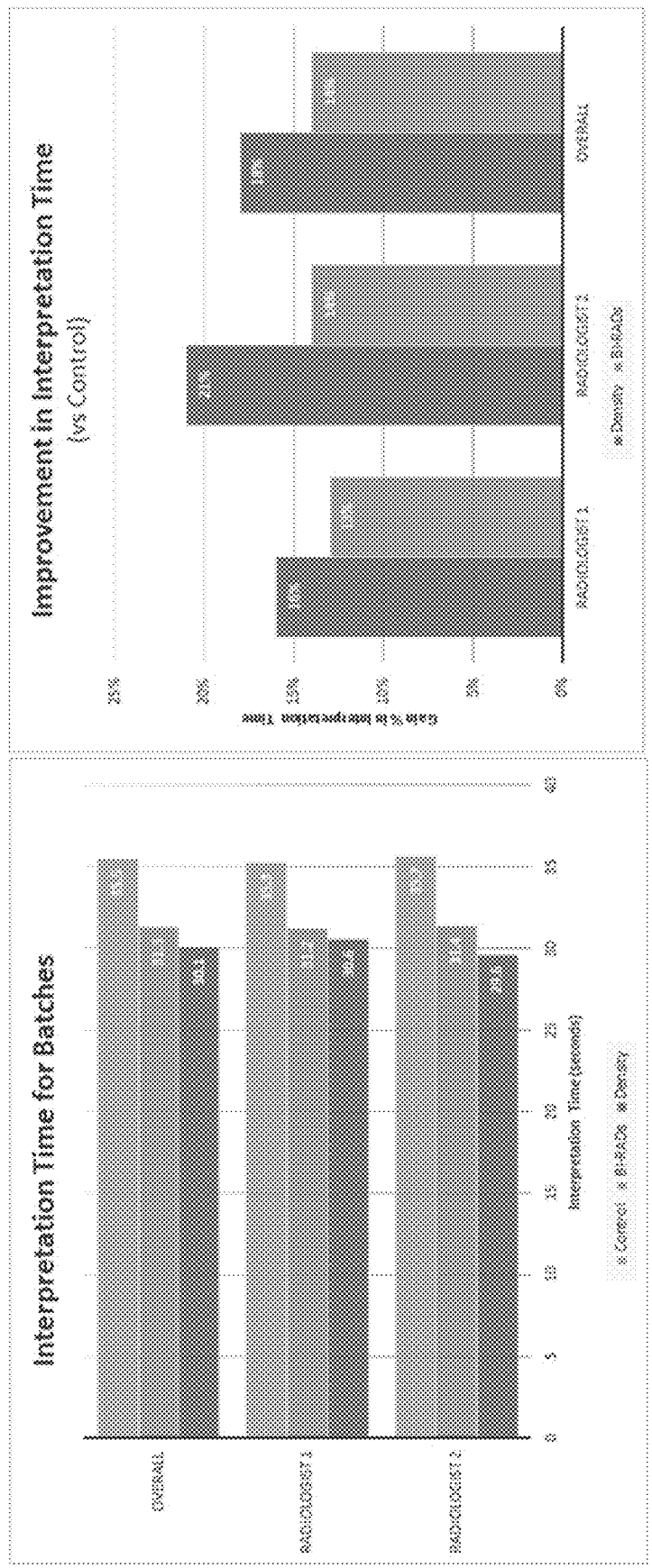
FIG. 7 shows an example plot comparing the interpretation time for batches (including control, BI-RADs, and density) (left) and the percentage improvement in interpretation time versus controls (right), across a first set of radiologist, a second set of radiologists, and the overall total set of radiologists, in accordance with disclosed embodiments.

FIG. 7 shows an example plot comparing the interpretation time for reading images in AI-sorted batches (including Bi-RADS Assessment, and density) (left) and the percentage improvement in interpretation time versus controls who read randomly shuffled batches (right), across a first set of radiologist, a second set of radiologists, and the overall total set of radiologists, in accordance with disclosed embodiments. This figure shows that AI-powered workflows can improve radiologist productivity to a statistically significant extent (ranging from about 13% to 21%).

Example 2—Classification of Suspicious Findings in Screening Mammography with Deep Neural Networks Deep learning may be applied to a variety of computer vision and image processing applications. For example, deep learning may be used to automatically learn image features relevant to a given task and may be used for various tasks from classification to detection to segmentation. Computational models based on deep neural networks (DNNs) may be developed and used in radiology applications, such as screening mammography, to identify suspicious, potentially abnormal, or high-risk lesions and increase radiologist productivity. In some cases, deep learning models are able to match or even surpass human-level performance. In addition, deep learning may be used to help raise the performance of general radiologists to be closer to that of breast imaging specialists. For example, general radiologists generally have poorer cancer detection rates and much higher recall rates compared to fellowship-trained breast radiologists.

Deep learning can be used to perform interpretation of screening mammography, including distinguishing between malignant and benign findings. A DNN model is trained for this task to identify missed cancers or reduce the false positive callbacks, particularly for non-expert readers.

The DNN model was trained using the publicly accessible Digital Database for Screening Mammography (DDSM) dataset (eng.usf.edu/cvprg/Mammography/Database.html). DDSM includes 2,620 studies with over 10,000 digitized scanned film mammography images. The images were evenly split between normal mammograms and those with suspicious findings. The normal mammograms were confirmed through a four-year follow-up of the patient. The suspicious findings were further split between biopsy-proven benign findings (51%) and biopsy-proven malignant findings (49%). All cases with obviously benign findings that are not followed up by biopsy as part of routine clinical care were excluded from the dataset. As a result, distinguishing between benign and malignant findings may be more difficult for this dataset than in a typical clinical mammography screening scenario.

The DDSM dataset was divided into subsets including a training dataset, a validation dataset, and a testing dataset. Using the training dataset, a DNN was trained to distinguish malignant findings from benign findings or a normal region of the breast. The datasets included annotations pointing out the locations of tumors in the images, which may be critical in guiding the deep learning process.

Figure 8:
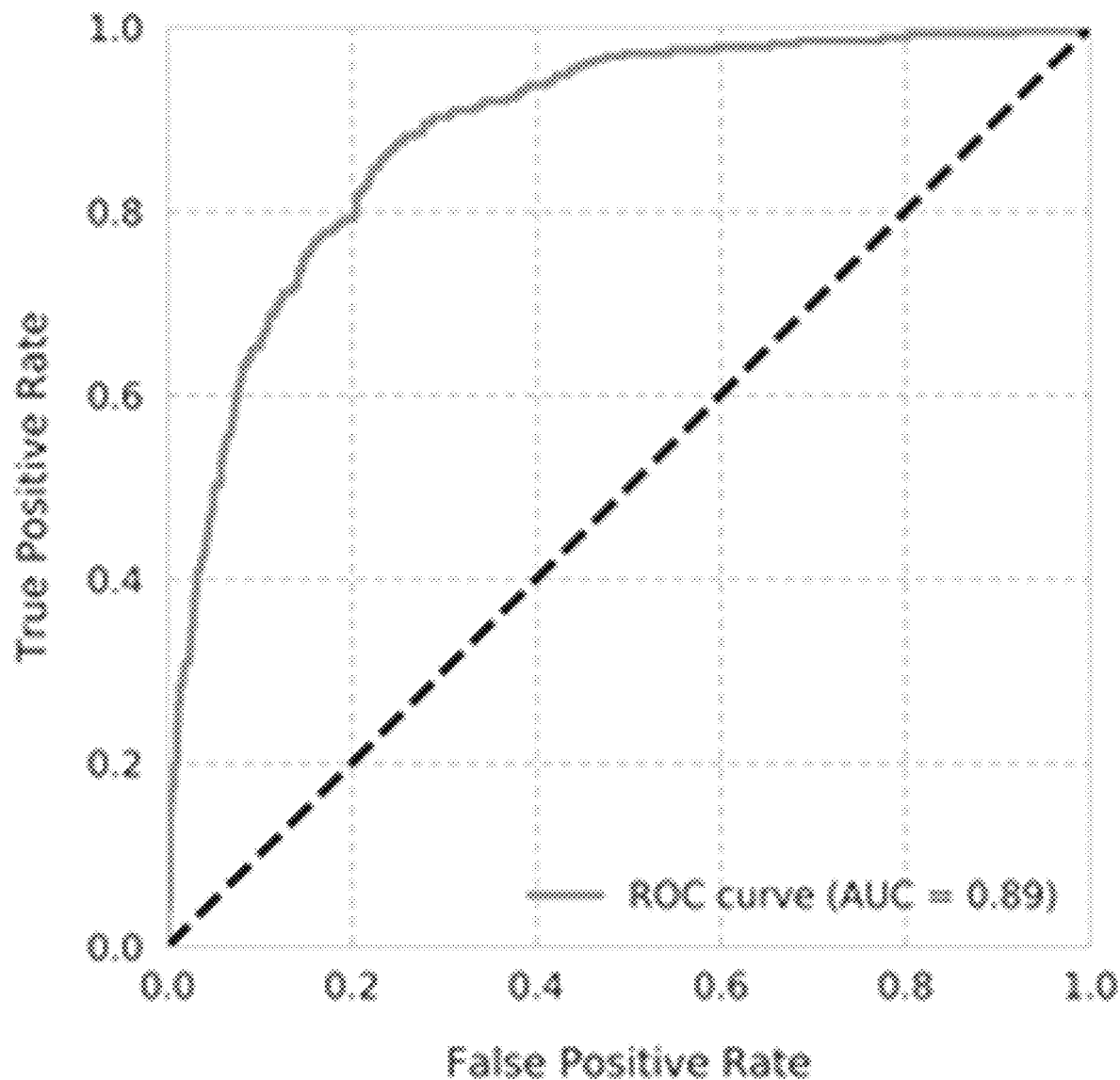
FIG. 8 shows a receiver operating characteristic (ROC) curve indicating the performance of the DNN on a binary classification task as evaluated on a testing dataset, in accordance with disclosed embodiments.

The performance of the DNN on this binary classification task was evaluated on the testing dataset through the use of a receiver operating characteristic (ROC) curve (as shown in FIG. 8). The DNN model was used to distinguish between malignant and benign findings with high accuracy, as indicated by the area under the ROC curve (AUC) of 0.89. In comparison, expert radiologists are typically able to achieve a sensitivity of 84.4% and a specificity of 90.8% for the task of cancer detection for screening mammography. The DNN model was used to distinguish between malignant and benign findings with a sensitivity of 79.2% and a specificity of 80.0% with the more challenging cases found in the DDSM dataset. The performance gap relative to expert radiologists is in part due to the relatively small size of the dataset, and may be mitigated by incorporating larger training datasets. Further, the DNN model may still be configured to outperform general radiologists in accuracy, sensitivity, specificity, AUC, positive predictive value, negative predictive value, or a combination thereof.

A highly accurate DNN model was developed by training on a limited public benchmark dataset. While the dataset is perhaps more difficult than in the clinical setting, the DNN model was able to distinguish between malignant and benign findings with nearly human-level performance.

A similar DNN model may be trained using the clinical mammography dataset of the Joanne Knight Breast Health Center in St. Louis, in partnership with Washington University in St. Louis. This dataset includes a large medical records database comprising more than 100 thousand patients, including 4 thousand biopsy-confirmed cancer patients, and over 400 thousand imaging sessions comprising 1.5 million images. The dataset may be manually or automatically labeled (e.g., by building annotations) to optimize the deep learning process. Since the performance of DNNs improves significantly with the size of the training dataset, this uniquely massive and rich dataset may lead to a DNN model having dramatic increases in sensitivity and specificity as compared to the DNN model trained on the DDSM data. Such highly accurate DNN models offer opportunities for transformative improvements in breast cancer screening, enabling all women to receive access to specialist-level care.

Example 3—Artificial Intelligence (AI)-Powered Radiology Clinics for Early Cancer Detection Introduction Breast cancer is the most widespread cancer in women in the U.S., with over 250 thousand new diagnoses in 2017 alone. About 1 in 8 women will be diagnosed with breast cancer at some point during their lives. Despite improvements in treatment, over 40 thousand women die every year in the U.S. from breast cancer. Substantial progress has made in reducing breast cancer mortality (39% lower since 1989) in part due to the widespread adoption of screening mammography. Breast cancer screening can help identify early-stage cancers, which have much better prognoses and lower treatment costs as compared to late-stage cancers. This difference can be substantial: women with localized breast cancer have a 5-year survival rate of nearly 99%, while women with metastatic breast cancer have a 5-year survival rate of 27%.

Despite these demonstrated benefits, only about half of women currently obtain mammograms at the rate recommended by the American College of Radiology. This low mammography utilization may result in a significant burden to patients and to healthcare systems in the form of worse outcomes and higher costs. Adoption rates for screening mammography are hindered, in part, by poor patient experience, such as long delays in obtaining an appointment, unclear pricing, long wait times to receive exam results, and confusing reports. Further, problems arising from a lack of transparency in pricing are exacerbated by large variations in costs among providers. Similarly, delivery times for receiving exam results are inconsistent among providers.

In addition, significant variation in radiologist performance results in patients experiencing very different standards of care depending on location and income. For example, cancer detection rates are more than twice as high for radiologists in the 90th percentile compared with radiologists in the 10th percentile. False positive rates (e.g., the rate at which healthy patients are mistakenly recalled for follow-up exams) have even larger differences between these two groups. Aggregated across all screening exams done in the U.S., about 96% of patients who are called back are false positives. Given the huge societal and personal burden of cancer, combined with the often poor patient experience, inconsistent screening performance, and large cost variations, AI-based or AI-assisted screening approaches can be developed to significantly improve this clinical accuracy of mammography screening.

Innovations in artificial intelligence and software can be leveraged toward achieving significant improvements to health outcomes, including early, accurate detection of cancer. These improvements may affect one or more steps within the patient journey—from cost transparency, appointment scheduling, patient care, radiology workflow, diagnostic accuracy, results delivery, to follow-up. An AI-powered network of imaging centers may be developed to deliver high-quality service, timeliness, accuracy, and cost effectiveness. At such clinics, women may schedule a mammogram instantly, and receive a diagnosis of cancer within a single visit before they leave. The AI-powered clinics may enable the transformation of a traditional two-visit screening-diagnostic paradigm into a single visit, by using "real-time radiology" methods and systems of the present disclosure. Artificial intelligence may be used to customize the clinical workflow for each patient using a triage engine and to tailor how screening exams are read to significantly enhance radiologist accuracy (e.g., by reducing radiologist fatigue), thereby improving the accuracy of cancer detection. Additional improvements to the screening/diagnosis process can be achieved using AI-based or AI-assisted approaches, such as patient scheduling, improving screening guideline adherence through customer outreach, and the timeliness of report delivery with patient-facing applications. A self-improving system may use AI to build better clinics that generate the data to improve the AI-based system.

A key component of creating the AI-powered radiology network is driving growth through patient acquisition. While other components of the system may streamline processes of a radiology workflow and provide patients with an improved and streamlined experience, patient recruitment and enrollment is important to collect sufficient data to train the AI-powered systems for high performance.

Further, AI-powered clinics may reduce obstacles to screening mammography by improving the patient experience before the patients arrive at a clinic. This may include addressing two key barriers that limit adoption: (1) concerns about the cost of the exam and (2) lack of awareness about conveniently located clinics. When price and availability are completely opaque, as with conventional clinics, significant variations in price and service may exist, thereby creating a barrier to patients' scheduling of appointments.

An AI-based user application may be developed to streamline the scheduling process and offer transparency for patients. The application may be configured to provide users with a map of clinics that accept their insurance as well as available times for appointments. For those with health insurance, screening mammograms, both 2D and 3D, are at no out-of-pocket cost. This, along with any potential costs that might be incurred, may be clearly indicated to the patient at the time of scheduling. Guarantees about the timeliness of exam results may also be presented to the patient, which addresses a potential source of anxiety for patients that may make them less likely to schedule an appointment.

The application may be configured to confirm the patient's insurance and request the work order from the primary care provider (PCP), if necessary, during the scheduling process. The application may be configured to receive user input of pre-exam forms in order to more efficiently process patients during their visit to the clinic. If the patient has any remaining forms remaining to complete prior to the exam, she may be provided with a device at the time of check-in to the clinic, to complete the remaining forms. The application may be configured to facilitate electronic entry of these forms to reduce or eliminate the time-consuming and error-prone task of manually transcribing paper forms, as done under the current standard of care. By facilitating the user entry of paperwork prior to the exam date, the application enables the patient to have a more streamlined experience, and less time and resources are devoted to administrative tasks on-site.

The patient's previously acquired mammograms may also be obtained prior to the exam. For images acquired at partnering clinics, this process may happen transparently to the patient. By obtaining the prior images before the visit, a potential bottleneck to immediate review of newly acquired images may be eliminated.

After scheduling an appointment, the application may be configured to provide the patient with reminders about the upcoming exam in order to increase attendance. The application may also be configured to provide the patient with information about the exam procedures ahead of time, in order to minimize anxiety and to reduce time spent explaining the procedure within the exam room. Further, to develop relationships with primary care physicians (PCPs), referring physicians may be able to confirm that their patients have scheduled a mammography appointment. This will allow doctors to assess compliance and to encourage patients who do not sign up for an appointment in a timely manner following their recommendations.

Real-Time Radiology System

The conventional breast cancer screening paradigm may include significant delays that introduce anxiety of patients. This may reduce the number of women who elect to obtain this preventative care and put them at risk for discovering cancer later when it is more difficult to treat and more deadly. A typical patient may visit a clinic for a screening mammogram, spend about half an hour at the clinic, then leave. She may then wait up to 30 days for a phone call or letter to receive the news that there is a suspicious abnormality on the screening mammogram and that she should schedule a follow-up diagnostic appointment. Next, the patient may wait another week for that appointment, during which she may receive additional imaging to determine if a biopsy is required.

The current paradigm is motivated by the volume of patients that are screened at larger practices (e.g., more than 100 patients per day). These imaging centers typically have at least a 1-2 day backlog of screening exams that needs to be read before the radiologists can process the screening mammograms that were performed on a given day. If any of those cases were to require a diagnostic work-up, that exam often cannot be done right away because of the high variance in the length of diagnostic exams (e.g., ranging from 20 to 120 minutes. Scheduling does not take this into account, leading to prolonged wait times for patients and inefficient workflows for technologists.

Patients who received immediate real-time reading of their screening mammograms may experience significantly less anxiety than those who had not after 3 weeks. In contrast, women who received false positives at screening (normal cases flagged as suspicious) but received an immediate reading experienced nearly the same level of anxiety as women with normal mammograms. Most of these women did not perceive themselves as having an abnormal screen. Those that do, however, tend to seek more medical attention for breast-related concerns and other medical issues. Further, if women know they may leave the mammography clinic with the results of their mammograms, they may be more satisfied with the screening process and may be more likely to follow future screening recommendations. Such increased patient satisfaction may improve member retention among health plans. Additionally, immediate reading of suspicious cases may decrease the time to breast cancer diagnosis, thereby improving patient care and outcomes.

In some cases, clinics are able to offer real-time service by restricting volume. Such clinics may schedule only a few patients at any given time so that, in case the need arises, the patients can immediately follow up the screening procedure with a diagnostic exam. This approach may be expensive, time-consuming, and not amenable to be performed at scale, meaning that most women may still need to wait weeks for potentially life-changing results. Roughly 4 million women may encounter such an unpleasant screening process every year.

Using methods and systems of the present disclosure, an AI-based triage system may be developed for screening mammography.

As screening exam images are received from the clinical imaging system, they may be processed by the AI-powered Triage Engine, which then stratifies the patient's case into one of a plurality of workflows. For example, the plurality of workflows may include two categories (e.g., normal and suspicious). As another example, the plurality of workflows may include three categories (e.g., normal, uncertain, and suspicious). Each of these categories may then be handled by a different set of dedicated radiologists, who are specialized to perform the workflow's particular set of responsibilities.

Figure 9:
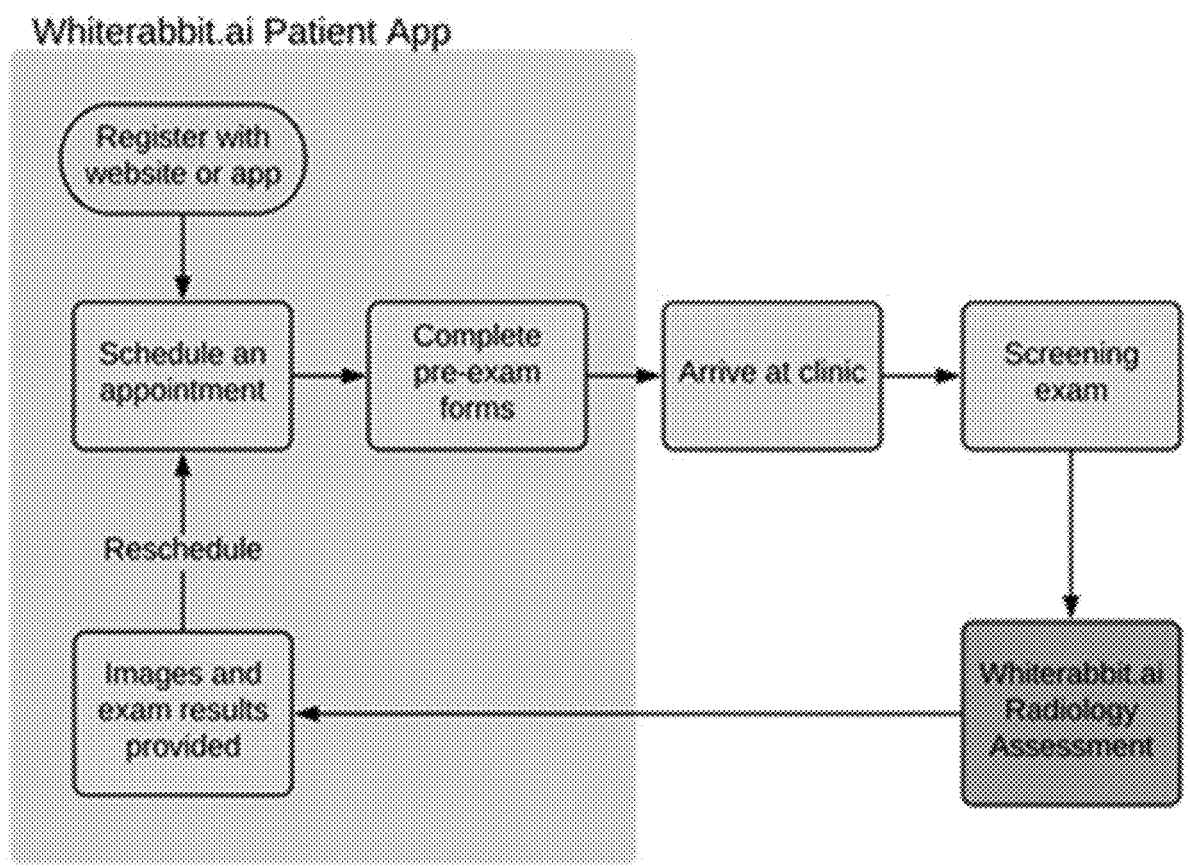
FIG. 9 shows an example of a schematic of patient flow through clinics with the AI-enabled real-time radiology system and patient mobile application (app), in accordance with disclosed embodiments.

FIG. 9 shows an example of a schematic of patient flow through clinics with the AI-enabled real-time radiology system and patient mobile application (app), in accordance with disclosed embodiments. The patient begins by registering with a website or patient app. Next, the patient uses the patient app to schedule an appointment for radiology screening. Next, the patient uses the patient app to complete pre-examination forms. Next, the patient arrives at the clinic and receives the screening examination. Next, the AI-based radiology assessment is performed on the medical images obtained from the patient's screening examination. Next, the patient's images and examination results are provided to the patient through the patient app. Next, the patient reschedules an appointment, if needed or recommended, using the patient app. The screening examination process may then proceed as before.

Figure 10:
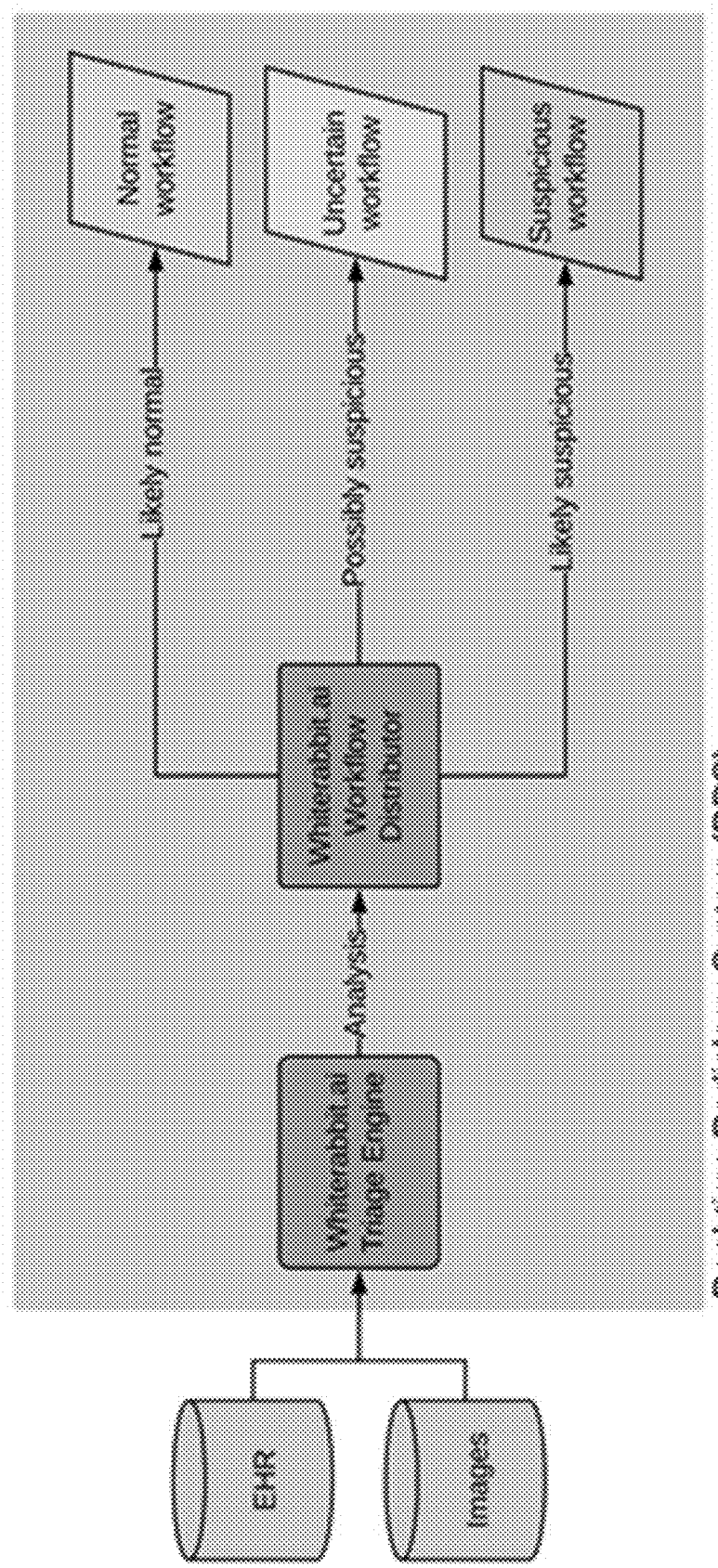
FIG. 10 shows an example of a schematic of an AI-assisted radiology assessment workflow, in accordance with disclosed embodiments.

FIG. 10 shows an example of a schematic of an AI-assisted radiology assessment workflow, in accordance with disclosed embodiments. First, a dataset comprising an electronic health record (EHR) and medical images of a patient are provided. Next, an AI-based triage engine processes the EHR and medical images to analyze and classify the dataset as likely normal, possibly suspicious, or likely suspicious. Next, a workflow distributor module distributes the patient's dataset to one of three workflows based on the classification of the dataset as likely normal, possibly suspicious, or likely suspicious: a normal workflow, an uncertain workflow, and a suspicious workflow, respectively. Each of the three workflows may comprise radiologist review or further AI-based analysis (e.g., by a trained algorithm).

The majority of mammography screening exams may be classified into the normal category. By having a first set of radiologists focusing only on this workflow, the concept of "batch reading" and the value and productivity gains associated with it can be applied and extended. Since the cases handled by this first set of radiologists may be nearly all normal cases, there may be fewer context-switches and penalties caused by handling highly variable cases. With the AI-based system, reports may be automatically pre-populated, allowing radiologists to spend significantly more time interpreting images rather than writing reports. In the rare case where the radiologist disagrees with the AI assessment of a normal case and instead considers the case suspicious, such cases may be handled as usual and the patient may be scheduled for a diagnostic exam. These normal cases may be further sub-divided into even more homogeneous batches to achieve a productivity improvement by grouping cases that an AI-based system has determined to be similar. For example, batching all AI-determined dense breasts together or batching cases that are visually similar based on AI-derived features.

A smaller fraction of mammography screening exams may be classified into the uncertain workflow. Such sessions may involve findings that the AI system does not classify as normal but that also do not meet the threshold for being outright suspicious. These may typically be the highly complex cases that require significantly more time per session for radiologist assessment as compared than those cases in the normal or suspicious workflow. For these reasons, it may be beneficial to have a separate second set of radiologists focus on performing this smaller volume of work, which has less homogeneity and potentially significantly more interpretation and reporting requirements. These radiologists may be more specialized in reading this difficult cases through more years of experience or training. This specialization may be made even more specific based on categories or features that the AI determines. For example, a group of radiologists may perform better than others at correctly assessing AI-determined tumor masses. Therefore, exams identified as such by the algorithm may be routed to this better suited group of specialists. In some cases, the second set of radiologists is the same as the first set of radiologists, but the radiological assessments of the different sets of cases are performed at different times based on a prioritization of the cases. In some cases, the second set of radiologists is a subset of the first set of radiologists.

The smallest but most important portion of the mammography screening exams may be classified into the suspicious workflow. A third set of radiologists may be assigned to this role to effectively read these cases as their "on-call" obligations. Most of the radiologist's time may be spent performing scheduled diagnostic exams. However, in the downtime between exams, they may be alerted to any suspicious cases such that they may verify the diagnosis as soon as possible. These cases may be critical to handle efficiently so that the patients can begin their follow-up diagnostic exam as soon as possible. In some cases, the third set of radiologists is the same as the first or second set of radiologists, but the radiological assessments of the different sets of cases are performed at different times based on a prioritization of the cases. In some cases, the third set of radiologists is a subset of the first or second set of radiologists.

In some cases, the workflow may comprise applying an AI-based algorithm to analyze a medical image to determine a difficulty of performing radiological assessment of the medical image, and then prioritizing or assigning the medical image to a set of radiologists (e.g., among a plurality of different sets of radiologists) for radiological assessment based on the determined degree of difficulty. For example, cases with low difficulty (e.g., more "routine" cases) may be assigned to a set of radiologists having relatively lower degree of skill or experience, while cases with higher difficulty (e.g., more suspicious or non-routine cases) may be assigned to a different set of radiologists having relatively higher degree of skill or experience (specialized radiologists). For example, cases with low difficulty (e.g., more "routine" cases) may be assigned to a first set of radiologists having relatively lower level of schedule availability, while cases with higher difficulty (e.g., more suspicious or non-routine cases) may be assigned to a different set of radiologists having relatively higher level of schedule availability.

In some cases, the degree of difficulty may be measured by an estimated length of time required to fully assess the image (e.g., about 1 minute, about 2 minutes, about 3 minutes, about 4 minutes, about 5 minutes, about 6 minutes, about 7 minutes, about 8 minutes, about 9 minutes about 10 minutes, about 15 minutes, about 20 minutes, about 25 minutes, about 30 minutes, about 40 minutes, about 50 minutes, about 60 minutes, or more than about 60 minutes. In some cases, the degree of difficulty may be measured by an estimated degree of concordance or agreement of radiological assessment of the medical image across a plurality of independent radiological assessments (e.g., performed by different radiologists or by the same radiologist on different days). For example, the estimated degree of concordance or agreement of radiological assessment may be about 50%, about 55%, about 60%, about 65%, about 70%, about 75%, about 80%, about 85%, about 90%, about 95%, about 96%, about 97%, about 98%, about 99%, or more than about 99%. In some cases, the degree of difficulty may be measured by a desired level of education, experience, or expertise of the radiologist (e.g., less than about 1 year, about 1 year, between 1 and 2 years, about 2 years, between 2 and 3 years, about 3 years, between 3 and 4 years, about 4 years, between 4 and 5 years, about 5 years, between 5 and 6 years, about 6 years, between 6 and 7 years, about 7 years, between 7 and 8 years, about 8 years, between 8 and 9 years, about 9 years, between 9 and 10 years, about 10 years, or more than about 10 years). In some cases, the degree of difficulty may be measured by an estimated sensitivity, specificity, positive predictive value (PPV), negative predictive value (NPV), or accuracy of the radiological assessment (e.g., about 50%, about 55%, about 60%, about 65%, about 70%, about 75%, about 80%, about 85%, about 90%, about 95%, about 96%, about 97%, about 98%, about 99%, or more than about 99%).

In some cases, the workflow may comprise applying an AI-based algorithm to analyze a medical image to determine a categorization of the medical image, and then prioritizing or assigning the medical image to a set of radiologists (e.g., among a plurality of different sets of radiologists) for radiological assessment based on the determined categorization of the medical image. For example, a set of cases having similar characteristics may be categorized together and assigned to the same radiologist or set of radiologists, thereby achieving a reduction in context switching and an increase in efficiency and accuracy. Similar characteristics may be based on, for example, location of a body where an ROI occurs, a density of tissue, a BIRADS score, etc. In some cases, workflow may comprise applying an AI-based algorithm to analyze a medical image to determine a lesion type of the medical image, and then prioritizing or assigning the medical image to a set of radiologists (e.g., among a plurality of different sets of radiologists) for radiological assessment based on the determined lesion type of the medical image.

In some cases, the workflow may comprise allowing radiologists to assign cases to themselves via a market-based system, whereby each case is assessed by an AI-based algorithm to determine an appropriate price or cost of the radiological assessment. Such a price or cost may be a determined relative value unit to be compensated to each radiologist upon completion of the radiological assessment. For example, each radiological assessment of a case may be priced based on determined characteristics (e.g., difficulty, length of examination time). In such a workflow, cases may not be assigned to radiologists, thereby avoiding the issue of radiologists who choose relatively routine or easy to obtain a high rate of reimbursement per case.

In some cases, the workflow may comprise assigning cases to a radiologist based on an assessed performance of the radiologist (e.g., prior sensitivity, specificity, positive predictive value (PPV), negative predictive value (NPV), accuracy, or efficiency of the radiologist in performing radiological assessments). Such performance may be determined or refined based on assigning control cases (e.g., positive or negative control cases) to the radiologist in a blinded manner to ensure quality control. For example, radiologists with better performance may be assigned a higher volume of cases or cases with higher value or compensation. By defining these distinct roles for a given radiologist (e.g., for any given day), each workflow can be individually optimized for task-specific needs. The AI-driven triage engine may allow real-time radiology to be delivered to patients at scale. The system may also enable dynamic allocation of cases based on expertise. For example, fellowship-trained breast imagers may be of the most value in the uncertain workflow, where their superior experience may be leveraged. Moreover, we can perform cross-clinic interpretation of screens across a network of clinics can be performed to ensure effective utilization of radiologists' time regardless of any individual clinic's staffing or patient base.

Report delivery may be performed as follows. The Mammography Quality Standards Act (MQSA) mandates that all patients receive a written lay person's summary of their mammography report directly. This report must be sent within 30 days of the mammogram. Verbal results are often used to expedite care and alleviate anxiety, but they must be supported by written reports. Reports can be mailed, sent electronically, or handed to the patient. Typically, clinics may use paper mail to deliver reports to their patients. The AI-based clinic may deliver mammography reports electronically via the patient application. The source images may also be made available electronically, so that the patient may easily obtain and transfer the information to other clinics. Patients in the real-time radiology workflow may receive a screening and diagnostic report immediately before leaving the clinic.

Timely reporting of screening results may be critical to patient satisfaction. Waiting more than two weeks for results and not being able to get in touch with someone to answer questions have been cited as key contributing reasons for patient dissatisfaction (which may in return decrease future screening rates). This system may ensure that a patient does not accidentally receive the wrong report, and that patients do not have uncertainty about when may receive their results come.

The AI-based system may be continually trained as follows. As the clinical practice is operated, new data is continually collected and used to further train and refine the AI system, thereby further improving the quality of care and enabling new improvements to the patient experience. Each patient exam provides the system with an annotated, and possibly biopsy-proven, example to add to the dataset. In particular, the workflow of the real-time radiology system facilitates prioritizing the capture of high-value cases. The identification of false positives and false negatives (truly suspicious cases not flagged) may be crucial for enhancing the system's performance by providing challenging examples with high instructive value. Even cases that are classified correctly (e.g., with respect to the radiologist's review as the ground truth) may provide useful feedback. Incorporating these cases in the training data set may provide the system with a valuable source of information for uncertainty calibration, which ensures that the confidence values produced by the AI-based system are accurate. This may drastically increase the overall robustness and, in turn, trust in the system. By improving the end-to-end patient workflow and maintaining a radiologist in the loop, the AI-based clinical system may automatically discover the important pieces of information outlined above. The resulting system may be always improving and always providing high-quality patient care and radiological assistance.

The AI-powered mammography screening clinics can provide patients with high-quality service and accuracy throughout the screening process. Patients may be able to walk into a clinic, receive a screening for cancer, receive any needed follow-up work, and leave with their diagnosis in hand, thereby completing the entire screening and diagnosis process during the course of a single visit with immediate results. The patient application may be configured to provide price transparency, hassle-free scheduling, error-free form filling, and instantaneous delivery of reports and images, thereby improving the ease, stress, and efficiency of the patient screening process.

The radiologists may be able to provide more accurate and more productive results by employing a specialized set of normal, uncertain, and suspicious (or alternative categorization based on an AI assessment of the images) workflows orchestrated by the AI triage engine. Clinicians may become more capable as the AI system learns and augments their abilities. AI-based or AI-assisted mammography may be delivered to a large population scale with low cost and high efficiency, thereby enhancing the cancer screening process and patient outcomes.

Example 4—Real-Time Radiology in Breast Cancer Screening Mammography when Coupled with Artificial Intelligence Technologies A software system is developed that is configured to prioritize suspicious screening mammograms for immediate review by radiologists, thereby reducing the time to diagnostic follow-up. The software system is developed with a goal of significantly reducing patient anxiety as well as the overall time to treatment, by shortening the review times for suspicious mammography cases. Reductions in the wait time, which may often be up to about 2-4 weeks between the first and second evaluations, may be expected to extend the life expectancy of those subjects who are actually positive for breast cancer. An additional potential benefit is that the software may reduce the likelihood of missing some cancers.

In some studies, women who are false positives at screening (normal cases flagged as suspicious, BIRADS 0) but receive immediate follow-up may experience nearly the same level of anxiety as women with normal diagnoses. Many of these women may not even perceive themselves as having an abnormal screening result. Therefore, immediate follow-up care may mitigate potential anxiety caused by a false-positive screening result.

On the other hand, women who receive false-positives screening results and are called back for a follow-up diagnostic exam days or weeks later, may seek more medical attention for breast-related concerns and other medical issues. Therefore, women who are able to receive definitive mammography results during the same clinical visit as the mammography scan may be more likely to be satisfied with the screening experience and to have high compliance rates with future screening recommendations.

However, many breast imaging centers may be unable to deliver immediate follow-up exams. This can be due to several challenges including scheduling constraints, timeliness of receiving prior evaluations from other institutions, and productivity loss due to reading each exam immediately after it is acquired. Perhaps most critically, reading several breast screening cases in a batch significantly improves the evaluation accuracy of the reader. This motivates waiting until a large enough batch of cases has been collected before reading an exam, making it impossible to provide immediate results and follow-up examination to a patient if indicated.

Figure 11:
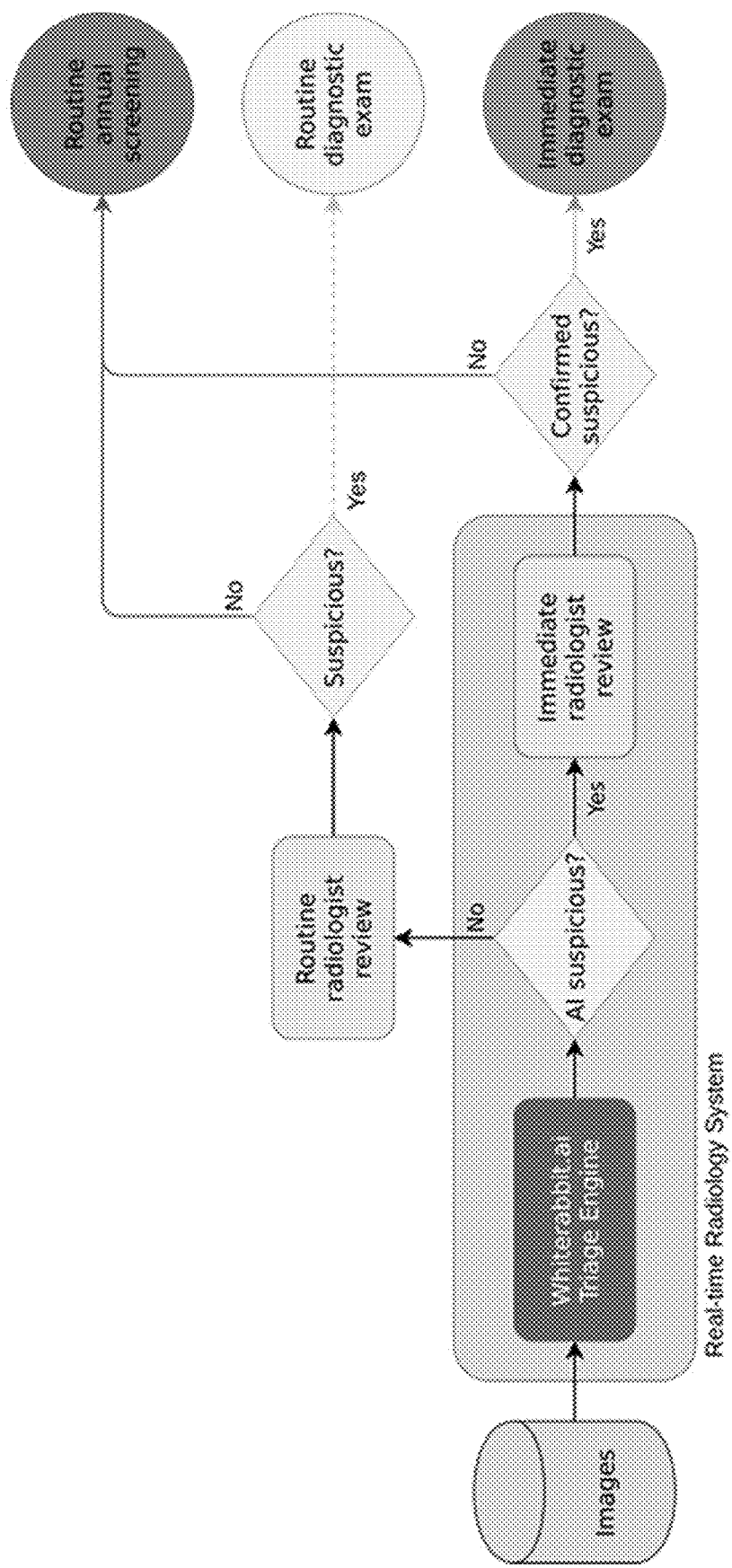
FIG. 11 shows an example of a triage software system developed using machine learning for screening mammography to enable more timely report delivery and follow-up for suspicious cases (e.g., as performed in a batch reading setting), in accordance with disclosed embodiments.

Machine learning-based methods are employed to evaluate suspicious findings in mammography and tomosynthesis images. A triage software system is developed using machine learning for screening mammography to enable more timely report delivery and follow-up for suspicious cases (e.g., as performed in a batch reading setting) (as shown in FIG. 11). The medical images are fed into a real-time radiology system for processing. An AI-based triage engine of the real-time radiology system processes the medical images to classify the images as suspicious or not suspicious (e.g., normal or routine). If an image is classified as suspicious by the AI-based triage engine, then the image is sent for immediate radiologist review (e.g., during the same visit or same day as the initial screening appointment). The immediate radiologist review may result in a confirmation of a suspicious case (which results in an immediate diagnostic exam being ordered) or a reversal of the suspicious case (which results in the next scheduled routine annual screening being performed). If an image is classified as not suspicious (e.g., normal or routine) by the AI-based triage engine, then the image is sent for routine radiologist review. The routine radiologist review may result in an assessment of the case being suspicious (which results in a routine diagnostic exam being ordered) or a confirmation of the case as not being suspicious (which results in the next scheduled routine annual screening being performed).

This software enables high-volume breast screening clinics to deliver same-day or same-visit diagnostic follow-up imaging to patients with abnormal-appearing mammography results. Leveraging such rapid diagnostic follow-up imaging can pave the way for breast imaging clinics to deliver the highest accuracy with the highest level of service and to significantly reduce patient anxiety.

Using these machine learning-based approaches, the time-to-treatment of true tumors is reduced so that the patient has an increased probability of a longer lifespan as compared to those patients who are not evaluated by AI and who do not receive the follow-up diagnostic evaluation on the same day.

The machine learning-based approach to evaluate suspicious findings in mammography and tomosynthesis images confers several advantages and objectives as follows. First, the time from initial screening exam to the delivery of diagnostic imaging results is reduced (potentially significantly) for breast cancer screening, and the likelihood of an accurate diagnosis is improved. For example, such diagnoses may be produced with greater sensitivity, specificity, positive predictive value, negative predictive value, area under the receiver operator characteristic (AUROC), or a combination thereof. Second, the approaches that combine radiologists with artificial intelligence may effectively improve the speed and/or quality of the initial evaluation. Third, more advanced diagnostic exams (e.g., additional X-ray based imaging, ultrasound imaging, another type of medical imaging, or a combination thereof) may be completed within a short period (e.g., within 60 minutes) of when the patient receives his or her screening results. Fourth, such methods may advantageously result in improvement in patient satisfaction that is attributable to the more timely delivery of results and follow-up imaging.

Methods

A clinical workflow is optimized to deliver a higher level of service to patients. As more patients and data are collected into training datasets, the machine learning algorithm continuously improves in the accuracy (or sensitivity, specificity, positive predictive value, negative predictive value, AUROC, or a combination thereof) of its computer aided diagnosis.

Computer algorithms and software are developed to automatically classify breast screening images into probably abnormal and normal categories with a high degree of accuracy. Such software can enable high-volume breast screening clinics to deliver same-day or same-visit diagnostic follow-up imaging to patients with abnormal-appearing initial screening results. This will also require evaluating changes to clinical operations, in particular how screening cases are read and how the second diagnostic evaluation can be performed, within 60 minutes of the initial test.

A rapid screening approach is implemented for all patients at a breast screening clinic. About 10% of the patients who are screened have suspicious results and are subsequently recommended for a diagnostic exam to be performed on the same day or during the same visit. The rapid turn-around time of the screening result and follow-up diagnostic exam are enabled by careful coordination between radiologists, clinical staff, and patients in the clinical environment. As more information is collected, the machine learning that is trained with increasingly larger training datasets yields a higher level of accuracy in detecting suspicious mammography scans.

As the acquisitions of screening exams are completed, the images are sent to a router, received by the software, and rapidly classified (e.g., within about one minute). If the screening is marked by the machine learning algorithm as probably normal, then the patient ends her visit and exits the clinic as usual. However, if the screening is flagged by the machine learning algorithm as probably abnormal, then the patient will be asked to wait for up to about 10 minutes while the case is immediately reviewed by the radiologist (as shown in FIG. 11).

Assuming that a given clinic screens about 30 patients per day and a 10% rate of possible positives, about 3 patients per day are typically be found positive by the machine learning algorithm and would be designated as eligible for real-time diagnostic follow-up after review by the radiologist (e.g., usually additional tomosynthesis imaging and possibly an ultrasound exam).

Several metrics are used to demonstrate the effectiveness of the real-time radiology methods and systems. First, the change in the time it takes between a patient's initial screening exam and the delivery of diagnostic imaging results under the routine workflow and the proposed real-time workflow may be measured, in order to capture both changes in the latency of when a screening a case is reviewed, as well as logistics like mailing letters and appointment scheduling.

Second, the real-time radiology model is evaluated continuously (e.g., on a monthly basis) based on the latest data collected. For example, the parameters of the computer vision algorithm are tuned and altered to improve its accuracy for the upcoming subsequent time period of screenings (e.g., one month). The effectiveness of the changes to the computer program are evaluated on a blinded test dataset of hundreds of representative exams and from the interim results from the subsequent time period of screenings.

Third, patient satisfaction surveys are reviewed periodically to help determine how operational processes may be improved to better enable follow-up diagnostic examination within a short period of time (e.g., about 60 minutes).

The following data may be collected for each patient who undergoes a mammographic screening/diagnostic assessment via the real-time radiology workflow: patient demographics (e.g., age, race, height, weight, socioeconomic background, smoking status, etc.), patient imaging data (e.g., acquired by mammography), patient outcomes (e.g., BIRADS for screening and diagnostic exams and biopsy pathology results, where applicable), patient visit event time stamps, patient callback rate for batch-read and real-time cases, and radiologist interpretation time for screening and diagnostic cases.

Using methods and systems of the present disclosure, real-time radiology may be performed with potential benefits including: detecting a tumor that may not have otherwise have been recognized (or may only be recognized until the tumor has progressed), a reduced time to treatment, an improved longevity of the patient due to recognition and treatment compared to traditional evaluation process, and reduced patient anxiety since the waiting time between testing has been eliminated.

Example 5—a Multi-Site Study of a Breast Density Deep Learning Model for Full-Field Digital Mammography and Digital Breast Tomosynthesis Exams Abstract Deep learning (DL) models hold promise for mammographic breast density estimation, but performance can be hindered by limited training data or image differences that can occur across clinics. Digital breast tomosynthesis (DBT) exams are increasingly becoming the standard for breast cancer screening and breast density assessment, but much more data is available for full-field digital mammography (FFDM) exams. A breast density DL model was developed in a multi-site setting for synthetic 2D mammography (SM) images derived from 3D DBT exams using FFDM images and limited SM data. A DL model was trained to predict Breast Imaging Reporting and Data System (BI-RADS) breast density using FFDM images acquired from 2008 to 2017 (Site 1: 57492 patients, 750752 images) for a retrospective study. The FFDM model was evaluated on SM datasets from two institutions (Site 1: 3842 patients, 14472 images; Site 2: 7557 patients, 63973 images). Adaptation methods were investigated to improve performance on the SM datasets and the effect of dataset size on each adaptation method was considered. Statistical significance was assessed through use of confidence intervals, and estimated by bootstrapping. Even without adaptation, the model demonstrated close agreement with the original reporting radiologists for all three datasets (Site 1 FFDM: linearly-weighted κw=0.75, 95% confidence interval (CI): [0.74, 0.76]; Site 1 SM: κw=0.71, CI: [0.64, 0.78]; Site 2 SM: κw=0.72, CI: [0.70, 0.75]). With adaptation, performance improved for Site 2 (Site 1: κw=0.72, CI: [0.66, 0.79], Site 2: κw=0.79, CI: [0.76, 0.81]) by use of only 500 SM images. These results establish that the BI-RADS breast density DL model demonstrated a high-level of performance on FFDM and SM images from two institutions by the use of methods requiring no or few SM images.

A multisite study was performed to develop a breast density deep learning model for full-field digital mammography and synthetic mammography, as described by, for example, Matthews et al., "A Multisite Study of a Breast Density Deep Learning Model for Full-Field Digital Mammography and Synthetic Mammography," Radiology: Artificial Intelligence, doi.org/10.1148/ryai.2020200015, which is incorporated by reference herein in its entirety.

Introduction

Breast density is an important risk factor for breast cancer, and areas of higher density can mask findings within mammograms leading to lower sensitivity. In some states, clinics are required to inform women of their density. Radiologists typically assess breast density using the Breast Imaging Reporting and Data System (BI-RADS) lexicon, which divides breast density into four categories: almost entirely fatty, scattered areas of fibroglandular density, heterogeneously dense, and extremely dense (as shown in FIGS. 12A-12D). Unfortunately, radiologists exhibit intra- and inter-reader variability in the assessment of BI-RADS breast density, which can result in differences in clinical care and estimated risk.

Figure 12A:
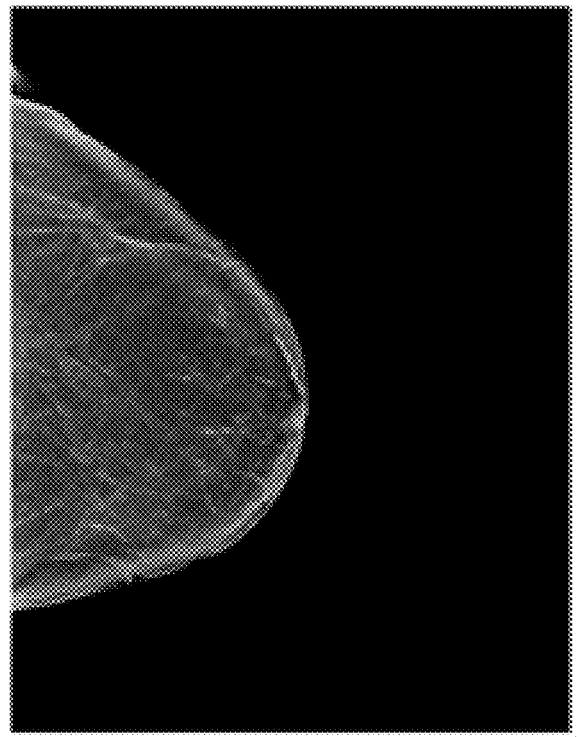
FIGS. 12A-12D show examples of synthetic 2D mammography (SM) images derived from digital breast tomosynthesis (DBT) exams for each of the four Breast Imaging Reporting and Data System (BI-RADS) breast density categories: (A) almost entirely fatty (FIG. 12A), (B) scattered areas of fibroglandular density (FIG. 12B), (C) heterogeneously dense (FIG. 12C), and (D) extremely dense (FIG. 12D), in accordance with disclosed embodiments.
Figure 12B:
Figure 12C:
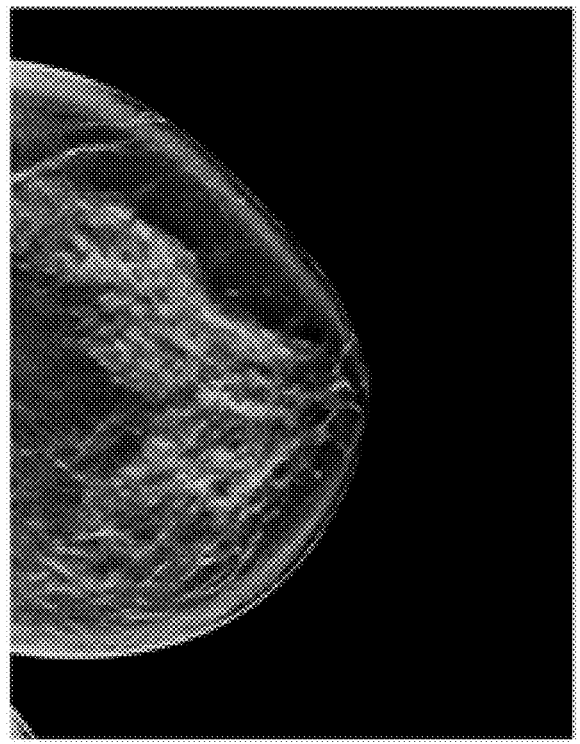
Figure 12D:
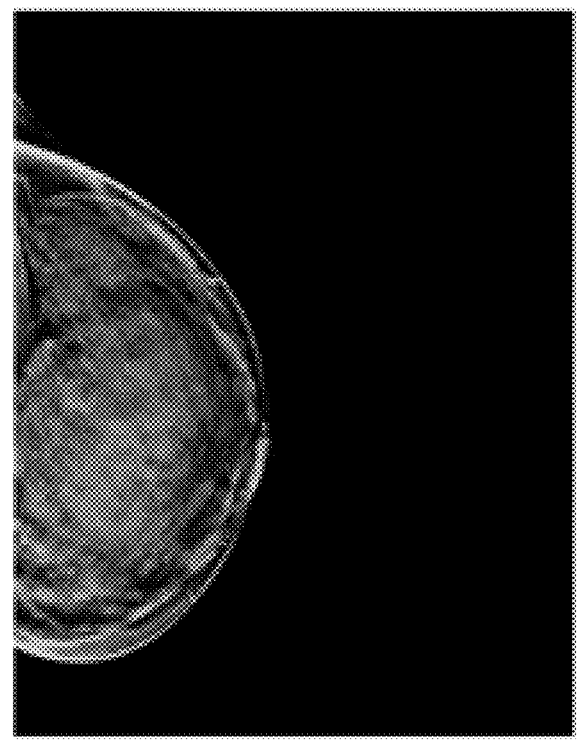
Figure 13A:
FIGS. 13A-13D show a comparison between a full-field digital mammography (FFDM) image (FIG. 13A) and a synthetic 2D mammography (SM) image (FIG. 13B) of the same breast under the same compression, in accordance with disclosed embodiments. A zoomed-in region, whose original location is denoted by the white box, is shown for both the FFDM image (FIG. 13C) and the SM image (FIG. 13D) to highlight the differences in texture and contrast that can occur between the two image types.
Figure 13B:
Figure 13C:
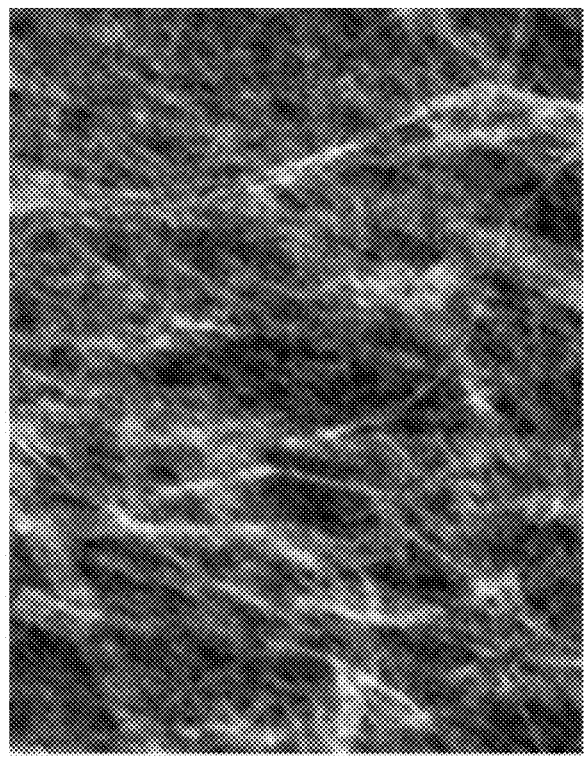
Figure 13D:
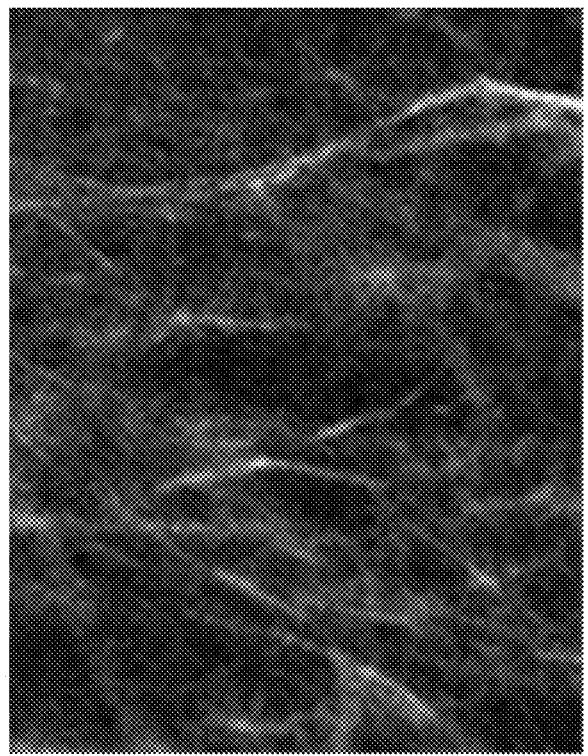

FIGS. 12A-12D show examples of synthetic 2D mammography (SM) images derived from digital breast tomosynthesis (DBT) exams for each of the four Breast Imaging Reporting and Data System (BI-RADS) breast density categories: (A) almost entirely fatty (FIG. 12A), (B) scattered areas of fibroglandular density (FIG. 12B), (C) heterogeneously dense (FIG. 12C), and (D) extremely dense (FIG. 12D). Images are normalized so that the grayscale intensity windows found in their Digital Imaging and Communications in Medicine (DICOM) headers range from 0.0 to 1.0.

Deep learning (DL) may be employed to assess BI-RADS breast density for both film and full-field digital mammography (FFDM) images, with some models demonstrating closer agreement with consensus estimates than individual radiologists. To realize the promise of using these DL models in clinical practice, two key challenges must be met. First, as breast cancer screening is increasingly moving to digital breast tomosynthesis (DBT) due to improved reader performance, DL models may need to be compatible with DBT exams. FIGS. 13A-13D show the differences in image characteristics between 2D images for FFDM and DBT exams. However, the relatively recent adoption of DBT at many institutions means that the datasets available for training DL models are often fairly limited for DBT exams compared with FFDM exams. Second, DL models may need to offer consistent performance across sites, where differences in imaging technology, patient demographics, or assessment practices can impact model performance. To be practical, this may need to be achieved while requiring little additional data from each site.

FIGS. 13A-13D show a comparison between a full-field digital mammography (FFDM) image (FIG. 13A) and a synthetic 2D mammography (SM) image (FIG. 13B) of the same breast of a subject under the same compression; and a zoomed-in region, whose original location is denoted by the white box, both the FFDM image (FIG. 13C) and the SM image (FIG. 13D) to highlight the differences in texture and contrast that can occur between the two image types. Images are normalized so that the grayscale intensity windows found in their Digital Imaging and Communications in Medicine (DICOM) headers range from 0.0 to 1.0.

A BI-RADS breast density DL model was developed that offers close agreement with the original reporting radiologists for both FFDM and DBT exams at two institutions. A DL model was first trained to predict BI-RADS breast density using a large-scale FFDM dataset from one institution. Then, the model was evaluated on a test set of FFDM exams as well as synthetic 2D mammography (SM) images generated as part of DBT exams (C-View, Hologic, Inc., Marlborough, MA), acquired from the same institution and from a separate institution. Adaptation techniques, requiring few SM images, were explored to improve performance on the two SM datasets.

Materials and Methods

The retrospective study was approved by an institutional review board for each of the two sites where data were collected (Site 1: internal institutional review board, Site 2: Western Institutional Review Board). Informed consent was waived and all data were handled according to the Health Insurance Portability and Accountability Act.

Datasets were collected from two sites: Site 1, an academic medical center located in the mid-western region of the United States, and Site 2, an out-patient radiology clinic located in northern California. For Site 1, 191,493 mammography exams were selected (FFDM: n=187,627; SM: n=3,866). The exams were read by one of 11 radiologists with breast imaging experience. For Site 2, 16283 exams were selected. The exams were read by one of 12 radiologists with breast imaging experience ranging from 9 to 41 years. The BI-RADS breast density assessments of the radiologists were obtained from each site's mammography reporting software (Site 1: Magview version 7.1, Magview, Burtonsville, Maryland; Site 2: MRS version 7.2.0; MRS Systems Inc. Seattle, Washington). To facilitate development of our DL models, patients were randomly selected for training (FFDM: 50700, 88%; Site 1 SM: 3169, 82%; Site 2 SM: 6056, 80%), validation (FFDM: 1832, 3%; Site 1 SM: 403, 10%; Site 2 SM: 757, 10%), or testing (FFDM: 4960, 9%; Site 1 SM: 270, 7%; Site 2 SM: 744, 10%) purposes. All exams with a BI-RADS breast density assessment were included. For the test sets, exams were required to have all four standard screening mammography images (the mediolateral oblique and craniocaudal views of the left and right breasts). The distribution of the BI-RADS breast density assessments for each set are shown in

TABLE 1

Description of the Site 1 full-field digital mammography (FFDM) and synthetic 2D mammography (SM) training (train), validation (val), and test (test) datasets. The total number of patients, exams, and images are given for each dataset. The number of images for the four Breast Imaging Reporting and Data System (BI-RADS) breast density categories are also provided.

|          | FFDM Train     | FFDM Val     | FFDM Test     | SM Train    | SM Val      | SM Test    |
|----------|----------------|--------------|---------------|-------------|-------------|------------|
| Patients | 50700          | 1832         | 4960          | 3169        | 403         | 270        |
| Exams    | 168208         | 6157         | 13262         | 3189        | 407         | 270        |
| Images   | 672704         | 25000        | 53048         | 11873       | 1519        | 1080       |
| BI-RADS A | 80459 (12.0%) | 3465 (13.9%) | 4948 (9.3%)   | 1160 (9.8%) | 154 (10.1%) | 96 (8.9%)  |
| BI-RADS B | 348878 (51.9%)| 12925 (51.7%)| 27608 (52.0%) | 6121 (51.6%)| 771 (50.8%) | 536 (49.6%)|
| BI-RADS C | 214465 (33.9%)| 7587 (30.3%) | 18360 (34.6%) | 3901 (32.9%)| 530 (33.6%) | 388 (35.9%)|
| BI-RADS D | 28902 (4.3%)  | 1023 (4.1%)  | 2132 (4.0%)   | 691 (5.8%)  | 84 (5.5%)   | 60 (5.6%)  |

TABLE 2

Description of the Site 2 synthetic 2D mammography (SM) training (train), validation (val), and test (test) datasets. The total number of patients, exams, and images are given for each dataset. The number of images for the four Breast Imaging Reporting and Data System (BI-RADS) breast density categories are also provided.

|           | Train         | Val          | Test         |
|-----------|---------------|--------------|--------------|
| Patients  | 6056          | 757          | 744          |
| Exams     | 13061         | 1674         | 1548         |
| Images    | 51241         | 6540         | 6192         |
| BI-RADS A | 7866 (15.4%)  | 865 (13.2%)  | 948 (15.3%)  |
| BI-RADS B | 20731 (40.5%) | 2719 (41.6%) | 2612 (42.2%) |
| BI-RADS C | 15706 (30.7%) | 2139 (32.7%) | 1868 (30.2%) |
| BI-RADS D | 6938 (13.5%)  | 817 (12.5%)  | 764 (12.3%)  |

The two sites serve different patient populations. The patient cohort from 1 is 59% Caucasian (34192/58397), 23% African American (13201/58397), 3% Asian (1630/58397), and 1% Hispanic (757/58397) while Site 2 is 58% Caucasian (4350/7557), 1% African American (110/7557), 21% Asian (1594/7557), and 7% Hispanic (522/7557).

Deep Learning Model

The DL model and training procedure were implemented using the pytorch DL framework (pytorch.org, version 1.0), which comprises a deep neural network model. The base model architecture comprised a pre-activation Resnet-34, where the batch normalization layers were replaced with group normalization layers. The model was configured to process as input a single image, corresponding to one of the views from a mammography exam, and produce estimated probabilities that the image is of a breast belonging to each of the BI-RADS breast density categories.

The deep learning (DL) model was trained using the full-field digital mammography (FFDM) dataset (as shown in Table 1) by use of the Adam optimizer with a learning rate of $10^{-4}$ and a weight decay of $10^{-3}$. Weight decay not was applied to the parameters belonging to the normalization layers. The input was resized to 416×320 pixels, and the pixel intensity values were normalized so that the grayscale window denoted in the Digital Imaging and Communications in Medicine (DICOM) header ranged from 0.0 to 1.0. Training was performed using mixed precision and gradient checkpointing with batch sizes of 256 distributed across two NVIDIA GTX 1080 Ti graphics processing units (Santa Clara, CA). Each batch was sampled such that the probability of selecting a BI-RADS B or BI-RADS C sample was four times that of selecting a BI-RADS A or BI-RADS D sample, which roughly corresponds to the distribution of densities observed in the U.S. Horizontal and vertical flipping were employed for data augmentation. In order to obtain more frequent information on the training progress, epochs were capped at 100 thousand samples compared with a total training set size of over 672 thousand samples. The model was trained for 100 such epochs. Results are reported for the epoch that had the lowest cross entropy loss on the validation set, which occurred after 93 epochs.

The parameters for the vector and matrix calibration methods were chosen by minimizing a cross-entropy loss function by use of the BFGS optimization method (scipy.org, version 1.1.0). The parameters were initialized such that the linear layer corresponded to the identity transformation. Training was stopped when the L2 norm of the gradient was less than $10^{-6}$ or when the number of iterations exceeded 500. Retraining the last fully-connected layer for the fine-tuning method was performed by use of the Adam optimizer with a learning rate of $10^{-4}$ and weight decay of $10^{-5}$. The batch size was set to 64. The fully-connected layer was trained from random initialization for 100 epochs, and results were reported for the epoch with the lowest validation cross entropy loss. Training from scratch on the synthetic 2D mammography (SM) datasets was performed following the same procedure as for the base model. For fine-tuning and training from scratch, the size of an epoch was set to the number of training samples.

Domain Adaptation

Domain adaptation was performed to take a model trained on a dataset from one domain (source domain) and transfer its knowledge to a dataset in another domain (target domain), which is typically much smaller in size. Features learned by DL models in the early layers can be general, e.g., domain and task agnostic. Depending on the similarity of domains and tasks, even deeper features learned from one domain can be reused for another domain or task. Models that can be directly applied to the new domain without modification are the to generalize.

Approaches were developed for adapting the DL model trained on FFDM images (source domain) to SM images (target domain) that reuse all the features learned from the FFDM domain. First, to perform calibration of neural networks, a small linear layer was added following the final fully-connected layer. Two forms for the linear layer were considered: (1) where the matrix is diagonal, which is denoted as vector calibration, and (2) where the matrix is allowed to freely vary, which is denoted as matrix calibration. Second, the final fully-connected layer of the Resnet-34 model was retrained on samples from the target domain, which is denoted as fine-tuning.

In order to investigate the impact of the target domain dataset size, the adaptation techniques were repeated for different SM training sets across a range of sizes. The adaptation process was repeated 10 times for each dataset size with different random samples of the training data. For each sample, the training images were randomly selected, without replacement, from the full training set. As a reference, a Resnet-34 model was trained from scratch, e.g., from random initialization, for the largest number of training samples for each SM dataset.

Statistical Analysis

To obtain an exam-level assessment, each image within an exam was processed by the DL model and the resulting probabilities were averaged. Several performance metrics were computed from these average probabilities for the 4-class BI-RADS breast density task and the binary dense (BI-RADS C+D) vs. non-dense (BI-RADS A+B) task: (1) accuracy, estimated based on concordance with the original reporting radiologists, (2) the area under the receiver operating characteristic curve (AUC), and (3) Cohen's kappa (scikit-learn.org, version 0.20.0). Confidence intervals were computed by use of non-Studentized pivotal bootstrapping of the test sets for 8000 random samples. For the 4-class problem, the macroAUC (the average of the four AUC values from the one vs. others tasks) and Cohen's kappa with linear weighting were reported. For the binary density tasks, the predicted dense and non-dense probabilities were computed by summing the predicted probabilities for the corresponding BI-RADS density categories.

Results

Performance of the deep learning model on FFDM exams was evaluated as follows. The trained model was first evaluated on a large held-out test set of FFDM exams from Site 1 (4960 patients, 53048 images, mean age: 56.9, age range: 23-97). In this case, the images were from the same institution and of the same image type as employed to train the model. The BI-RADS breast density distribution predicted by the DL model (A: 8.5%, B: 52.2%, C: 36.1%, D: 3.2%) was similar to that of the original reporting radiologists (A: 9.3%, B: 52.0%, C: 34.6%, D: 4.0%). The DL model exhibited close agreement with the radiologists for the 4-class BI-RADS breast density task across a variety of performance measures (as shown in Table 3), including accuracy (82.2%, 95% confidence interval (CI): [81.6%, 82.9%]) and linearly-weighted Cohen's kappa ($\kappa w$=0.75, CI: [0.74, 0.76]). A high-level of agreement was also observed for the binary breast density task (accuracy=91.1%, CI: [90.6%, 91.6%], AUC=0.971, CI: [0.968, 0.973], $\kappa$=0.81, CI: [0.80, 0.82]). As demonstrated by the confusion matrices shown in FIGS. 14A-14D, the DL model was rarely off by more than one breast density category (e.g., by calling an extremely dense breast as a scattered outcome; 0.03%, 4/13262). This was learned implicitly by the DL model without any explicit penalties for these types of larger errors.

Figure 14A:
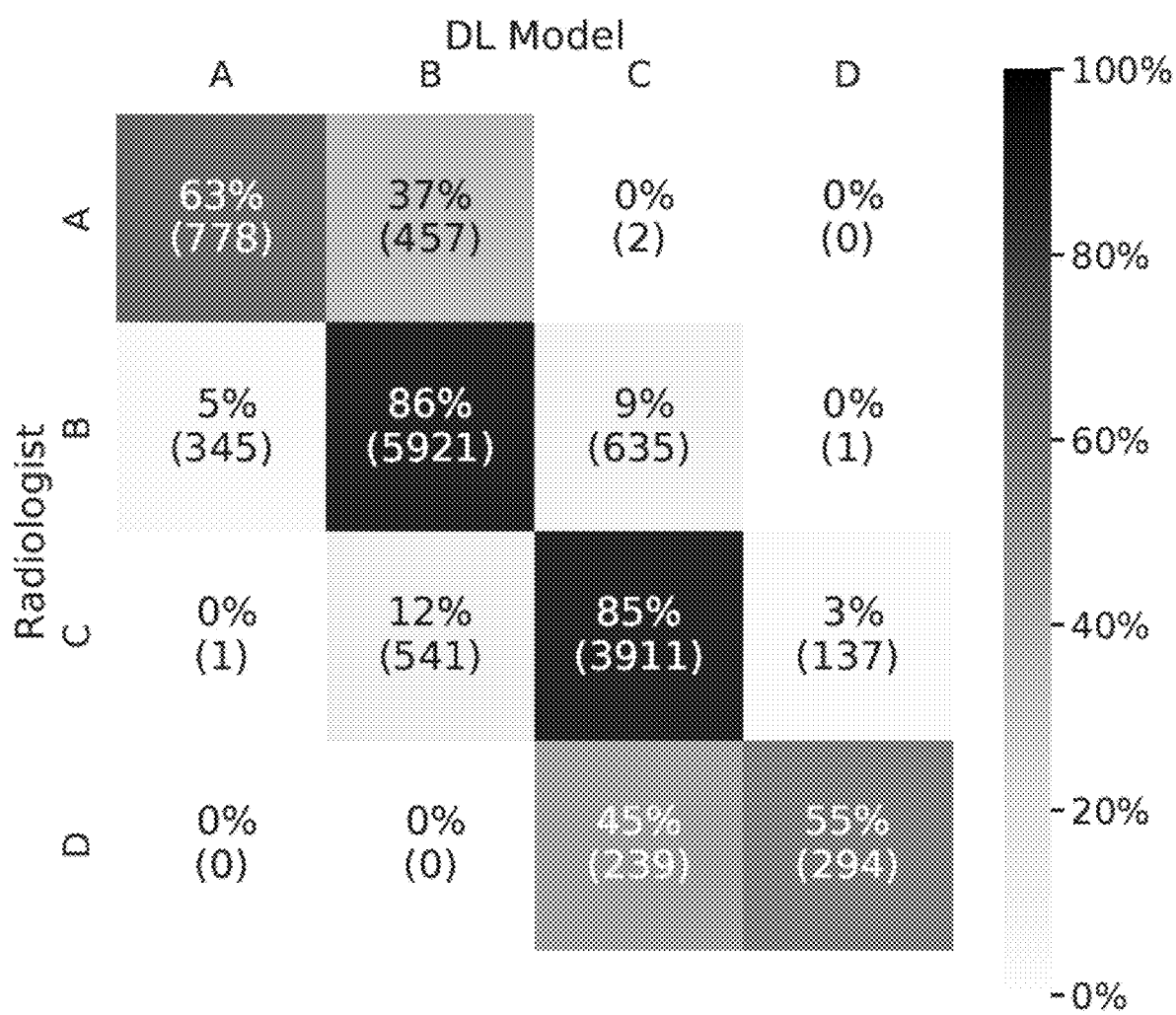
FIGS. 14A-14B show confusion matrices for the Breast Imaging Reporting and Data System (BI-RADS) breast density task (FIG. 14A) and the binary density task (dense, BI-RADS C+D vs. non-dense, BI-RADS A+B) (FIG. 14B) evaluated on the full-field digital mammography (FFDM) test set, in accordance with disclosed embodiments. The numbers of test samples (exams) within each bin are shown in parentheses.
Figure 14B:
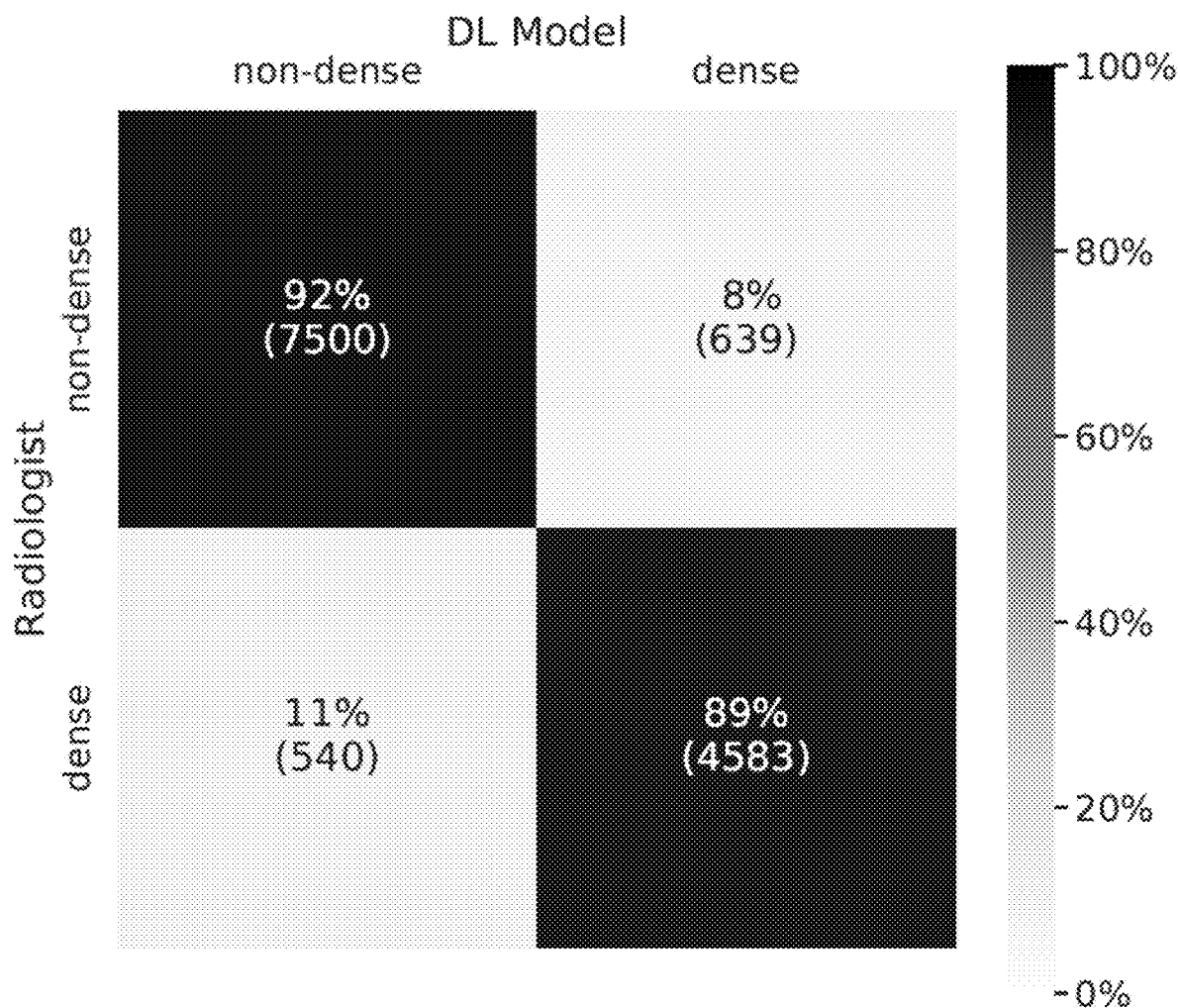
Figure 15A:
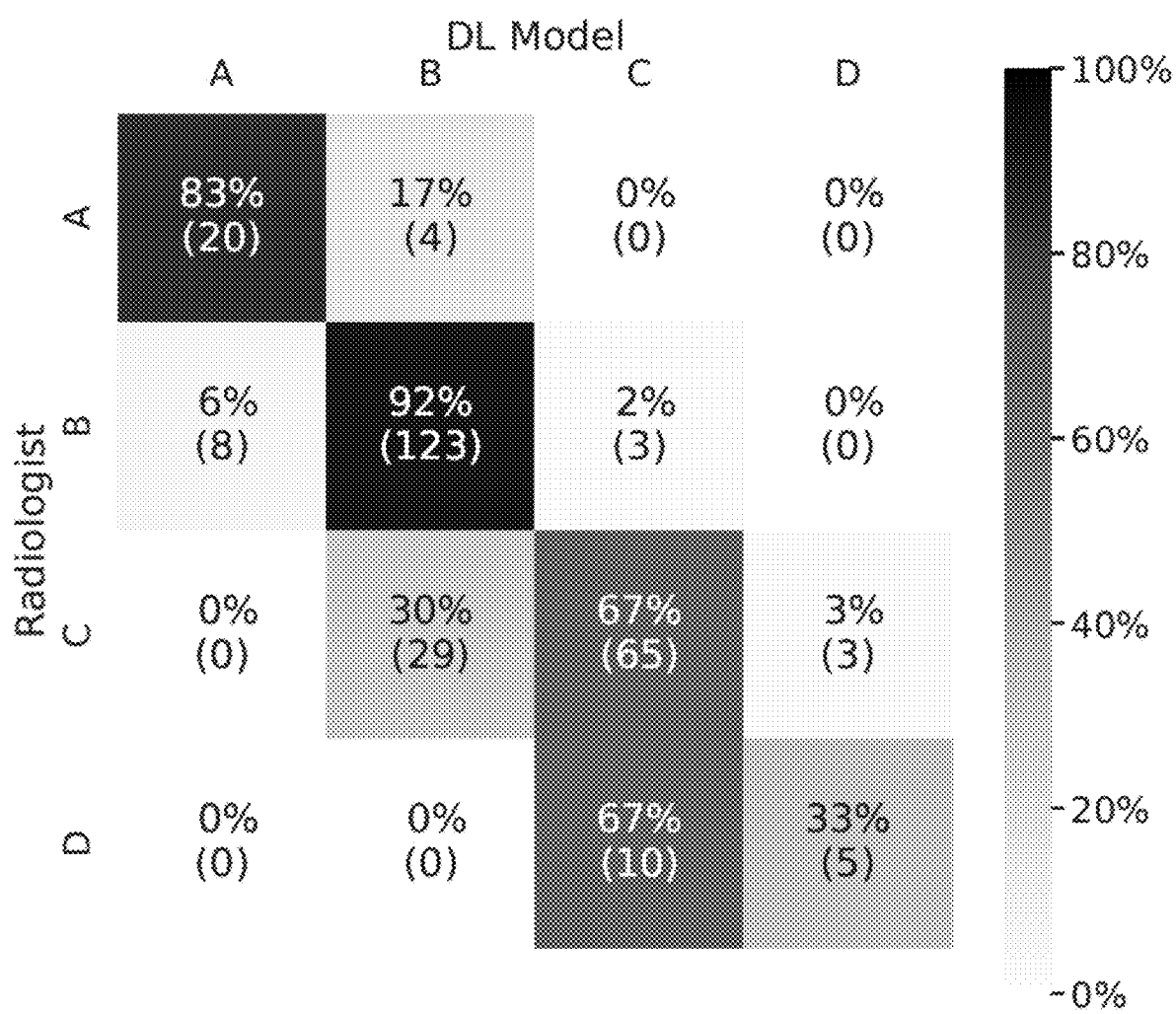
FIGS. 15A-15D show confusion matrices, evaluated on the Site 1 SM test set, for the Breast Imaging Reporting and Data System (BI-RADS) breast density task without adaptation (FIG. 15A), the binary density task (dense, BI-RADS C+D vs. non-dense, BI-RADS A+B) (FIG. 15B) without adaptation, the BI-RADS breast density task with adaptation by matrix calibration for 500 training samples (FIG. 15C), and the binary density task (dense vs. non-dense) (FIG. 15B) with adaptation by matrix calibration for 500 training samples, in accordance with disclosed embodiments. The numbers of test samples (exams) within each bin are shown in parentheses.
Figure 15B:
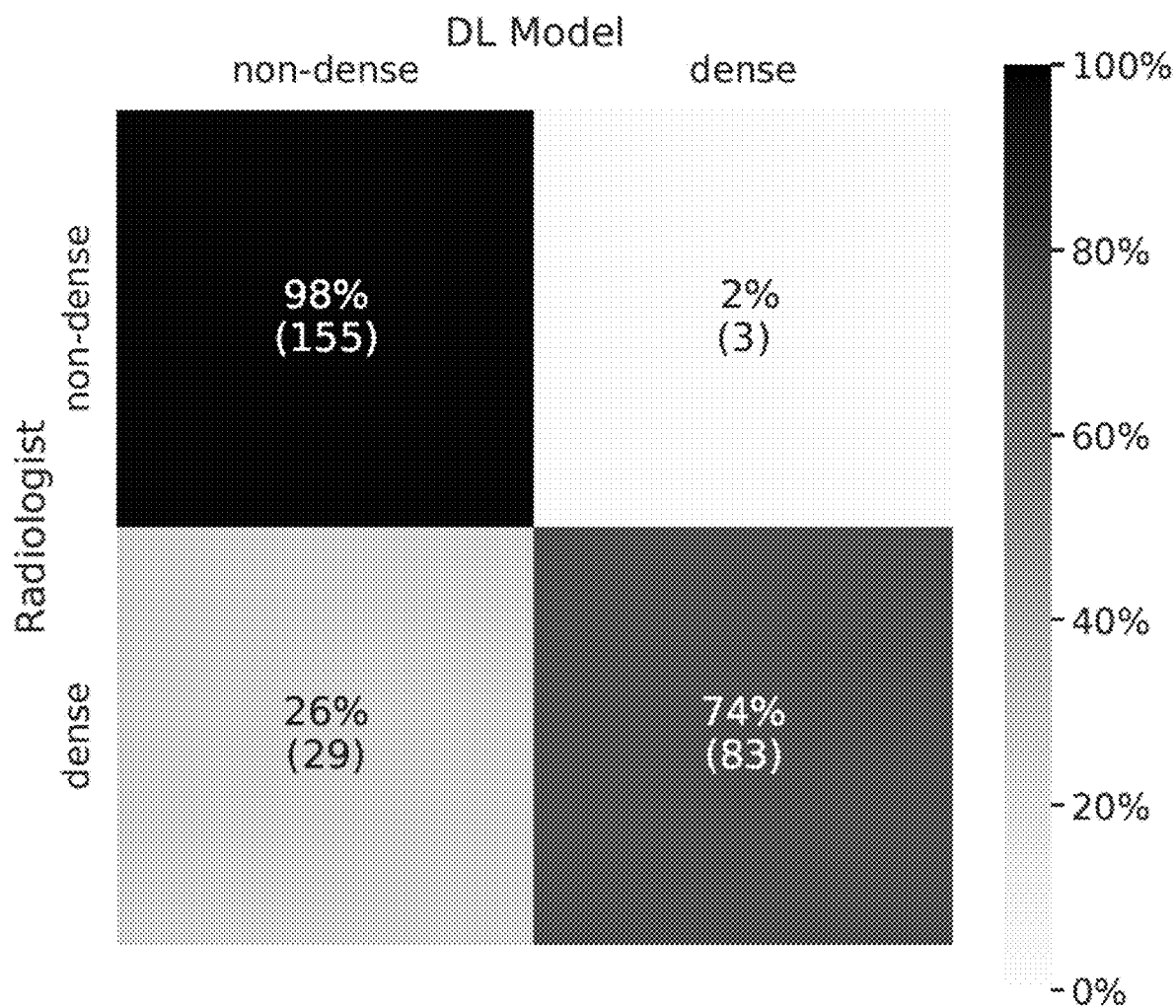
Figure 15C:
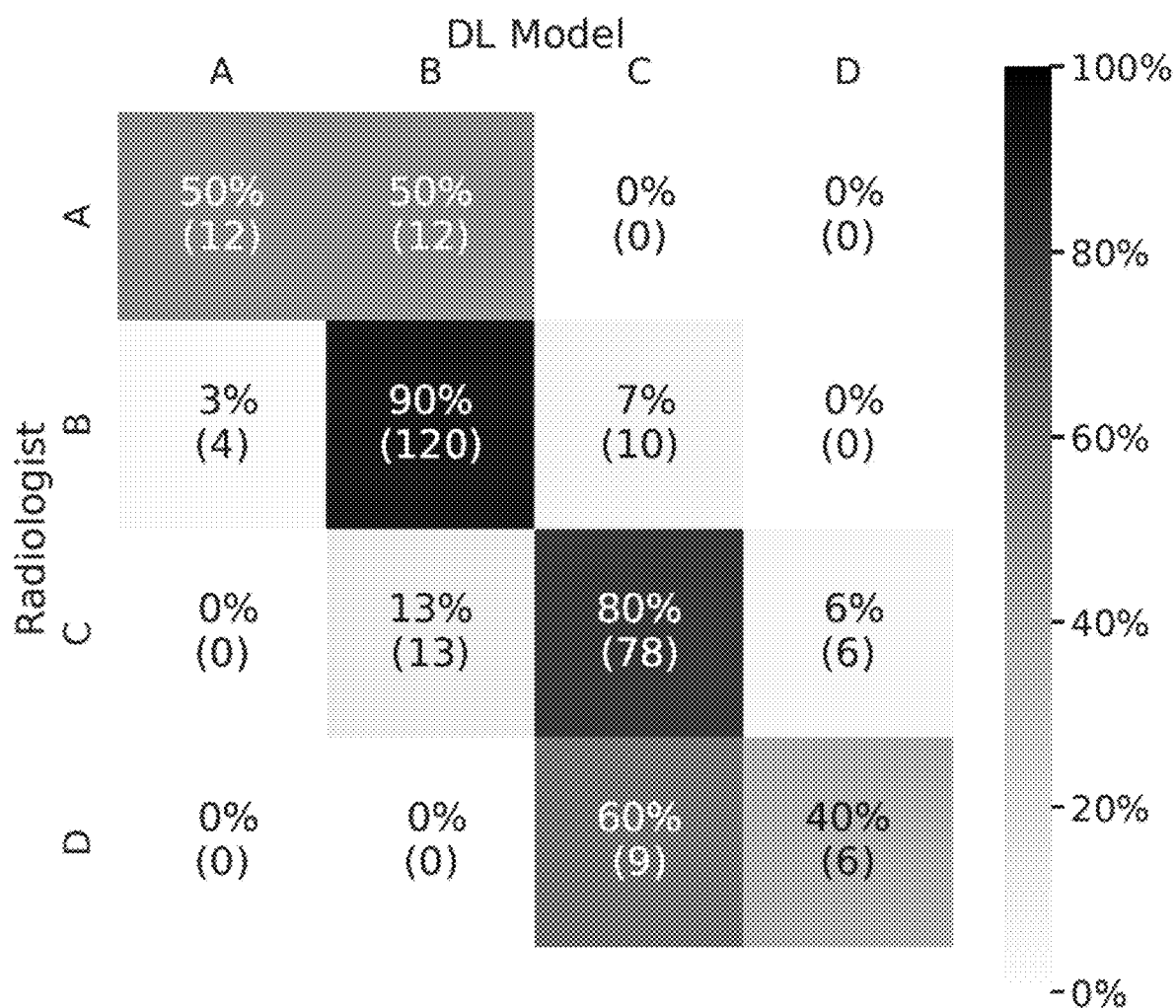
Figure 15D:
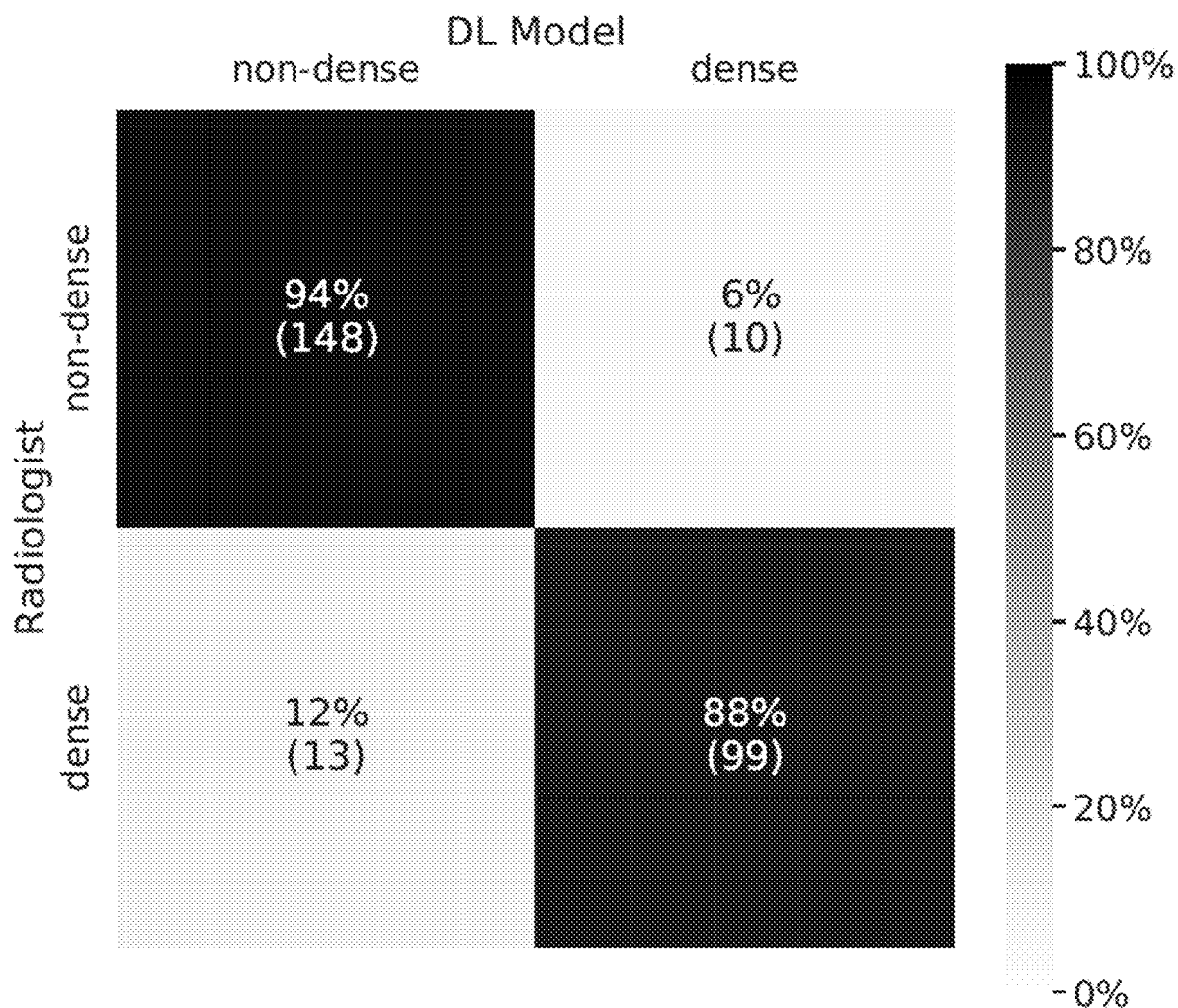
Figure 16A:
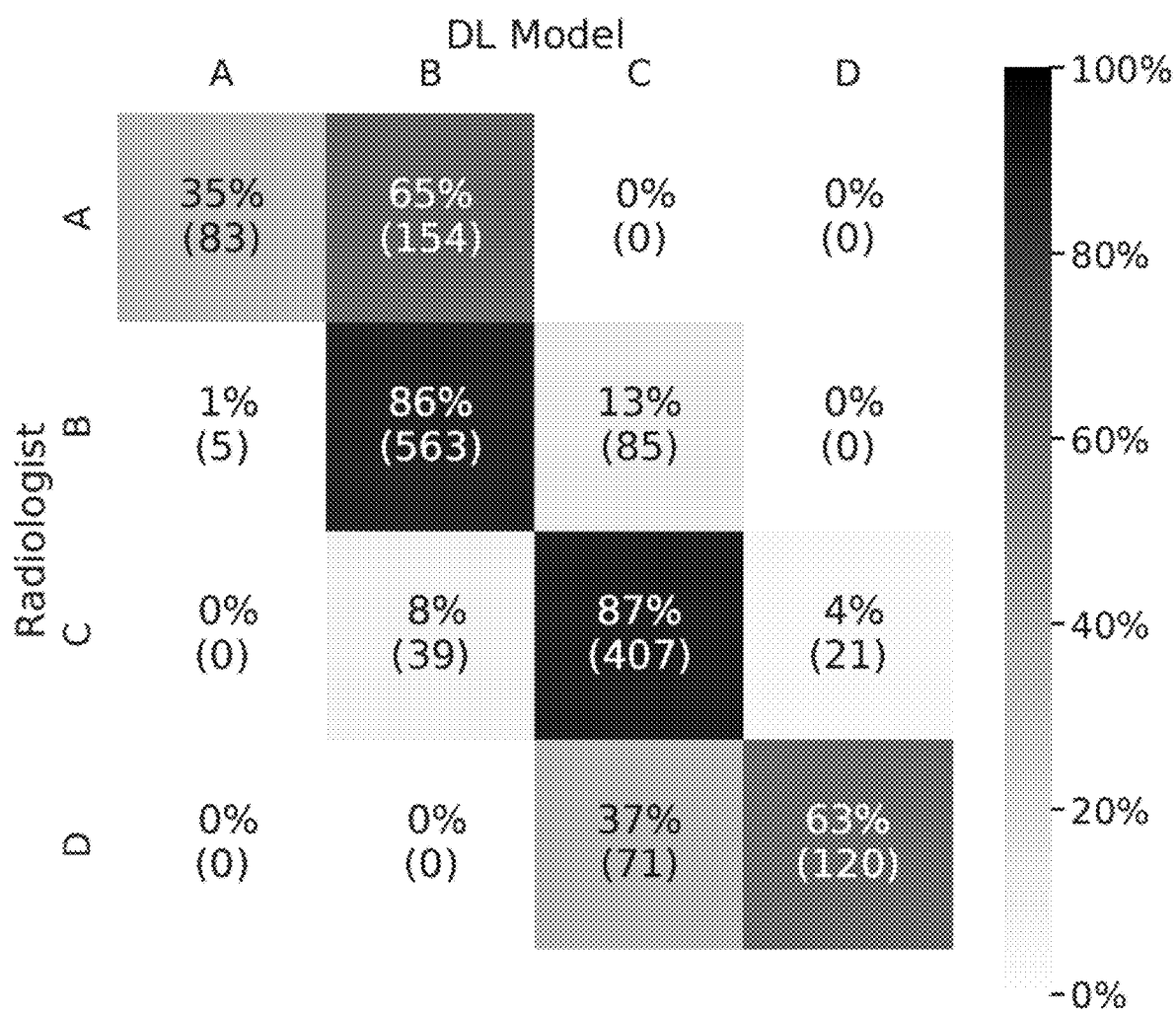
FIGS. 16A-16D show confusion matrices, evaluated on the Site 2 SM test set, for the Breast Imaging Reporting and Data System (BI-RADS) breast density task without adaptation (FIG. 16A), the binary density task (dense, BI-RADS C+D vs. non-dense, BI-RADS A+B) (FIG. 16B) without adaptation, the BI-RADS breast density task with adaptation by matrix calibration for 500 training samples (FIG. 16C), and the binary density task (dense vs. non-dense) (FIG. 16D) with adaptation by matrix calibration for 500 training samples, in accordance with disclosed embodiments. The numbers of test samples (exams) within each bin are shown in parentheses.
Figure 16B:
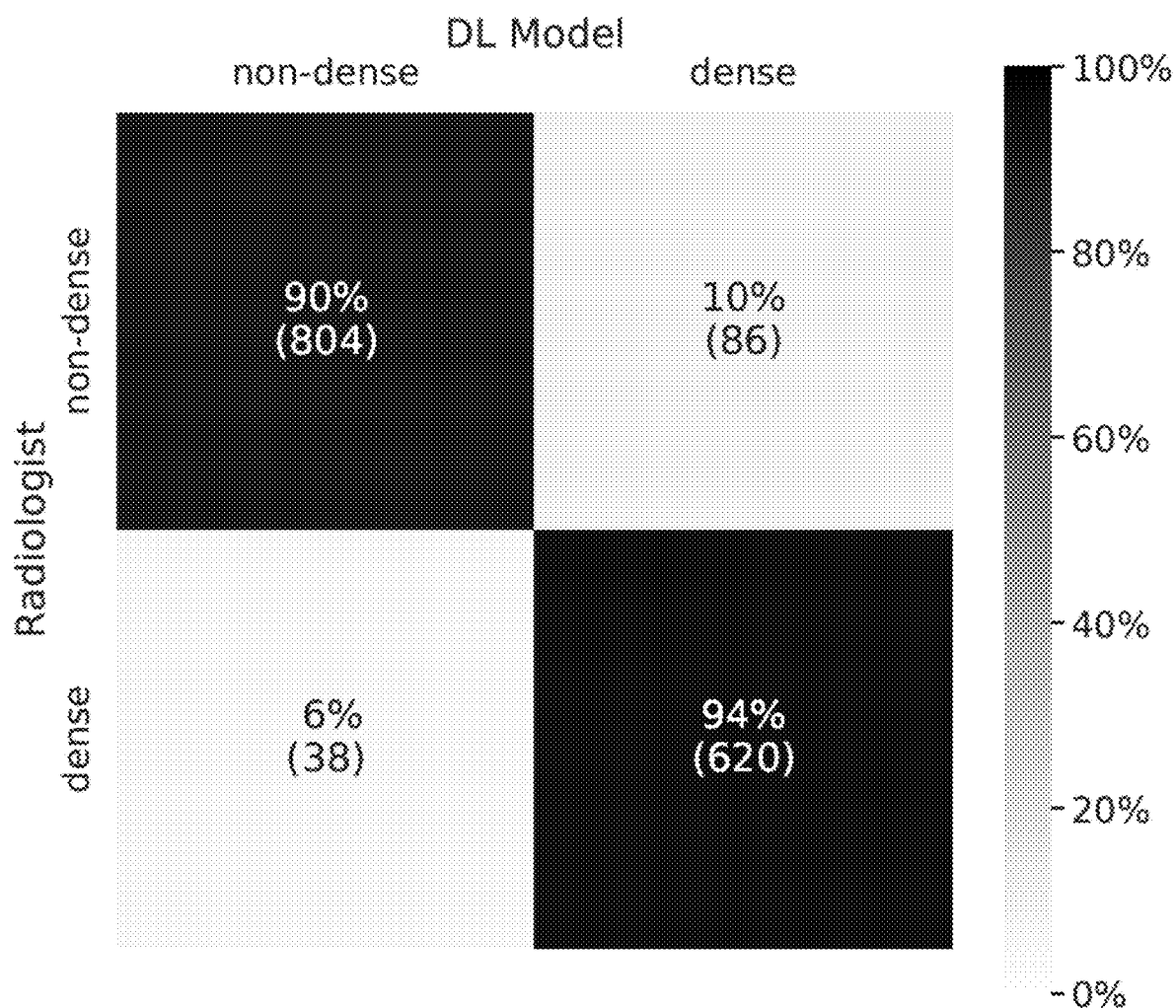
Figure 16C:
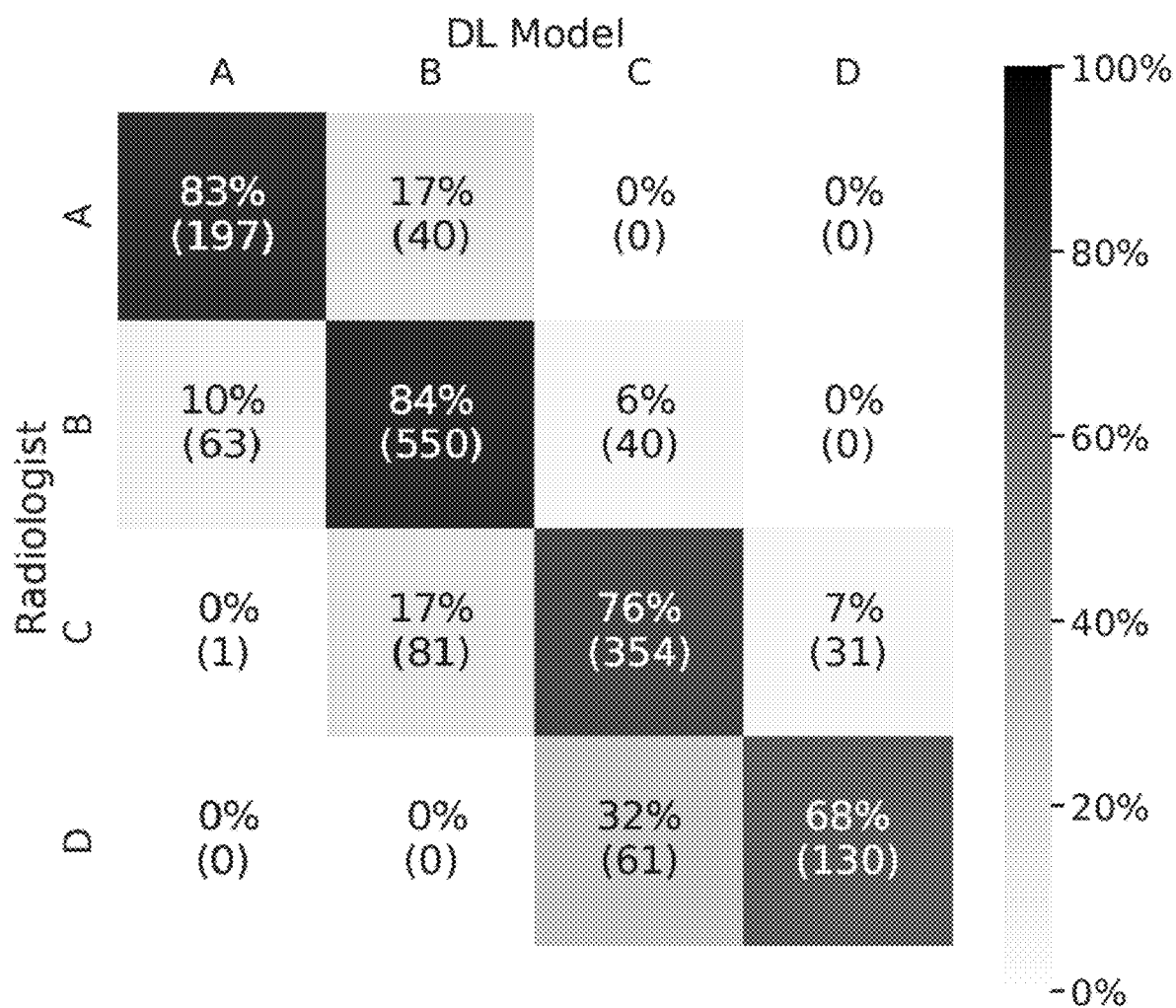
Figure 16D:
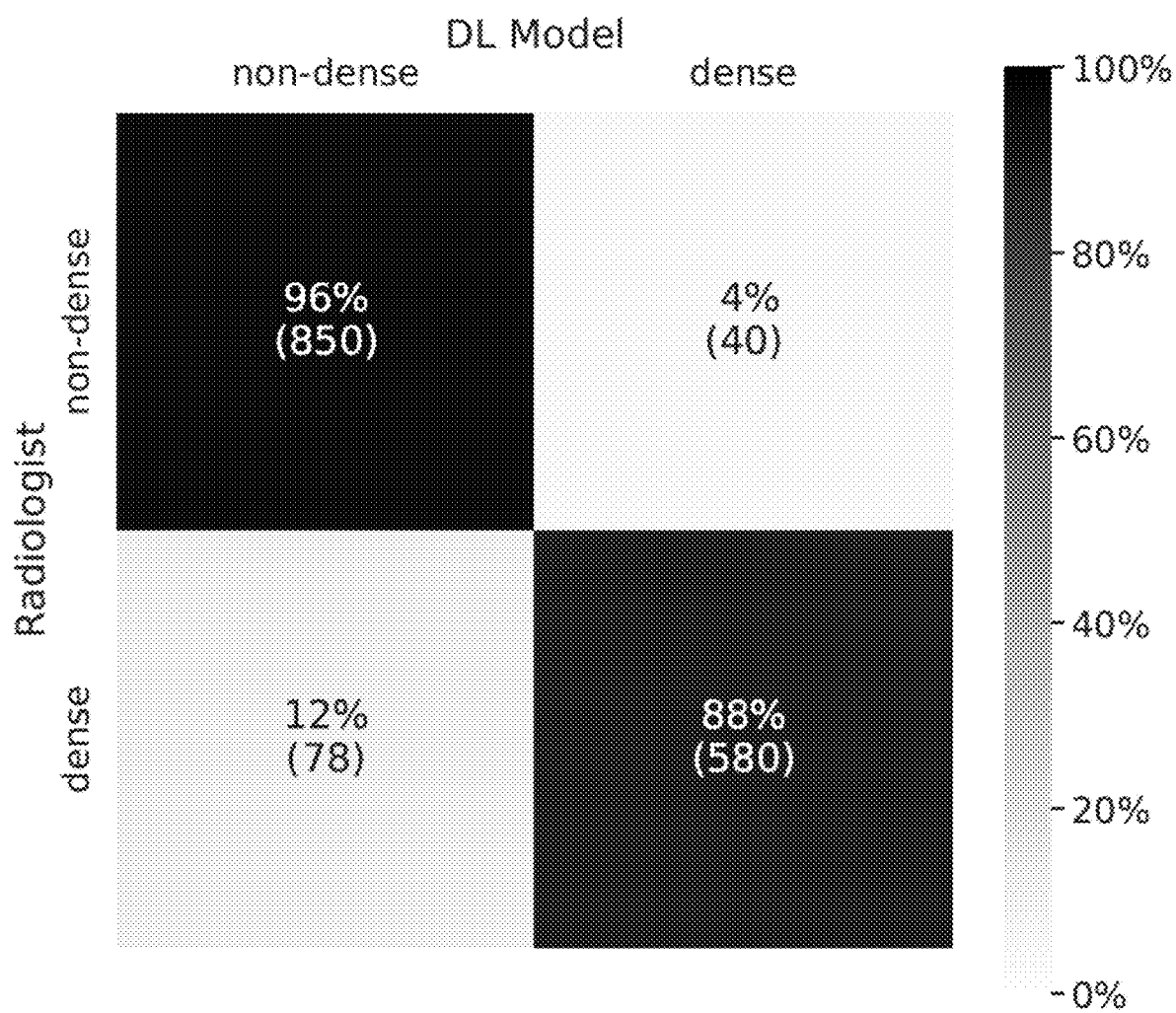

FIGS. 14A-14B show confusion matrices for the Breast Imaging Reporting and Data System (BI-RADS) breast density task (FIG. 14A) and the binary density task (dense, BI-RADS C+D vs. non-dense, BI-RADS A+B) (FIG. 14B) evaluated on the full-field digital mammography (FFDM) test set. The numbers of test samples (exams) within each bin are shown in parentheses.

TABLE 3

Performance of the deep learning model of the present disclosure on the test set for full-field digital mammography (FFDM) exams, for both the 4-class Breast Imaging Reporting and Data System (BI-RADS) breast density task and binary density task (dense, BI-RADS C + D vs. non-dense, BI-RADS A + B). 95% confidence intervals are given in brackets. Results from other studies are shown evaluated on their respective test sets as points of comparison.

|                  | 4-class Accuracy | 4-class macroAUC | 4-class Linear $\kappa$ | Binary Accuracy | Binary AUG | Binary $\kappa$ |
|---|---|---|---|---|---|---|
| Ours             | 82.2 [81.6, 82.9] | 0.952 [0.949, 0.954] | 0.75 [0.74, 0.76] | 91.1 [90.6, 91.6] | 0.971 [0.968, 0.973] | 0.81 [0.80, 0.82] |
| Lehman et al. [19] | 77 [76, 78]       |                      | 0.67 [0.66, 0.68] | 87 [86, 88]       |                      |                      |
| Wu et al. [36]   | 76.7              | 0.916                |                    | 86.5              |                      | 0.65                 |
| Volpara v1.5.0 [3] | 57              |                      | 0.57 [0.55, 0.59] | 78                |                      | 0.64 [0.61, 0.66]    |
| Quantra v2.0 [3] | 56                |                      | 0.46 [0.44, 0.47] | 83                |                      | 0.59 [0.57, 0.62]    |

In order to place the results in the context of other studies, the performance of the deep learning model on the FFDM test set was compared with results evaluated on other large FFDM datasets acquired from academic centers and with commercial breast density software (as shown in Table 3). The FFDM DL model appears to offer competitive performance.

Performance of the deep learning model on DBT exams was evaluated as follows. Results were first reported for the Site 1 SM test set (270 patients, 1080 images, mean age: 54.6, age range: 28-72), as this avoids any differences that may occur between the two sites. As shown in Table 4, when performed without adaptation, the model still demonstrated close agreement with the original reporting radiologists for the BI-RADS breast density task (accuracy=79%, CI: [74%, 84%]; $\kappa w$=0.71, CI: [0.64, 0.78]). The DL model slightly underestimates breast density for SM images (as shown in FIGS. 15A-15D), producing a BI-RADS breast density distribution (A: 10.4%, B: 57.8%, C: 28.9%, D: 3.0%) with more non-dense cases and fewer dense cases relative to the radiologists (A: 8.9%, B: 49.6%, C: 35.9%, D: 5.6%). This bias may be due to the differences shown in FIG. 13, namely that certain regions of the breast appear darker in the SM image. A similar bias has been shown for other automated breast density estimation software [33]. Agreement for the binary density task is also quite high without adaptation (accuracy=88%, CI: [84%, 92%]; $\kappa$=0.75, CI: [0.67, 0.83]; AUC=097, CI: [0.96, 0.9]).

TABLE 4

Performance of methods and systems of the present disclosure for adapting a deep learning (DL) model trained on one dataset to another with a set of 500 synthetic 2D mammography (SM) images. The datasets are denoted as "MM" for the full-field digital mammography (FFDM) dataset, "C1" for the Site 1 SM dataset, and "C2" for the Site 2 SM dataset. The performance of the model trained from scratch on the FFDM dataset (672 thousand training samples) and evaluated on its test set is also shown as a reference. 95% confidence intervals, computed by bootstrapping over the test sets, are given in brackets.

| Datasets | Methods | 4-class Accuracy | 4-class macroAUC | 4-class Linear κ | Binary Accuracy | Binary AUC | Binary |
|---|---|---|---|---|---|---|---|
| MM | | 82.2 | 0.952 | 0.75 | 91.1 | 0.971 | 0.81 |
| MM → C1 | None | 79 | 0.94 | 0.71 | 88 | 0.97 | 0.75 |
| | | [74, 84] | [0.93, 0.96] | [0.64, 0.78] | [84, 92] | [0.96, 0.99] | [0.67, 0.83] |
| | Vector | 81 | 0.95 | 0.73 | 90 | 0.97 | 0.80 |
| | | [77, 86] | [0.94, 0.97] | [0.67, 0.80] | [87, 94] | [0.96, 0.99] | [0.73, 0.88] |
| | Matrix | 80 | 0.95 | 0.72 | 91 | 0.97 | 0.82 |
| | | [76, 85] | [0.94, 0.97] | [0.66, 0.79] | [88, 95] | [0.96, 0.99] | [0.76, 0.90] |
| | Fine-tune | 81 | 0.95 | 0.73 | 90 | 0.97 | 0.80 |
| | | [76, 86] | [0.94, 0.97] | [0.67, 0.80] | [87, 94] | [0.95, 0.99] | [0.73, 0.88] |
| MM → C2 | None | 76 | 0.944 | 0.72 | 92 | 0.980 | 0.84 |
| | | [74, 78] | [0.938, 0.951] | [0.70, 0.75] | [91, 93] | [0.976, 0.986] | [0.81, 0.87] |
| | Vector | 79 | 0.954 | 0.78 | 92 | 0.979 | 0.83 |
| | | [77, 81] | [0.949, 0.961] | [0.76, 0.80] | [91, 93] | [0.974, 0.985] | [0.80, 0.86] |
| | Matrix | 80 | 0.956 | 0.79 | 92 | 0.983 | 0.84 |
| | | [78, 82] | [0.950, 0.965] | [0.76, 0.81] | [91, 94] | [0.978, 0.988] | [0.82, 0.87] |
| | Fine-tune | 80 | 0.957 | 0.79 | 93 | 0.984 | 0.85 |
| | | [78, 82] | [0.952, 0.964] | [0.77, 0.81] | [92, 94] | [0.979, 0.988] | [0.85, 0.88] |

After adaptation by matrix calibration with 500 SM images, the density distribution was more similar to that of the radiologists (A: 5.9%, B: 53.7%, C: 35.9%, D: 4.4%), while overall agreement was similar (accuracy=80%, CI: [76%, 85%]; κw=0.72, CI: [0.66, 0.79]). Accuracy for the two dense classes was improved at the expense of the two non-dense classes (as shown in FIGS. 15A-15D). A larger improvement is seen for the binary density task, where the Cohen's kappa increased from 0.75 [0.67, 0.83] to 0.82 [0.76, 0.90](accuracy=91%, CI: [88%, 95%]; AUC=0.97, CI: [0.96, 0.99]).

FIGS. 15A-15D show confusion matrices, evaluated on the Site 1 SM test set, for the Breast Imaging Reporting and Data System (BI-RADS) breast density task without adaptation (FIG. 15A), the binary density task (dense, BI-RADS C+D vs. non-dense, BI-RADS A+B) (FIG. 15B) without adaptation, the BI-RADS breast density task with adaptation by matrix calibration for 500 training samples (FIG. 15C), and the binary density task (dense vs. non-dense) (FIG. 15B) with adaptation by matrix calibration for 500 training samples. The numbers of test samples (exams) within each bin are shown in parentheses.

A high degree of agreement between the DL model and the original reporting radiologists was also observed for the Site 2 SM test set (744 patients, 6192 images, mean age: 55.2, age range: 30-92) without adaptation (accuracy=76%, CI: [74%, 78%]; κw=0.72 CI: [0.70, 0.75]; as shown in Table 4). The BI-RADS breast density distribution predicted by the DL model (A: 5.7%, B: 48.8%, C: 36.4%, D: 9.1%) was more similar to the distribution found in the Site 1 datasets. The model may have learned a prior from the Site 1 FFDM dataset that may not be optimal for Site 2 where patient demographics are different. The predicted density distribution does not appear to be skewed towards low density estimates as seen for Site 1 (as shown in FIGS. 16A-16D). This may suggest some difference in the SM images or their interpretation between the two sites. Agreement for the binary density task was especially strong (accuracy=92%, CI: [91%, 93%]; κ=0.84, CI: [0.81, 0.87]; AUC=0.980, CI: [0.976, 0.986]). The excellent performance on the Site 2 dataset without adaptation demonstrates that the DL model may be successfully generalized across sites.

With adaptation by matrix calibration for 500 training samples, performance for the BI-RADS breast density task on the Site 2 SM dataset substantially improved (accuracy=80, CI: [78, 0.82]; κw=0.79, CI: [0.76, 0.81]). After adaptation, the predicted BI-RADS breast density distribution (A: 16.9%, B: 43.3%, C: 29.4%, D: 10.4%) was more similar to that of the radiologists (A: 15.3%, B: 42.2%, C: 30.2%, D: 12.3%). Adaptation may have helped adjust for the demographic distribution of breast density at this site. Less improvement was seen for the binary breast density task (accuracy=92, CI: [91, 94]; κ=0.84, CI: [0.82, 0.87]; AUC=0.983, CI: [0.978, 0.988]).

FIGS. 16A-16D show confusion matrices, evaluated on the Site 2 SM test set, for the Breast Imaging Reporting and Data System (BI-RADS) breast density task without adaptation (FIG. 16A), the binary density task (dense, BI-RADS C+D vs. non-dense, BI-RADS A+B) (FIG. 16B) without adaptation, the BI-RADS breast density task with adaptation by matrix calibration for 500 training samples (FIG. 16C), and the binary density task (dense vs. non-dense) (FIG. 16B) with adaptation by matrix calibration for 500 training samples. The numbers of test samples (exams) within each bin are shown in parentheses.

The relative performance of different adaptation methods may depend on the number of training samples available for the adaptation, with more training samples benefiting methods with more parameters. FIGS. 17A-17D show the impact of the amount of training data on the performance of the adaptation methods, as measured by macroAUC and linearly weighted Cohen's kappa, for the Site 1 dataset (FIGS. 17A-17B, respectively) and the Site 2 SM dataset (FIGS. 17C-17D, respectively), in accordance with disclosed embodiments. Results are reported across 10 random realizations of the training data for each dataset size (as described elsewhere herein) in order to investigate the uncertainty arising from the selection of the training data rather than from the limited size of the test set, as was done when computing the 95% confidence intervals. Each adaptation method has a range of number of samples where it offers the best performance, with the region corresponding to the number of parameters for the adaptation method (vector calibration: 4+4=8 parameters; matrix calibration: 4×4+4=20 parameters; fine-tuning: 512×4+4=2052 parameters). When the number of training samples is very small (e.g., less than 100 images), some adaptation methods negatively impacted performance. Even at the largest dataset sizes, the amount of training data was too limited for the Resnet-34 model trained from scratch on SM images to exceed the performance of the models adapted from FFDM.

Figure 17A:
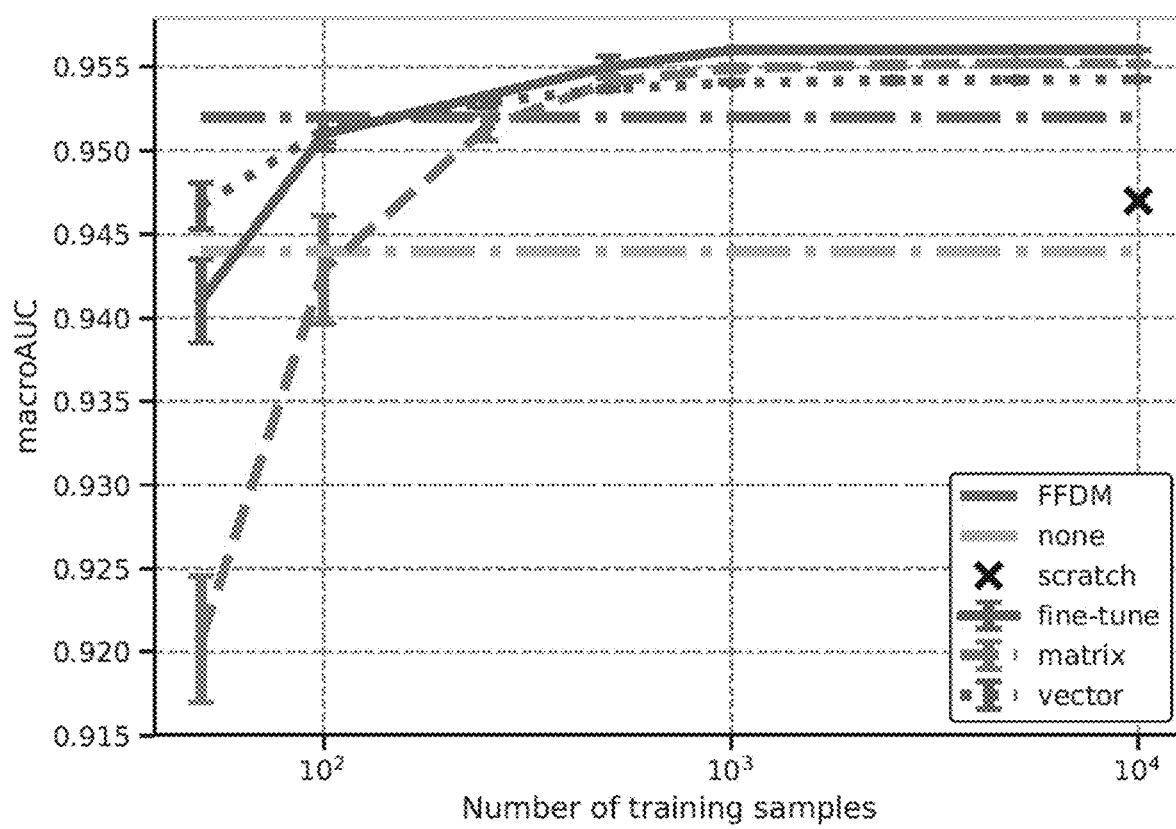
FIGS. 17A-17D show the impact of the amount of training data on the performance of the adaptation methods, as measured by macroAUC and linearly weighted Cohen's kappa, for the Site 1 dataset (FIGS. 17A-17B, respectively) and the Site 2 SM dataset (FIGS. 17C-17D, respectively), in accordance with disclosed embodiments.
Figure 17B:
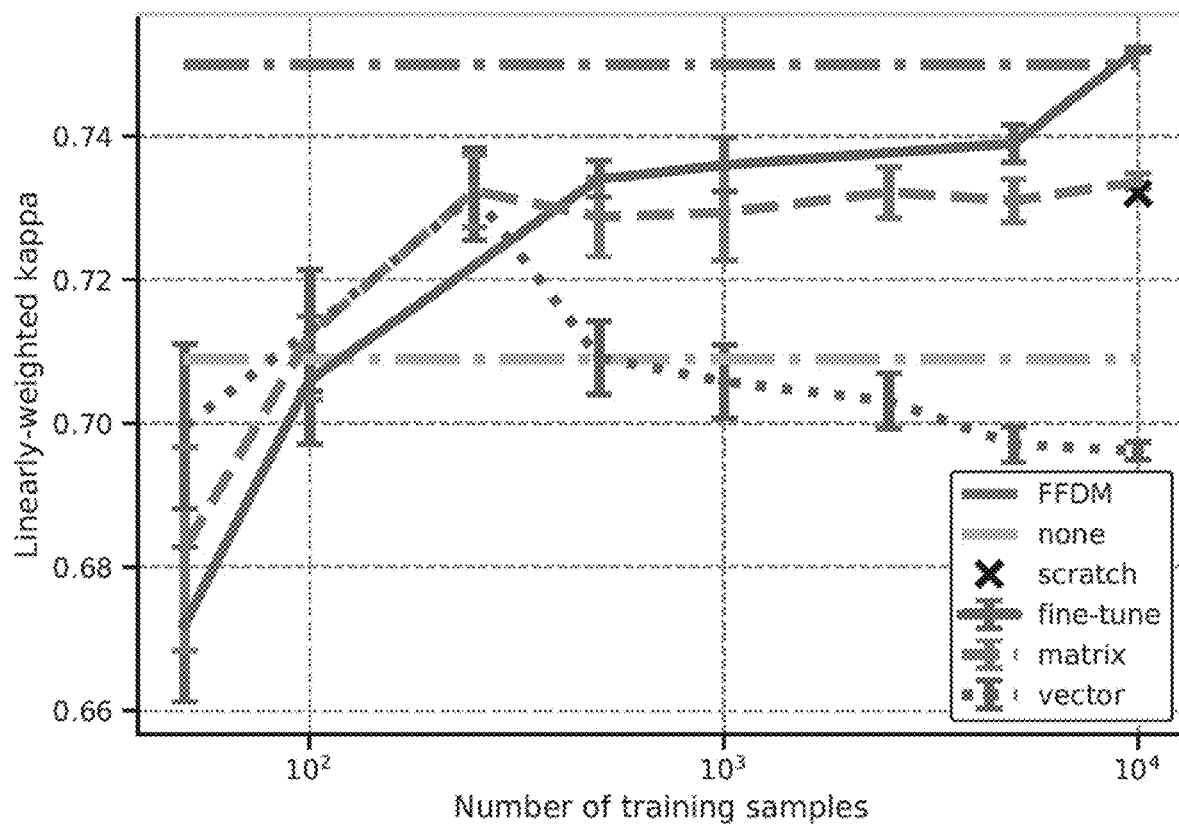
Figure 17C:
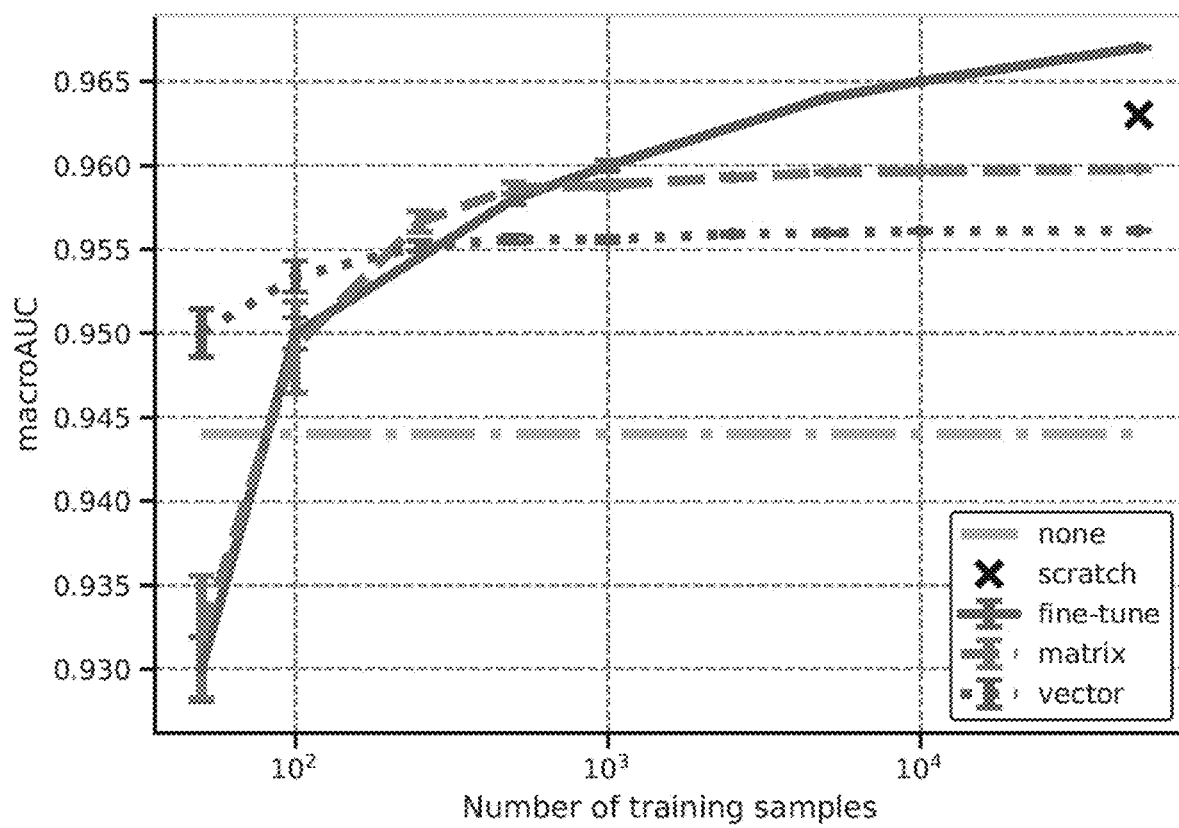
Figure 17D:
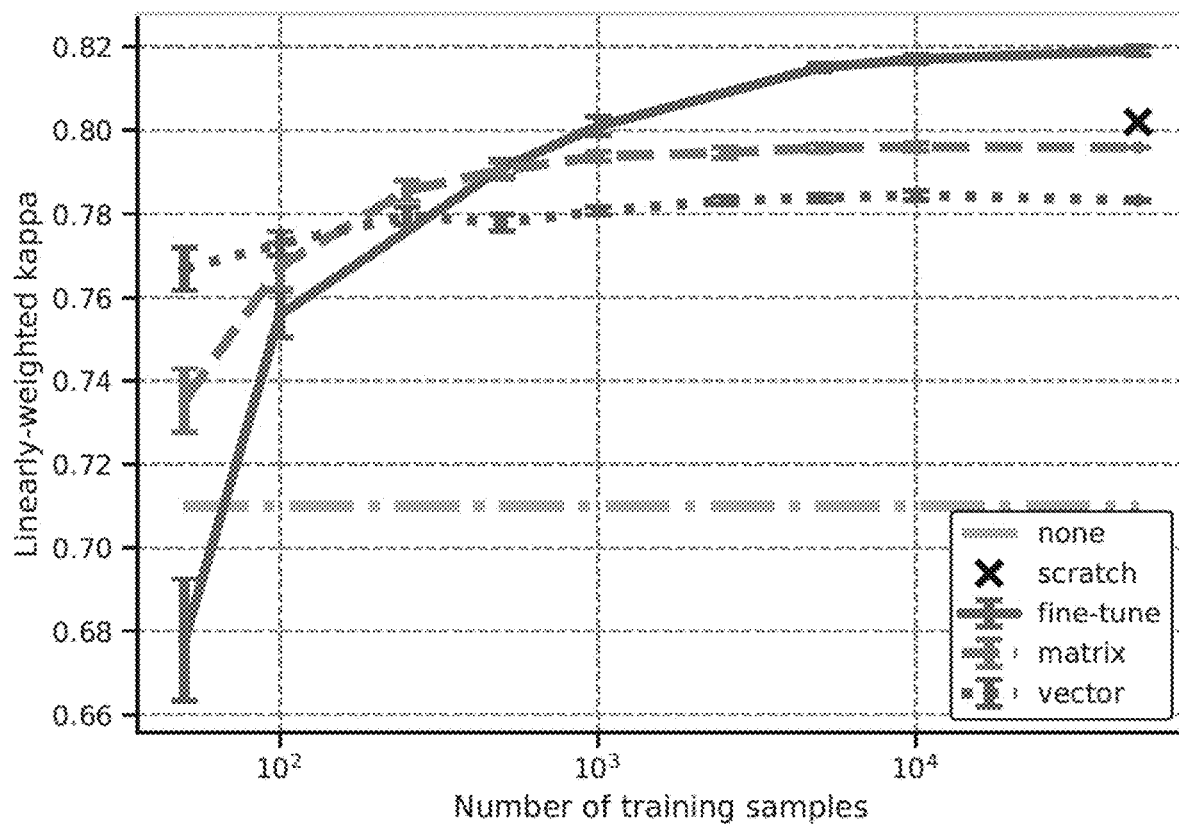

FIGS. 17A-17D show the impact of the number of training samples in the target domain on the performance of the adapted model for the Site 1 synthetic 2D mammography (SM) test set, as measured by macroAUC (FIG. 17A) and linearly weighted Cohen's kappa (FIG. 17B), and for the Site 2 SM test set, as measured by macroAUC (FIG. 17C) and linearly weighted Cohen's kappa (FIG. 17D). Results are shown for vector and matrix calibration, and retraining the last fully-connected layer (fine-tuning). Error bars indicate the standard error of the mean computed over 10 random samplings of the training data. Performance prior to adaptation (none) and training from scratch are shown as references. For the Site 1 SM studies, the full-field digital mammography (FFDM) performance served as an additional reference. Note that each graph is shown with its own full dynamic range in order to facilitate comparison of the different adaptation methods for a given metric and dataset.

Discussion

Breast Imaging Reporting and Data System (BI-RADS) breast density may be an important indicator of breast cancer risk and radiologist sensitivity, but intra- and inter-reader variability may limit the effectiveness of this measure. Deep learning (DL) models for estimating breast density may be configured to reduce this variability while still providing accurate assessments. However, these DL models were demonstrated to be applicable to digital breast tomosynthesis (DBT) exams and able to be generalized across institutions, thereby indicating suitability as a useful clinical tool. To overcome the limited training data for DBT exams, a DL model was initially trained on a large set of full-field digital mammography (FFDM) images. When evaluated on a held-out test set of FFDM images, the model showed close agreement with the radiologists reported BI-RADS breast density (κw=0.75, 95% confidence interval (CI): [0.74, 0.76]). The model was then evaluated on two datasets of synthetic 2D mammography (SM) images, which are generated as part of DBT exams. A high level of agreement was also seen for the SM dataset from the same institution as the FFDM data (Site 1: κw=0.71, CI: [0.64, 0.78]) and for the SM dataset from another institution (Site 2: κw=0.72, CI: [0.70, 0.75]). The strong performance of the DL model demonstrates that it may generalize to data from DBT exams and different institutions. Further adaptation of the model for the SM datasets led to some improvement for Site 1 (κw=0.72, CI: [0.66, 0.79]) and a more substantial improvement for Site 2 (κw=0.79, CI: [0.76, 0.81]).

When the assessments of the original reporting radiologists are accepted as the ground truth, the level of inter-reader variability among these radiologists has a large impact on the performance that can be achieved for a given dataset. For example, the performance obtained on the Site 2 SM dataset following adaptation was higher than that obtained on the FFDM dataset used to train the model. This is likely a result of limited inter-reader variability for the Site 2 SM dataset due to over 80% of the exams being read by only two readers.

In contrast with other approaches, the BI-RADS breast density DL model was evaluated on SM images from DBT exams and on data from multiple institutions. Further, as discussed above, the DL model, when evaluated on the FFDM images, demonstrated competitive performance as compared to other DL models and commercial breast density software (κw=0.75, CI: [0.74, 0.76] vs. Lehman et al. 0.67, CI: [0.66, 0.68]; Volpara 0.57, CI: [0.55, 0.59], Quantra 0.46, CI: [0.44, 0.47]) [19, 3]. For each approach, results are reported on their respective test sets, analogously to how our own results are reported.

Other measures of breast density, such as volumetric breast density, may be estimated by automated software for 3D tomosynthesis volumes or projections from DBT exams. Thresholds can be chosen to translate these measures to BI-RADS breast density, but this may result in lower levels of agreement than direct estimation of BI-RADS breast density (e.g. κw=0.47 for agreement between radiologist assessed BI-RADS breast density and that derived from volumetric breast density). Here, BI-RADS breast density is estimated from 2D SM images instead of the 3D tomosynthesis volumes, as this simplifies transfer learning from the FFDM images and mirrors the manner in which breast radiologists assess density.

In some cases, when a deep learning (DL) model is adapted to a new institution, adjustments may be made for differences in image content, patient demographics, or the interpreting radiologists across institutions. This last adjustment may result in a degree of inter-reader variability between the original and adapted DL models, though likely lower than the individual inter-reader variability if the model learns the consensus of each group of radiologists. As a result, the improved DL model performance observed following adaptation for the Site 2 SM dataset may be attributable to differences in patient demographics or radiologist assessment practices compared with the FFDM dataset. The weaker improvement for the Site 1 SM dataset may be attributable to similarities in these same factors. For the comparison of the domain adaptation techniques as a function of the number of training samples, better performance for training a DL model from scratch may be obtained by tuning the number of parameters in the model based on the number of training samples.

These results establish that the broad use of Breast Imaging Reporting and Data System (BI-RADS) breast density deep learning (DL) models holds great promise for improving clinical care. The success of the DL model without adaptation shows that the features learned by the model are largely applicable to both full-field digital mammography (FFDM) images and synthetic 2D mammography (SM) images from digital breast tomosynthesis (DBT) exams, as well as to different readers and institutions. Therefore, BI-RADS breast density DL models may be deployed to new sites and institutions without the additional effort of compiling large-scale datasets and training models from scratch. A BI-RADS breast density DL model that can generalize across sites and image types may be used to perform fast, low-cost, and more consistent estimates of breast density for women.

Example 6—Real-Time Radiology for Optimized Radiology Workflows

A machine learning-based classification system is developed to sort, prioritize, enrich, or otherwise modify radiology interpretation work (e.g., among a plurality of different workflows), based on an analysis of datasets comprising medical images of subjects. The sorting, prioritizing, enriching, or modifying of the cases for radiological assessment may be performed based on the medical image data (instead of only relying on metadata such as labels or annotation information, such as header or database elements, of the image data). For example, the medical image data may be processed by one or more image processing algorithms. The machine learning-based radiology system enables advanced radiology workflows that deliver faster and more accurate diagnoses, by allowing datasets of medical images to be stratified into different radiological assessments based on their suitability for such different assessments. For example, the plurality of different workflows may comprise radiological assessment by a plurality of different sets of radiologists. The radiologists may be on-site or remotely located relative to a clinic where the medical images of patients are acquired.

In some embodiments, the machine learning-based classification system is configured to sort or prioritize radiology interpretation work among a plurality of different workflows, based on an analysis of datasets comprising medical images of subjects. For example, one set of datasets comprising medical images may be prioritized for radiological assessment over another set of datasets comprising medical images, based on the AI triage engine's determination that the first set of datasets has a higher priority or urgency than the second set of datasets.

In some embodiments, the real-time radiology system acquires medical images of a subject through a screening exam, using an AI-enabled triage workflow, and then uses AI to deliver the radiology results (e.g., a screening result and/or a diagnostic result) within minutes (e.g., within about 5 minutes, about 10 minutes, about 15 minutes, about 30 minutes, about 45 minutes, about 60 minutes, about 90 minutes, about 2 hours, about 3 hours, about 4 hours, about 5 hours, about 6 hours, about 7 hours, or about 8 hours) to a patient after acquiring the medical images.

In some embodiments, the real-time radiology system comprises a real-time notification system for interacting with clinical staff of AI-determined alert cases. The notification system is installed at various locations in a screening clinic (e.g., at clinical staff workstations). Users (e.g., physicians and clinical staff) are assigned to roles and receive distinct notifications for each role. The notifications are triggered when an emergency is determined by a trained algorithm for a patient's case. For example, the notifications may contain both advisory information as well as permit users to enter information which can affect the patient's clinical workflow in real-time during the visit. A physician (e.g., treating physician or radiologist) is notified via real-time alerts of these emergency cases as they arise, and uses information from the notification to provide a better diagnosis.

In some embodiments, the real-time radiology system comprises a patient mobile application (app) for sending notifications to patients. The notifications may include the status of their screening/diagnostic visit, the radiological assessments performed on their medical images, presentations constructed from the radiological assessments, etc.

In some embodiments, the real-time radiology system comprises a database configured to acquire, obtain, and store for future retrieval datasets comprising medical images (e.g., radiological images), AI enrichment of datasets (e.g., medical images labeled, annotated, or processed by AI, such as via image processing algorithms), screening results, diagnostic results, and presentations of medical images and results. The real-time radiology system is configured to provide a service to patients and their clinical care providers (e.g., radiologists and clinical staff) to retrieve, access, and view the contents of the database. The real-time radiology system service may support the construction of complex computational graphs from the stored datasets, including chaining together several AI models.

Figure 18:
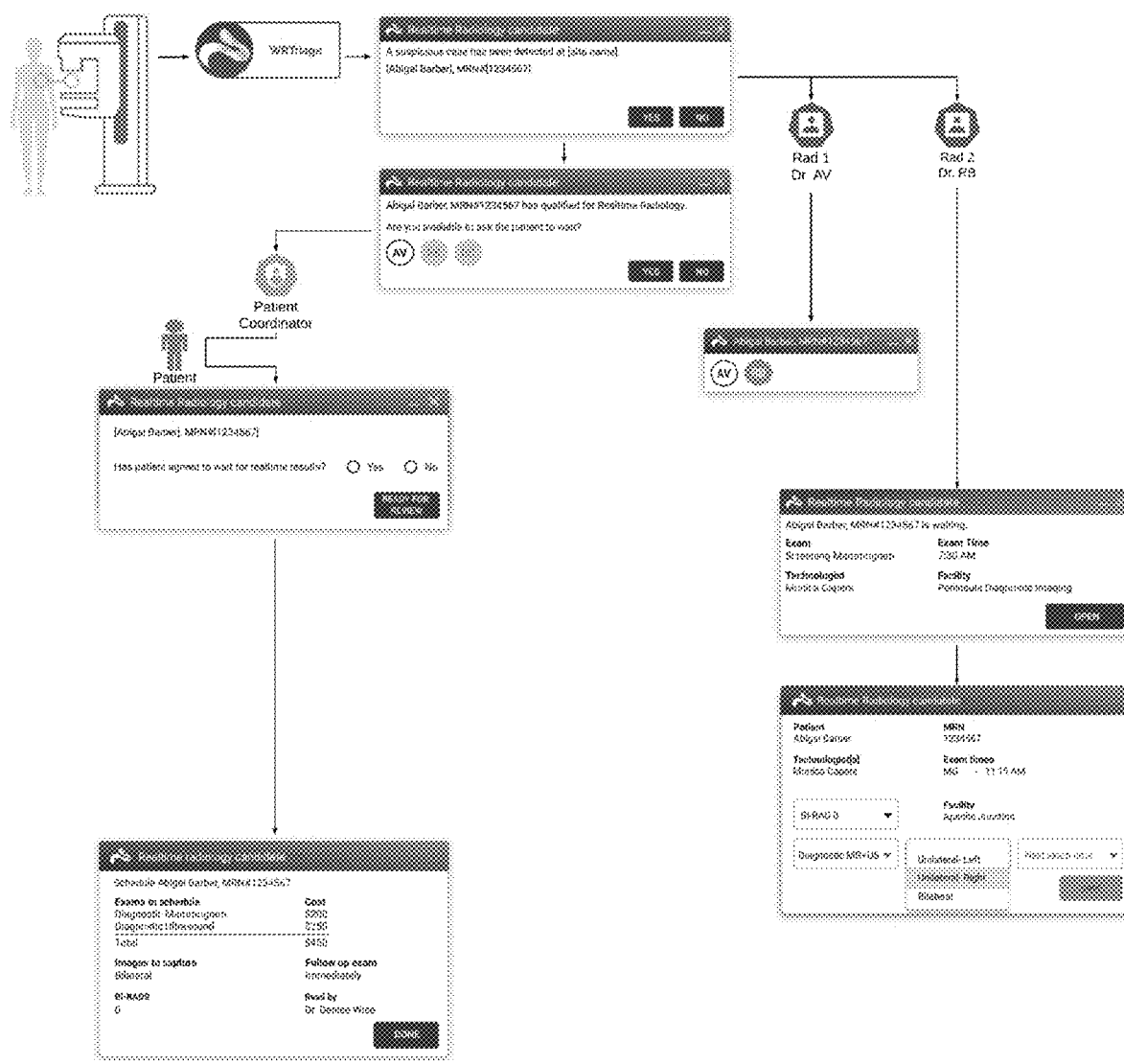
FIG. 18 shows an example of a schematic of a real-time radiology assessment workflow.

FIG. 18 shows an example of a schematic of a real-time radiology assessment workflow. The real-time radiology assessment workflow may comprise acquiring an image from a subject (e.g., via mammography). The image may be processed using systems and methods (e.g., including AI algorithms) of the present disclosure to detect that the image corresponds to a suspicious case. A clinician may be alerted that the subject is eligible for real-time radiology assessment. While the subject waits in the clinic, the image is directed to a radiologist for radiological assessment, and results of the radiological assessment are provided to the clinician for further review.

Figure 19:
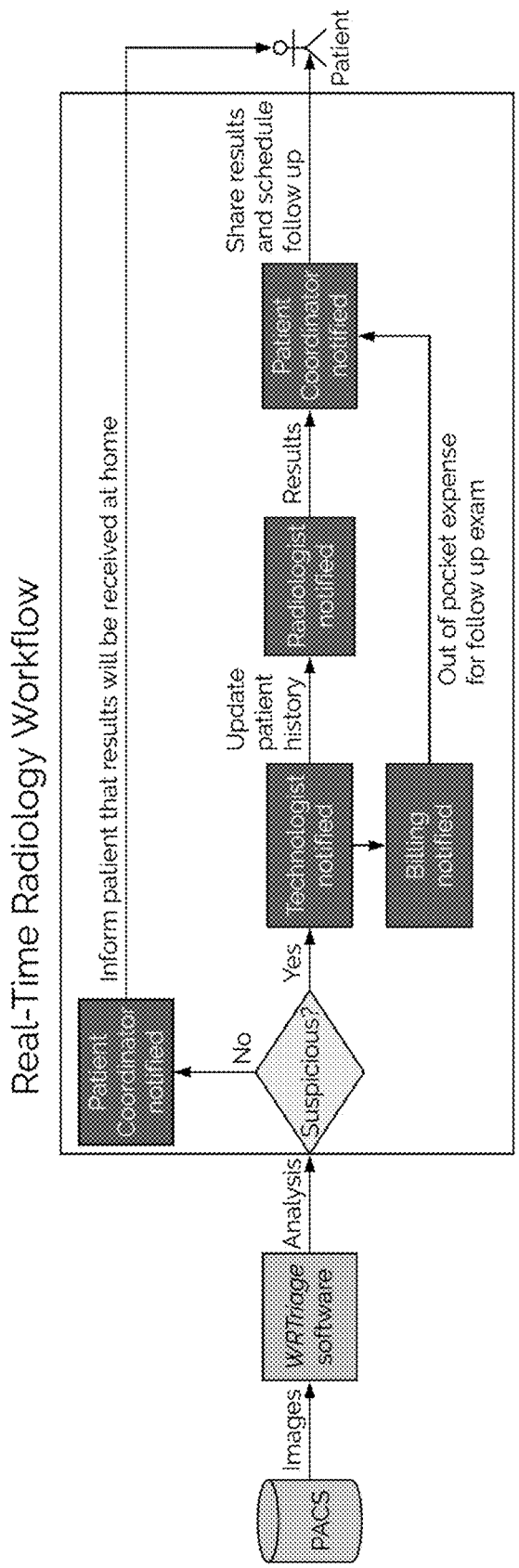
FIG. 19 shows an example of a schematic of a real-time radiology assessment workflow.

FIG. 19 shows another example of a schematic of a real-time radiology assessment workflow. Using systems and methods (e.g., including AI algorithms) of the present disclosure, images of subjects are retrieved from a PACS database and analyzed. If the AI analysis indicates that a given subject (e.g., patient) does not have a suspicious image, then a patient coordinator is notified, who then informs the patient that results will be received at home after a radiological assessment has been performed. If the AI analysis indicates that the patient has a suspicious image, then a technologist is notified, who then either (1) updates the patient history, and notifies a radiologist to perform a radiological assessment and provide results to a patient coordinator, or (2) notifies billing to process an out-of-pocket expense for a follow-up exam of the patient, and notifies the patient coordinator. The patient coordinator may share results with the patient and schedule follow-up appointments as needed.

In some embodiments, the real-time radiology assessment workflow comprises (i) directing an image or derivative thereof to a first radiologist among a first set of radiologists for radiological assessment to produce a screening result, based at least in part on whether the image is classified as suspicious; (ii) directing the image or derivative thereof to a second radiologist among a second set of radiologists for radiological assessment to produce a screening result, based at least in part on whether the image is classified as ambiguous; or (iii) directing the image or derivative thereof to a third radiologist among a third set of radiologists for radiological assessment to produce a screening result, based at least in part on whether the image is classified as normal.

In some embodiments, the real-time radiology assessment workflow comprises directing the image or derivative thereof to a first radiologist among a first set of radiologists for radiological assessment to produce a screening result, if the at least one image is classified as suspicious. In some embodiments, the real-time radiology assessment workflow comprises directing the image or derivative thereof to a second radiologist among a second set of radiologists for radiological assessment to produce a screening result, if the image is classified as ambiguous. In some embodiments, the real-time radiology assessment workflow comprises directing the image or derivative thereof to a third radiologist among a third set of radiologists for radiological assessment to produce a screening result, if the image is classified as normal.

In some embodiments, the screening result of the subject is produced at a same clinic visit as the obtaining of the image or derivative thereof. In some embodiments, the first set of radiologists is located at an on-site clinic (e.g., where the image or derivative thereof is obtained).

In some embodiments, the second set of radiologists comprises expert radiologists (e.g., who are trained to classify the image or derivative thereof as normal or suspicious at a greater accuracy than the trained algorithm). In some embodiments, the third set of radiologists is located remotely to an onsite clinic (e.g., where the image is obtained). In some embodiments, the third radiologist of the third set of radiologists performs the radiologist assessment of the image or derivative thereof among a batch comprising a plurality of images (e.g., where the batch is selected for enhanced efficiency of the radiological assessment).

In some embodiments, the real-time radiology assessment workflow comprises performing a diagnostic procedure of the subject, based at least in part on the screening result, to produce a diagnostic result of the subject. In some embodiments, the diagnostic result of the subject is produced at a same clinic visit as the obtaining of the image. In some embodiments, the diagnostic result of the subject is produced within about one hour of the obtaining of the image.

In some embodiments, the image or derivative thereof is directed to the first radiologist, the second radiologist, or the third radiologist based at least in part on additional characteristics of the location of the body of the subject. In some embodiments, the additional characteristics comprise an anatomy, tissue characteristics (e.g., tissue density or physical properties), a presence of a foreign object (e.g., implants), a type of finding, an appearance of disease (e.g., predicted by an algorithm such as a machine learning algorithm), or a combination thereof.

In some embodiments, the image or derivative thereof is directed to the first radiologist, the second radiologist, or the third radiologist based at least in part on additional characteristics of the first radiologist, the second radiologist, or the third radiologist (e.g., a personal ability of the first radiologist, the second radiologist, or the third radiologist to perform a radiological assessment of the at least one image or derivative thereof).

In some embodiments, the real-time radiology assessment workflow comprises generating an alert based at least in part on the directing of the image or derivative thereof to the first radiologist or the directing of the image or derivative thereof to the second radiologist. In some embodiments, the real-time radiology assessment workflow comprises transmitting the alert to the subject or to a clinical health care provider of the subject. In some embodiments, the real-time radiology assessment workflow comprises transmitting the alert to the subject through a patient mobile application. In some embodiments, the alert is generated in real time or substantially real time as (b).

In some embodiments, the real-time radiology system comprises an AI-powered teleradiology platform. The teleradiology platform comprises an AI-based radiology work distributor that routes cases for review by doctors in real time or substantially real time as the acquisition of medical images. The teleradiology platform may be configured to perform AI-based profiling of image types and doctors to assign each case to a doctor from among a plurality of doctors based on the suitability of the individual doctor at handling, assessing, or interpreting the datasets of the given case. The radiologists may belong to a network of radiologists, each having distinct sets of radiological skills, expertise, and experience. The teleradiology platform may assign cases to doctors based on searching the network for the doctor having the desired combination of skills, expertise, experience, and cost. The radiologists may be on-site or remotely located relative to a clinic where the medical images of patients are acquired. In some embodiments, the expertise of a radiologist may be determined by comparing his or her performance to that of an AI model for various radiologist tasks on an evaluative set of data. The radiologists may be paid for performing the radiological assessment for each individual case that they accept and perform. In some embodiments, the real-time radiology system features dynamic pricing of radiology work based on AI-determined difficulty, urgency, and value of the radiology work (e.g., radiological assessment, interpretation, or review).

In some embodiments, the real-time radiology system is configured to organize, prioritize, or stratify a plurality of medical image cases into subgroups of medical image cases for radiological assessment, interpretation, or review. The stratification of medical image cases may be performed by an AI algorithm to improve human efficiency in evaluating the individual cases, based on the image characteristics of the individual medical image cases. For example, the algorithm may group visually similar or diagnostically similar cases together for human review, such as putting identifying cases with similar lesion types in located in a similar region of anatomy.

Figure 20:
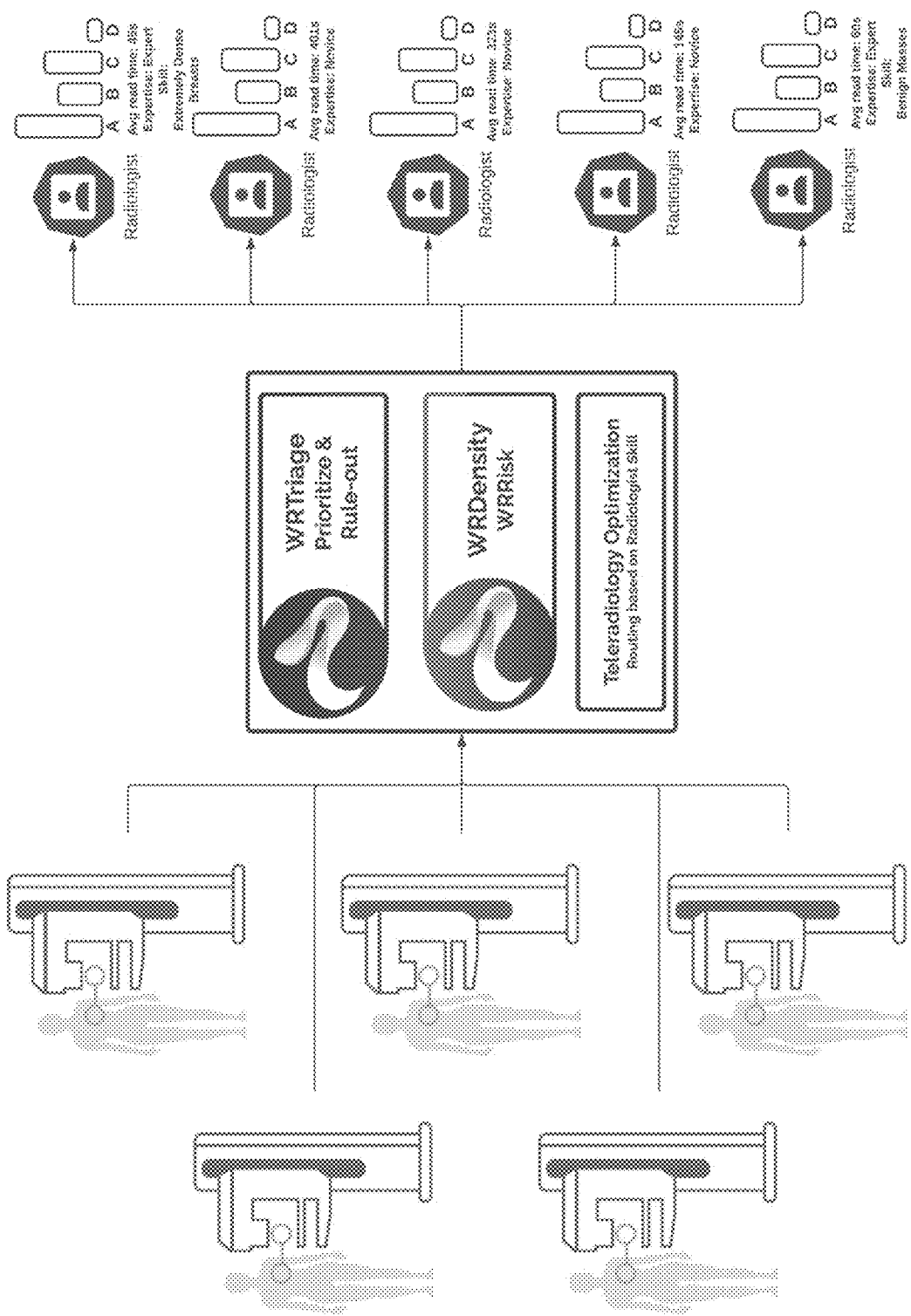
FIG. 20 shows an example of a schematic of an AI-assisted radiology assessment workflow in a teleradiology setting.

FIG. 20 shows an example of a schematic of an AI-assisted radiology assessment workflow in a teleradiology setting. Using systems and methods (e.g., including AI algorithms) of the present disclosure, images of subjects are retrieved from a PACS database and analyzed using AI algorithms to prioritize and rule out cases for radiological assessment (e.g., based on breast density and/or breast cancer risk of the subjects). The AI-assisted radiology assessment workflow may optimize routing of the cases for radiological assessment based on radiologist skill level. For example, a first radiologist may have an average read time of 45 seconds, an expertise level of expert, and a skill for assessing extremely dense breasts. As another example, a second radiologist may have an average read time of 401 seconds and an expertise level of novice. As another example, a third radiologist may have an average read time of 323 seconds and an expertise level of novice. As another example, a fourth radiologist may have an average read time of 145 seconds and an expertise level of novice. For example, a fifth radiologist may have an average read time of 60 seconds, an expertise level of expert, and a skill for assessing benign masses. The AI-assisted radiology assessment workflow may direct a given subject's case to a radiologist selected from among the first, second, third, fourth, or fifth radiologist, based on their average read time, expertise level, and/or skill level appropriate for the given subject's case.

In some embodiments, the AI-assisted radiology assessment workflow comprises (i) directing an image or derivative thereof to a first radiologist among a first set of radiologists for radiological assessment to produce a screening result, based at least in part on whether the image is classified as suspicious; (ii) directing the image or derivative thereof to a second radiologist among a second set of radiologists for radiological assessment to produce a screening result, based at least in part on whether the image is classified as ambiguous; or (iii) directing the image or derivative thereof to a third radiologist among a third set of radiologists for radiological assessment to produce a screening result, based at least in part on whether the image is classified as normal.

In some embodiments, the AI-assisted radiology assessment workflow comprises directing the image or derivative thereof to a first radiologist among a first set of radiologists for radiological assessment to produce a screening result, if the at least one image is classified as suspicious. In some embodiments, the AI-assisted radiology assessment workflow comprises directing the image or derivative thereof to a second radiologist among a second set of radiologists for radiological assessment to produce a screening result, if the image is classified as ambiguous. In some embodiments, the AI-assisted radiology assessment workflow comprises directing the image or derivative thereof to a third radiologist among a third set of radiologists for radiological assessment to produce a screening result, if the image is classified as normal.

In some embodiments, the screening result of the subject is produced at a same clinic visit as the obtaining of the image or derivative thereof. In some embodiments, the first set of radiologists is located at an on-site clinic (e.g., where the image or derivative thereof is obtained).

In some embodiments, the second set of radiologists comprises expert radiologists (e.g., who are trained to classify the image or derivative thereof as normal or suspicious at a greater accuracy than the trained algorithm). In some embodiments, the third set of radiologists is located remotely to an onsite clinic (e.g., where the image is obtained). In some embodiments, the third radiologist of the third set of radiologists performs the radiologist assessment of the image or derivative thereof among a batch comprising a plurality of images (e.g., where the batch is selected for enhanced efficiency of the radiological assessment).

In some embodiments, the AI-assisted radiology assessment workflow comprises performing a diagnostic procedure of the subject, based at least in part on the screening result, to produce a diagnostic result of the subject. In some embodiments, the diagnostic result of the subject is produced at a same clinic visit as the obtaining of the image. In some embodiments, the diagnostic result of the subject is produced within about one hour of the obtaining of the image.

In some embodiments, the image or derivative thereof is directed to the first radiologist, the second radiologist, or the third radiologist based at least in part on additional characteristics of the location of the body of the subject. In some embodiments, the additional characteristics comprise an anatomy, tissue characteristics (e.g., tissue density or physical properties), a presence of a foreign object (e.g., implants), a type of finding, an appearance of disease (e.g., predicted by an algorithm such as a machine learning algorithm), or a combination thereof.

In some embodiments, the image or derivative thereof is directed to the first radiologist, the second radiologist, or the third radiologist based at least in part on additional characteristics of the first radiologist, the second radiologist, or the third radiologist (e.g., a personal ability of the first radiologist, the second radiologist, or the third radiologist to perform a radiological assessment of the at least one image or derivative thereof).

In some embodiments, the AI-assisted radiology assessment workflow comprises generating an alert based at least in part on the directing of the image or derivative thereof to the first radiologist or the directing of the image or derivative thereof to the second radiologist. In some embodiments, the AI-assisted radiology assessment workflow comprises transmitting the alert to the subject or to a clinical health care provider of the subject. In some embodiments, the AI-assisted radiology assessment workflow comprises transmitting the alert to the subject through a patient mobile application. In some embodiments, the alert is generated in real time or substantially real time as (b).

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method for processing at least one image of a location of a body of said subject, comprising:
   (a) obtaining said at least one image of said location of a body of said subject;
   (b) using a trained machine learning classifier to classify said at least one image or a derivative thereof to a category among a plurality of categories, wherein said classifying comprises applying an image processing algorithm to said at least one image or derivative thereof;
   (c) upon classifying said at least one image or derivative thereof in (b), (i) directing said at least one image or derivative thereof to a first radiologist for radiological assessment if said at least one image is classified to a first category among said plurality of categories, or (ii) directing said at least one image or derivative thereof to a second radiologist for radiological assessment, if said at least one image is classified to a second category among said plurality of categories,
   wherein (c) is performed in real time or substantially real time as (b); and
   (d) receiving a radiological assessment of said subject from said first or second radiologist based at least in part on a radiological analysis of said at least one image or derivative thereof.

2. The method of claim 1, wherein (b) further comprises classifying said at least one image or derivative thereof as normal, ambiguous, or suspicious.

3. The method of claim 2, further comprising directing said at least one image or derivative thereof to a classifier based on said classification of said at least one image or derivative thereof in (b).

4. The method of claim 3, wherein (c) further comprises directing said at least one image or derivative thereof to a first radiologist from among a first plurality of radiologists or to a second radiologist from among a second plurality of radiologists for radiological assessment.

5. The method of claim 2, wherein said trained machine learning classifier is configured to identify at least one region of said at least one image or derivative thereof that contains or is suspected of containing said anomalous tissue.

6. The method of claim 2, wherein a trained machine learning classifier classifies said at least one image or a derivative thereof as normal, ambiguous, or suspicious for being indicative of a cancer.

7. The method of claim 6, wherein said cancer comprises breast cancer.

8. The method of claim 7, wherein said at least one image or derivative thereof comprises a three-dimensional image of at least a portion of a breast of said subject.

9. The method of claim 1, wherein said at least one image or derivative thereof comprises a medical image.

10. The method of claim 1, wherein said trained machine learning classifier comprises a deep learning algorithm, a support vector machine (SVM), a neural network, or a Random Forest.

11. The method of claim 1, further comprising monitoring said subject, wherein said monitoring comprises assessing images of said location of said body of said subject at a plurality of time points, wherein said assessing is based at least in part on said classification of said at least one image or a derivative thereof as normal, ambiguous, or suspicious at each of said plurality of time points.

12. The method of claim 11, wherein a difference in said assessment of said images of said body of said subject at said plurality of time points is indicative of one or more clinical indications selected from the group consisting of: (i) a diagnosis of said subject, (ii) a prognosis of said subject, and (iii) an efficacy or non-efficacy of a course of treatment of said subject.

13. The method of claim 1, wherein applying said image processing algorithm further comprises identifying regions of interest within said at least one image or derivative thereof, and labeling said regions of interest to produce at least one labeled image.

14. The method of claim 1, wherein said at least one image comprises a plurality of images obtained from said subject, wherein said plurality of images are obtained using different modalities or at different time points.

15. The method of claim 1, wherein said classifying further comprises processing clinical health data of said subject.

16. A method for processing at least one image of a location of a body of said subject, comprising:
(a) obtaining said at least one image of said location of a body of said subject;
(b) using a trained machine learning classifier to classify said at least one image or a derivative thereof to a category among a plurality of categories, wherein said classifying comprises applying an image processing algorithm to said at least one image or derivative thereof,
wherein (b) further comprises classifying said at least one image or derivative thereof as normal, ambiguous, or suspicious;
(c) upon classifying said at least one image or derivative thereof in (b), (i) directing said at least one image or derivative thereof to a first radiologist for radiological assessment if said at least one image is classified to a first category among said plurality of categories, or (ii) directing said at least one image or derivative thereof to a second radiologist for radiological assessment, if said at least one image is classified to a second category among said plurality of categories; and
(d) receiving a radiological assessment of said subject from said first or second or third radiologist, based at least in part on a radiological analysis of said at least one image or derivative thereof,
wherein (c) further comprises (i) directing said at least one image or derivative thereof to a first radiologist among a first set of radiologists for radiological assessment to produce a screening result, based at least in part on whether said at least one image or derivative thereof is classified as suspicious; (ii) directing said at least one image or derivative thereof to a second radiologist among a second set of radiologists for radiological assessment to produce a screening result, based at least in part on whether said at least one image or derivative thereof is classified as ambiguous; or (iii) directing said at least one image or derivative thereof to a third radiologist among a third set of radiologists for radiological assessment to produce a screening result, based at least in part on whether said at least one image derivative thereof is classified as normal.

17. The method of claim 16, wherein said screening result of said subject is produced at a same clinic visit as said obtaining of said at least one image or derivative thereof.

18. The method of claim 16, wherein said first set of radiologists is located at an on-site clinic, wherein said at least one image or derivative thereof is obtained at said on-site clinic.

19. The method of claim 16, wherein said second set of radiologists comprises expert radiologists, which expert radiologists are trained to classify said at least one image or derivative thereof as normal or suspicious at a greater accuracy than said trained machine learning classifier.

20. The method of claim 16, wherein said third set of radiologists is located remotely to an onsite clinic, wherein said at least one image is obtained at said on-site clinic.

21. The method of claim 16, wherein said third radiologist of said third set of radiologists performs said radiologist assessment of said at least one image or derivative thereof among a batch comprising a plurality of images, wherein said batch is selected for enhanced efficiency of said radiological assessment.

22. The method of claim 16, further comprising performing a diagnostic procedure of said subject, based at least in part on said screening result, to produce a diagnostic result of said subject.

23. The method of claim 16, wherein said at least one image or derivative thereof is directed to said first radiologist, said second radiologist, or said third radiologist, based at least in part on additional characteristics of said location of said body of said subject.

24. The method of claim 23, wherein said additional characteristics comprise an anatomy, tissue characteristics, a presence of a foreign object, a type of finding, an of disease, or a combination thereof.

25. A method for processing at least one image of a location of a body of said subject, comprising:
(a) obtaining said at least one image of said location of a body of said subject;
(b) using a trained machine learning classifier to classify said at least one image or a derivative thereof to a category among a plurality of categories, wherein said classifying comprises applying an image processing algorithm to said at least one image or derivative thereof;
(c) upon classifying said at least one image or derivative thereof in (b), (i) directing said at least one image or derivative thereof to a first radiologist for radiological assessment if said at least one image is classified to a first category among said plurality of categories, or (ii) directing said at least one image or derivative thereof to a second radiologist for radiological assessment, if said at least one image is classified to a second category among said plurality of categories; and (d) receiving a radiological assessment of said subject from said first or second radiologist based at least in part on a radiological analysis of said at least one image or derivative thereof, wherein (c) further comprises generating an alert based at least in part on said directing of said at least one image or derivative thereof to said first radiologist or said directing of said at least one image or derivative thereof to said second radiologist.

26. The method of claim 25, further comprising transmitting said alert to said subject or to a clinical health care provider of said subject.

27. The method of claim 25, wherein said alert is generated in real time or substantially real time as (b).

28. A computer system for processing at least one image of a location of a body of said subject:

a database that is configured to store said at least one image of said location of a body of said subject; and one or more computer processors operatively coupled to said database, wherein said one or more computer processors are individually or collectively programmed to:

(a) use a trained machine learning classifier to classify said at least one image or a derivative thereof to a category among a plurality of categories, wherein said classifying comprises applying an image processing algorithm to said at least one image or derivative thereof;

(b) upon classifying said at least one image or derivative thereof in (b), (i) directing said at least image or derivative thereof to a first radiologist for radiological assessment if said at least one image is classified to a first category among said plurality of categories, or (ii) directing said at least one image or derivative thereof to a second radiologist for radiological assessment, if said at least one image is classified to a second category among said plurality of categories, wherein (b) is performed in real time or substantially real time as (a); and (c) receive a radiological assessment of said subject from said first or second radiologist based at least in part on a radiological analysis of said at least one image or derivative thereof.

29. A non-transitory computer readable medium comprising machine-executable code that, upon execution by one or more computer processors, implements a method for processing at least one image of a location of a body of said subject, comprising:

(a) obtaining said at least one image of said location of a body of said subject;

(b) using a trained machine learning classifier to classify said at least one image or a derivative thereof to a category among a plurality of categories, wherein said classifying comprises applying an image processing algorithm to said at least one image or derivative thereof;

(c) upon classifying said at least one image or derivative thereof in (b), (i) directing said at least image or derivative thereof to a first radiologist for radiological assessment if said at least one image is classified to a first category among said plurality of categories, or (ii) directing said at least one image or derivative thereof to a second radiologist for radiological assessment, if said at least one image is classified to a second category among said plurality of categories, wherein (c) is performed in real time or substantially real time as (b); and (d) receiving a radiological assessment of said subject from said first or second radiologist based at least in part on a radiological analysis of said at least one image or derivative thereof.

* * * * *

UNITED STATES PATENT AND TRADEMARK OFFICE
CERTIFICATE OF CORRECTION

PATENT NO. : 12,347,104 B2
APPLICATION NO. : 17/860310
DATED : July 1, 2025
INVENTOR(S) : Jason Su et al.

Page 1 of 1

It is certified that error appears in the above-identified patent and that said Letters Patent is hereby corrected as shown below:

In the Claims

Column 58, Lines 15 and 16, Claim 16:
Replace "at least in part on whether said at least one image derivative thereof is classified as normal."
with --at least in part on whether said at least one image or derivative thereof is classified as normal.--.

Signed and Sealed this
Twelfth Day of August, 2025

Coke Morgan Stewart
*Acting Director of the United States Patent and Trademark Office*